(12) United States Patent
Liu et al.

(10) Patent No.: US 12,410,206 B2
(45) Date of Patent: Sep. 9, 2025

(54) OLIGOSACCHARIDE COMPOSITIONS AND METHODS OF USE THEREOF FOR REDUCING AMMONIA LEVELS

(71) Applicant: DSM Nutritional Products, LLC, Parsippany, NJ (US)

(72) Inventors: Christopher Matthew Liu, Somerville, MA (US); John M. Geremia, Watertown, MA (US); Anastasia Lioubomirov, San Jose, CA (US); Max Hecht, Lexington, MA (US)

(73) Assignee: DSM Nutritional Products, LLC, Parsippany, NJ (US)

( * ) Notice: Subject to any disclaimer, the term of this patent is extended or adjusted under 35 U.S.C. 154(b) by 901 days.

(21) Appl. No.: 17/269,721

(22) PCT Filed: Aug. 21, 2019

(86) PCT No.: PCT/US2019/047595
§ 371 (c)(1),
(2) Date: Feb. 19, 2021

(87) PCT Pub. No.: WO2020/041531
PCT Pub. Date: Feb. 27, 2020

(65) Prior Publication Data
US 2021/0198302 A1 Jul. 1, 2021

Related U.S. Application Data

(60) Provisional application No. 62/845,295, filed on May 8, 2019, provisional application No. 62/757,723, filed on Nov. 8, 2018, provisional application No. 62/755,461, filed on Nov. 3, 2018, provisional application No. 62/720,924, filed on Aug. 21, 2018.

(51) Int. Cl.
*C07H 3/06* (2006.01)
*A23L 33/00* (2016.01)
*A23L 33/125* (2016.01)
*A23L 33/21* (2016.01)
*A61P 3/00* (2006.01)
*C08L 5/00* (2006.01)

(52) U.S. Cl.
CPC .............. *C07H 3/06* (2013.01); *A23L 33/125* (2016.08); *A23L 33/21* (2016.08); *A23L 33/40* (2016.08); *A61P 3/00* (2018.01); *C08L 5/00* (2013.01); *A23V 2002/00* (2013.01)

(58) Field of Classification Search
CPC ................ C07H 3/06; C07H 3/04; A61P 3/00
See application file for complete search history.

(56) References Cited

U.S. PATENT DOCUMENTS

| | | |
|---|---|---|
| 3,766,165 A | 10/1973 | Rennhard |
| 5,085,883 A | 2/1992 | Garleb et al. |
| 6,559,302 B1 | 5/2003 | Shah et al. |
| 6,852,707 B1 | 2/2005 | Kiso et al. |
| 8,466,242 B2 | 6/2013 | Geremia et al. |
| 8,476,388 B2 | 7/2013 | Geremia et al. |
| 9,079,171 B2 | 7/2015 | Geremia et al. |
| 9,205,418 B2 | 12/2015 | Geremia et al. |
| 9,238,845 B2 | 1/2016 | Baynes et al. |
| 9,487,764 B2 | 11/2016 | Falb et al. |
| 9,492,473 B2 | 11/2016 | von Maltzahn et al. |
| 9,757,403 B2 | 9/2017 | von Maltzahn et al. |
| 9,901,595 B2 | 2/2018 | von Maltzahn et al. |
| 10,131,721 B2 | 11/2018 | Geremia et al. |
| 10,314,853 B2 | 6/2019 | von Maltzahn et al. |
| 10,702,542 B2 | 7/2020 | von Maltzahn et al. |
| 10,752,705 B2 | 8/2020 | Geremia et al. |
| 10,787,527 B2 | 9/2020 | Geremia et al. |
| 10,849,337 B2 | 12/2020 | Geremia et al. |
| 10,881,676 B2 | 1/2021 | von Maltzahn et al. |
| 10,894,057 B2 | 1/2021 | von Maltzahn et al. |
| 11,169,101 B2 | 11/2021 | Liu et al. |
| 11,229,660 B2 | 1/2022 | von Maltzahn et al. |
| 11,584,805 B2 | 2/2023 | Geremia et al. |
| 11,653,676 B2 | 5/2023 | Geremia et al. |
| 11,697,692 B2 | 7/2023 | Geremia et al. |
| 11,883,422 B2 | 1/2024 | von Maltzahn et al. |
| 2004/0235789 A1 | 11/2004 | Day et al. |
| 2005/0004070 A1 | 1/2005 | Stahl et al. |
| 2006/0257977 A1 | 11/2006 | Hamaker et al. |
| 2012/0220740 A1 | 8/2012 | Geremia et al. |
| 2012/0252957 A1 | 10/2012 | Geremia et al. |
| 2013/0023330 A1 | 1/2013 | Isaac et al. |
| 2013/0042859 A1 | 2/2013 | Geremia et al. |
| 2013/0337109 A1 | 12/2013 | Hamaguchi et al. |
| 2014/0060522 A1 | 3/2014 | Baynes et al. |

(Continued)

FOREIGN PATENT DOCUMENTS

| | | |
|---|---|---|
| CA | 1269483 A | 5/1990 |
| CN | 101784270 A | 7/2010 |

(Continued)

OTHER PUBLICATIONS

U.S. Appl. No. 16/761,107, filed May 1, 2020, Gibson et al.
PCT/US2019/047595, Feb. 12, 2020, International Search Report and Written Opinion.
PCT/US2019/047595, Mar. 4, 2021, International Preliminary Report on Partentability.
International Search Report and Written Opinion for Application No. PCT/US2019/047595, mailed Feb. 12, 2020.
International Preliminary Report on Patentabiliity for Application No. PCT/US2019/047595, mailed Mar. 4, 2021.

(Continued)

*Primary Examiner* — Jonathan S Lau
(74) *Attorney, Agent, or Firm* — Clark & Elbing LLP

(57) ABSTRACT

Aspects of the disclosure relate to oligosaccharide compositions and methods of making the same. Also provided are methods of using oligosaccharide compositions as microbiome metabolic therapies for reducing ammonia levels and for the treatment of hyperammonemia-related diseases (e.g., urea cycle disorders and hepatic encephalopathy).

15 Claims, 7 Drawing Sheets

(56) References Cited

U.S. PATENT DOCUMENTS

| | | |
|---|---|---|
| 2015/0202607 A1 | 7/2015 | Geremia et al. |
| 2015/0238948 A1 | 8/2015 | Geremia |
| 2016/0007642 A1 | 1/2016 | Geremia et al. |
| 2016/0032038 A1 | 2/2016 | Baynes et al. |
| 2016/0122447 A1 | 5/2016 | Geremia et al. |
| 2016/0213702 A1 | 7/2016 | von Maltzahn et al. |
| 2016/0366909 A1 | 12/2016 | Geremia et al. |
| 2017/0151268 A1 | 6/2017 | von Maltzahn et al. |
| 2017/0151269 A1 | 6/2017 | von Maltzahn et al. |
| 2017/0246201 A1 | 8/2017 | von Maltzahn et al. |
| 2018/0000145 A1 | 1/2018 | Geremia et al. |
| 2018/0000146 A1 | 1/2018 | Geremia |
| 2018/0037599 A1 | 2/2018 | Duflot et al. |
| 2018/0147221 A1 | 5/2018 | von Maltzahn et al. |
| 2018/0147222 A1 | 5/2018 | von Maltzahn et al. |
| 2018/0235987 A1 | 8/2018 | von Maltzahn et al. |
| 2018/0296582 A1 | 10/2018 | von Maltzahn et al. |
| 2019/0062468 A1 | 2/2019 | Geremia et al. |
| 2019/0091249 A1 | 3/2019 | von Maltzahn et al. |
| 2019/0290675 A1 | 9/2019 | Gibson et al. |
| 2019/0307159 A1 | 10/2019 | Geremia et al. |
| 2020/0000831 A1 | 1/2020 | Geremia et al. |
| 2020/0009168 A1 | 1/2020 | von Maltzahn et al. |
| 2020/0093845 A1 | 3/2020 | von Maltzahn et al. |
| 2020/0093851 A1 | 3/2020 | von Maltzahn et al. |
| 2020/0352980 A1 | 11/2020 | Mahowald et al. |
| 2020/0354481 A1 | 11/2020 | Geremia et al. |
| 2020/0390798 A1 | 12/2020 | Gibson et al. |
| 2021/0002387 A1 | 1/2021 | Geremia et al. |
| 2021/0076705 A1 | 3/2021 | Geremia et al. |
| 2021/0113596 A1 | 4/2021 | von Maltzahn et al. |
| 2021/0121486 A1 | 4/2021 | Geremia et al. |
| 2021/0137956 A1 | 5/2021 | von Maltzahn et al. |
| 2021/0137964 A1 | 5/2021 | von Maltzahn et al. |
| 2021/0161942 A1 | 6/2021 | von Maltzahn et al. |
| 2021/0164926 A1 | 6/2021 | Liu et al. |
| 2021/0198302 A1 | 7/2021 | Liu et al. |
| 2021/0352945 A1 | 11/2021 | Geremia |
| 2021/0401861 A1 | 12/2021 | von Maltzahn et al. |
| 2022/0233560 A1 | 7/2022 | Yatsunenko et al. |
| 2022/0233577 A1 | 7/2022 | Gibson et al. |
| 2022/0395521 A1 | 12/2022 | von Maltzahn et al. |
| 2022/0400728 A1 | 12/2022 | Geremia et al. |
| 2022/0409644 A1 | 12/2022 | Geremia et al. |
| 2023/0113218 A1 | 4/2023 | Mahowald et al. |
| 2023/0123695 A1 | 4/2023 | von Maltzahn et al. |
| 2023/0165881 A1 | 6/2023 | Lawrence et al. |
| 2023/0255240 A1 | 8/2023 | Geremia et al. |
| 2023/0255989 A1 | 8/2023 | von Maltzahn et al. |
| 2023/0277573 A1 | 9/2023 | Millet et al. |
| 2024/0108642 A1 | 4/2024 | von Maltzahn et al. |

FOREIGN PATENT DOCUMENTS

| | | |
|---|---|---|
| CN | 103619885 A | 3/2014 |
| EP | 2248907 A1 | 11/2010 |
| EP | 3862006 A1 | 8/2021 |
| JP | 2001-516388 A | 9/2001 |
| JP | 2012-525840 A | 10/2012 |
| JP | 2013-76044 A | 4/2013 |
| JP | 2017-522380 A | 8/2017 |
| WO | WO 1998/041544 A1 | 9/1998 |
| WO | WO-1998041545 A1 | 9/1998 |
| WO | WO 2004/052121 A1 | 6/2004 |
| WO | WO 2005/003329 A1 | 1/2005 |
| WO | WO-2009022007 A1 | 2/2009 |
| WO | WO 2009/082214 A1 | 7/2009 |
| WO | WO-2010128859 A2 | 11/2010 |
| WO | WO 2012/118767 A1 | 9/2012 |
| WO | WO-2013163230 A2 | 10/2013 |
| WO | WO 2014/031956 A1 | 2/2014 |
| WO | WO-2014/032004 A1 | 2/2014 |
| WO | WO-2014/159558 A1 | 10/2014 |
| WO | WO 2016/007778 A1 | 1/2016 |
| WO | WO 2016/122884 A1 | 8/2016 |
| WO | WO 2016/122885 A1 | 8/2016 |
| WO | WO-2016/122887 A1 | 8/2016 |
| WO | WO 2016/122889 A1 | 8/2016 |
| WO | WO-2016/122940 A1 | 8/2016 |
| WO | WO 2016/172657 A2 | 10/2016 |
| WO | WO 2016/172658 A2 | 10/2016 |
| WO | WO 2017/035412 A1 | 3/2017 |
| WO | WO-2017/083520 A1 | 5/2017 |
| WO | WO 2018/013871 A1 | 1/2018 |
| WO | WO 2018/106845 A1 | 6/2018 |
| WO | WO-2019014645 A1 | 1/2019 |
| WO | WO 2019/090181 A1 | 5/2019 |
| WO | WO-2019090180 A1 | 5/2019 |
| WO | WO-2019090182 A2 | 5/2019 |
| WO | WO-2020041531 A2 | 2/2020 |
| WO | WO-2020097568 A2 | 5/2020 |
| WO | WO-2020227689 A1 | 11/2020 |
| WO | WO-2021222660 A1 | 11/2021 |
| WO | WO-2022/016105 A1 | 1/2022 |
| WO | WO-2022/067131 A1 | 3/2022 |
| WO | WO-2023/059530 A1 | 4/2023 |
| WO | WO-2024/023198 A1 | 2/2024 |

OTHER PUBLICATIONS

Arn et al., Hyperammonemia in women with a mutation at the ornithine carbamoyltransferase locus. A cause of postpartum coma. N Engl J Med. Jun. 7, 1990;322(23):1652-5. doi: 10.1056/NEJM199006073222307.

Boltje et al., Opportunities and challenges in synthetic oligosaccharide and glycoconjugate research. Nat Chem. Nov. 2009;1(8):611-22. doi: 10.1038/nchem.399. Author Manuscript.

Braissant et al., Current concepts in the pathogenesis of urea cycle disorders. Mol Genet Metab. 2010;100 Suppl 1:S3-S12. doi: 10.1016/j.ymgme.2010.02.010. Epub Feb. 14, 2010.

Burton, Inborn errors of metabolism in infancy: a guide to diagnosis. Pediatrics. Dec. 1998;102(6):E69. doi: 10.1542/peds.102.6.e69.

Caporaso et al., Ultra-high-throughput microbial community analysis on the Illumina HiSeq and MiSeq platforms. ISME J. Aug. 2012;6(8):1621-4. doi: 10.1038/ismej.2012.8. Epub Mar. 8, 2012.

Cavicchi et al., Hypocitrullinemia in expanded newborn screening by LC-MS/MS is not a reliable marker for ornithine transcarbamylase deficiency. J Pharm Biomed Anal. Jul. 12, 2009;49(5):1292-5. doi: 10.1016/j.jpba.2009.03.001. Epub Mar. 20, 2009.

Cordwell et al., Exploring and exploiting bacterial proteomes. Methods Mol Biol. 2004;266:115-35. doi: 10.1385/1-59259-763-7:115.

Darmaun et al., Phenylbutyrate-induced glutamine depletion in humans: effect on leucine metabolism. Am J Physiol. May 1998;274(5):E801-7. doi: 10.1152/ajpendo.1998.274.5.E801.

De Preter et al., Effect of lactulose and Saccharomyces boulardii administration on the colonic urea-nitrogen metabolism and the bifidobacteria concentration in healthy human subjects. Aliment Pharmacol Ther. Apr. 1, 2006;23(7):963-74. doi: 10.1111/j.1365-2036.2006.02834.x.

De Souza et al., Recovery and purification of lactose from whey. Chem Eng Proc. 2010;49:1137-1143.

Díez-Municio et al, Synthesis of novel bioactive lactose-derived oligosaccharides by microbial glycoside hydrolases. Microb Biotechnol. Jul. 2014;7(4):315-31. doi: 10.1111/1751-7915.12124. Epub Apr. 1, 2014.

Gibson et al., Dietary modulation of the human colonic microbiota: introducing the concept of prebiotics. J Nutr. Jun. 1995;125(6):1401-12. doi: 10.1093/jn/125.6.1401.

Guerrero et al., Purification of highly concentrated galacto-oligosaccharide preparations by selective fermentation with yeasts. International Dairy Journal. Nov. 2014;39(1):78-88. doi.org/10.1016/j.idairyj.2014.05.011.

Heiss et al., The structure of Cryptococcus neoformans galactoxylomannan contains beta-D-glucuronic acid. Carbohydr Res. May 12, 2009;344(7):915-20. doi: 10.1016/j.carres.2009.03.003. Epub Mar. 10, 2009.

(56) References Cited

OTHER PUBLICATIONS

Huang et al., Tandem mass neonatal screening in Taiwan—report from one center. J Formos Med Assoc. Nov. 2006;105(11):882-6. doi: 10.1016/S0929-6646(09)60173-X.

Kailemia et al., Oligosaccharide analysis by mass spectrometry: a review of recent developments. Anal Chem. Jan. 7, 2014;86(1):196-212. doi: 10.1021/ac403969n. Epub Dec. 16, 2013. Author Manuscript. 31 pages.

Kuechel et al., Short communication: Development of a rapid laboratory method to polymerize lactose to nondigestible carbohydrates. J Dairy Sci. Apr. 2018;101(4):2862-2866. doi: 10.3168/jds.2017-13813. Epub Feb. 7, 2018.

Lee et al., In vivo urea cycle flux distinguishes and correlates with phenotypic severity in disorders of the urea cycle. Proc Natl Acad Sci U S A. Jul. 5, 2000;97(14):8021-6. doi: 10.1073/pnas.140082197.

Lundborg et al., Structure Analysis of Glycans by NMR Chemical Shift Prediction. Anal. Chem. 2011;83:1514-1517. Doi: 10.1021/ac1032534.

Maestri et al., The phenotype of ostensibly healthy women who are carriers for ornithine transcarbamylase deficiency. Medicine (Baltimore). Nov. 1998;77(6):389-97.

McCleary et al., Determination of insoluble, soluble, and total dietary fiber (CODEX definition) by enzymatic-gravimetric method and liquid chromatography: collaborative study. J AOAC Int. May-Jun. 2012;95(3):824-44. doi: 10.5740/jaoacint.cs2011_25.

McCleary et al., Determination of total dietary fiber (CODEX definition) by enzymatic-gravimetric method and liquid chromatography: collaborative study. J AOAC Int. Jan. Feb. 2010;93(1):221-33.

Miles et al., Hepatocyte glycogen accumulation in patients undergoing dietary management of urea cycle defects mimics storage disease. J Pediatr Gastroenterol Nutr. Apr. 2005;40(4):471-6. doi: 10.1097/01.mpg.0000157200.33486.ce.

Niroomand et al., Fate of bacterial pathogens and indicator organisms in liquid sweeteners. J Food Prot. Mar. 1998;61(3):295-9. doi: 10.4315/0362-028x-61.3.295.

Paik et al., Comparison of rifaximin and lactulose for the treatment of hepatic encephalopathy: a prospective randomized study. Yonsei Med J. Jun. 30, 2005;46(3):399-407. doi: 10.3349/ymj.2005.46.3.399.

Palframan et al., Development of a quantitative tool for the comparison of the prebiotic effect of dietary oligosaccharides. Lett Appl Microbiol. 2003;37(4):281-4. doi: 10.1046/j.1472-765x.2003.01398.x.

Pinelo et al., Membrane technology for purification of enzymatically produced oligosaccharides: Molecular and operational features affecting performance. Separation and Purification Technology. Nov. 19, 2009;70(1):1-11. doi.org/10.1016/j.seppur.2009.08.010.

Quinonez et al., Citrullinemia Type I. GeneReviews. Adam MP, Ardinger HH, Pagon RA, et al., editors. Seattle (WA): University of Washington, Seattle; 1993-2021. Retrieved from www.ncbi.nlm.nih.gov/books/NBK1458. Accessed on Jun. 14, 2011. 19 pages.

Romero-Gomez et al., Gut ammonia production and its modulation. Metab Brain Dis. Mar. 2009;24(1):147-57. doi: 10.1007/s11011-008-9124-3. Epub Dec. 10, 2008.

Sajilata et al., Resistant Starch—a Review. Compr Rev Food Sci Food Saf. Jan. 2006;5(1):1-17. doi: 10.1111/j.1541-4337.2006.tb00076.x.

Scaglia et al., Clinical consequences of urea cycle enzyme deficiencies and potential links to arginine and nitric oxide metabolism. J Nutr. Oct. 2004;134(10 Suppl):2775S-2782S; discussion 2796S-2797S. doi: 10.1093/jn/134.10.2775S.

Schaefer et al., Dialysis in neonates with inborn errors of metabolism. Nephrol Dial Transplant. Apr. 1999;14(4):910-8. doi: 10.1093/ndt/14.4.910.

Schulze et al., Lactose—ein potentieller Ballaststoff. Zur Regulierung ihrer mikroökologischen Wirksamkeit im Intestinaltrakt 3. Mitt. Ballaststoffwirkung der Lactose als Folge mikrobieller Aktivität [Lactose—a potential dietary fiber. The regulation of its microecologic effect in the intestinal tract. 3. Dietary fiber actions of lactose due to microbial activity]. Nahrung. 1991;35(9):903-20. German. doi: 10.1002/food.19910350902. Abstract only. 1 page.

Seeberger et al., Solid-phase oligosaccharide synthesis and combinatorial carbohydrate libraries. Chem Rev. Dec. 13, 2000;100(12):4349-94. doi: 10.1021/cr9903104.

Sen et al., Galactosyl oligosaccharide purification by ethanol precipitation. Food Chemistry. Oct. 1, 2011;128(3):773-777. doi.org/10.1016/j.foodchem.2011.03.076.

Sharma et al., Randomized controlled trial comparing lactulose plus albumin versus lactulose alone for treatment of hepatic encephalopathy. J Gastroenterol Hepatol. Jun. 2017;32(6):1234-1239. doi: 10.1111/jgh.13666.

Shchelochkov et al., High-frequency detection of deletions and variable rearrangements at the ornithine transcarbamylase (OTC) locus by oligonucleotide array CGH. Mol Genet Metab. Mar. 2009;96(3):97-105. doi: 10.1016/j.ymgme.2008.11.167. Epub Jan. 12, 2009.

Sreenath Nagamani et al., Argininosuccinate Lyase Deficiency. GeneReviews. Adam MP, Ardinger HH, Pagon RA, et al., editors. Seattle (WA): University of Washington, Seattle; 1993-2021. Retrieved from www.ncbi.nlm.nih.gov/books/NBK51784. Accessed on Jun. 14, 2011. 24 pages.

Summar et al., Current strategies for the management of neonatal urea cycle disorders. J Pediatr. Jan. 2001;138(1 Suppl):S30-9. doi: 10.1067/mpd.2001.111834.

Summar et al., Diagnosis, symptoms, frequency and mortality of 260 patients with urea cycle disorders from a 21-year, multicentre study of acute hyperammonaemic episodes. Acta Paediatr. Oct. 2008;97(10):1420-5. doi: 10.1111/j.1651-2227.2008.00952.x. Epub Jul. 17, 2008. Author Manuscript.

Summar et al., Proceedings of a consensus conference for the management of patients with urea cycle disorders. J Pediatr. Jan. 2001;138(1 Suppl):S6-10. doi: 10.1067/mpd.2001.111831.

Sun et al., Arginase Deficiency. GeneReviews. Adam MP, Ardinger HH, Pagon RA, et al., editors. Seattle (WA): University of Washington, Seattle; 1993-2021. Retrieved from ncbi.nlm.nih.gov/books/NBK1159. Accessed on Jun. 14, 2011. 23 pages.

Theriot et al., Antibiotic-induced shifts in the mouse gut microbiome and metabolome increase susceptibility to Clostridium difficile infection. Nat Commun. 2014;5:3114. doi: 10.1038/ncomms4114. Author Manuscript.

Titgemeyer et al., Fermentability of various fiber sources by human fecal bacteria in vitro. Am J Clin Nutr. Jun. 1991;53(6):1418-24. doi: 10.1093/ajcn/53.6.1418.

Tuchman et al., Blood levels of ammonia and nitrogen scavenging amino acids in patients with inherited hyperammonemia. Mol Genet Metab. Jan. 1999;66(1):10-5. doi: 10.1006/mgme.1998.2783.

Vanneste et al., Techno-economic evaluation of membrane cascades relative to simulated moving bed chromatography for the purification of mono- and oligosaccharides. Separation and Purification Technology. Aug. 18, 2011;80(3):600-609. doi.org/10.1016/j.seppur.2011.06.016.

Vera et al., Synthesis and purification of galacto-oligosaccharides: state of the art. World J Microbiol Biotechnol. Dec. 2016;32(12):197. doi: 10.1007/s11274-016-2159-4. Epub Oct. 18, 2016. 20 pages.

Wang et al., Naive Bayesian classifier for rapid assignment of rRNA sequences into the new bacterial taxonomy. Appl Environ Microbiol. Aug. 2007;73(16):5261-7. doi: 10.1128/AEM.00062-07. Epub Jun. 22, 2007.

Xiao et al., Chemical synthesis of polysaccharides and polysaccharide mimetics. Prog Poly Science. Nov. 2017;74:78-116. doi: 10.1016/j.progpolymsci.2017.07.009.

Zeuner et al., Methods for improving enzymatic trans-glycosylation for synthesis of human milk oligosaccharide biomimetics. J Agric Food Chem. Oct. 8, 2014;62(40):9615-31. doi: 10.1021/jf502619p. Epub Sep. 23, 2014.

Zhao et al., Rapid, sensitive structure analysis of oligosaccharides. Proc Natl Acad Sci U S A. Mar. 4, 1997;94(5):1629-33. doi: 10.1073/pnas.94.5.1629.

OLIGOSACCHARIDE COMPOSITIONS AND METHODS OF USE THEREOF FOR REDUCING AMMONIA LEVELS

RELATED APPLICATIONS

This application is a national stage filing under 35 U.S.C. § 371 of international application No. PCT/US2019/047595, filed Aug. 21, 2019, and claims the benefit of priority under 35 U.S.C. § 119(e) of U.S. Provisional Application No. 62/720,924, entitled "OLIGOSACCHARIDE COMPOSITIONS AND METHODS OF USE THEREOF FOR REDUCING AMMONIA LEVELS", filed Aug. 21, 2018; U.S. Provisional Application No. 62/755,461, entitled "OLIGOSACCHARIDE COMPOSITIONS AND METHODS OF USE THEREOF FOR REDUCING AMMONIA LEVELS", filed Nov. 3, 2018; U.S. Provisional Application No. 62/757,723, entitled "OLIGOSACCHARIDE COMPOSITIONS AND METHODS OF USE THEREOF FOR REDUCING AMMONIA LEVELS", filed Nov. 8, 2018; U.S. Provisional Application No. 62/845,295, entitled "OLIGOSACCHARIDE COMPOSITIONS AND METHODS OF USE THEREOF FOR REDUCING AMMONIA LEVELS", filed May 8, 2019; the contents of each of which are incorporated herein by reference in their entirety.

FIELD OF THE INVENTION

The present disclosure relates to oligosaccharide compositions and uses thereof.

BACKGROUND OF INVENTION

The gut microbiome, the ecosystem of about one hundred trillion ($1 \times 10^{14}$) microbial cells in the intestine, can be regarded as an important organ of the human body, responsible for functions that human cells cannot carry out independently. The gut microbiota play a key role in human health and disease by affecting nutrient utilization, colonization resistance, development of the immune system, modulation of the host metabolism, and other diverse aspects of the host's physiology. One example of the gut microbiota's contribution to the host's metabolic capabilities concerns nitrogen utilization. The colon is rich in nitrogen sources, which include mucin, urea, and dietary amino acids that have escaped host digestion. Some gut microbes can liberate ammonia from these molecules and incorporate this ammonia into bacterial biomolecules like proteins and nucleic acids. However, the amount of ammonia liberated often exceeds the metabolic requirements of these gut bacteria, which causes ammonia to accumulate in the gut. Under non-acidic conditions this ammonia diffuses across the gut epithelium into the portal circulation, potentially making a significant contribution to the elevated ammonia levels in hyperammonemic patients.

SUMMARY OF INVENTION

According to some aspects, provided herein are microbiome metabolic therapies utilizing oligosaccharide compositions that are useful for driving functional outputs of the gut microbiome organ, e.g., to treat disease and improve overall health. In some embodiments, such oligosaccharide compositions are particularly effective for reducing ammonia levels in a subject. Accordingly, in some embodiments, oligosaccharide compositions disclosed herein are useful for treating a subject having a disorder associated with hyperammonemia, such as urea cycle disorders and hepatic encephalopathy.

In one aspect, oligosaccharide compositions are provided that comprise a plurality of oligosaccharides that comprise Formula (I):

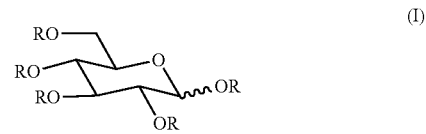

(I)

wherein R is independently selected from hydrogen, and Formulae (Ia), (Ib), (Ic), and (Id):

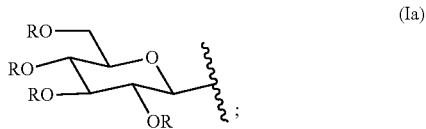

(Ia)

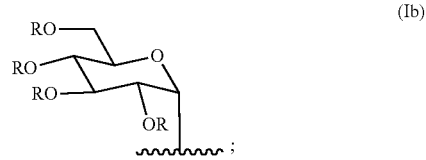

(Ib)

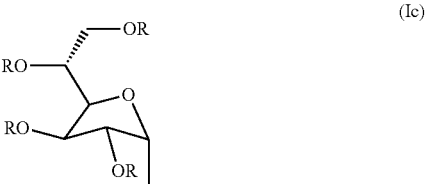

(Ic)

; and

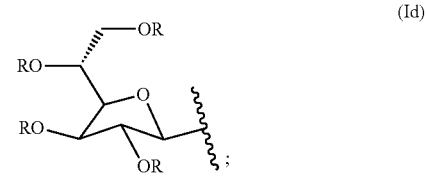

(Id)

wherein R is independently defined as above.

In some embodiments, oligosaccharide compositions are provided that comprise a plurality of oligosaccharides that comprise Formula (I):

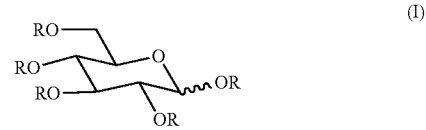

(I)

wherein R is selected from a group consisting essentially of: hydrogen, Formula (Ia), Formula (Ib), Formula (Ic), and Formula (Id):

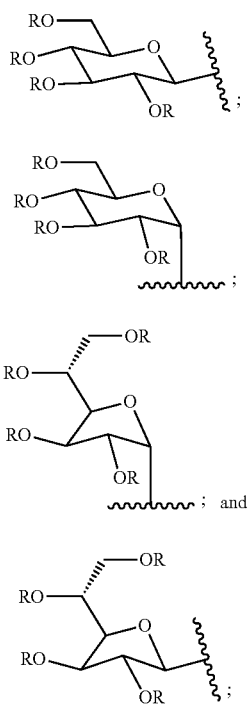

(Ia)

(Ib)

(Ic)

(Id)

wherein R is independently defined as above.

In some aspects, provided herein is an oligosaccharide composition comprising a plurality of oligosaccharides, the composition being characterized by a multiplicity-edited gradient-enhanced $^1$H-$^{13}$C heteronuclear single quantum coherence (HSQC) NMR spectrum comprising signals 1, 3, and 4, each signal having a center position and an area:

| Signal | Center Position (ppm) $^1$H | $^{13}$C | Area under the curve (AUC) (% of total areas of signals of Table 5) | Glycosidic Bond Type |
|---|---|---|---|---|
| 1 | 5.39 | 100.31 | 3.37-4.78 | alpha-1,4 |
| 3 | 5.35 | 99.77 | 6.64-8.71 | alpha-1,3 |
| 4 | 5.22 | 102.55 | 0.00-0.95 | — |

In some embodiments, signals 1, 3, and 4 are defined as follows:

| Signal | Center Position (ppm) $^1$H | $^{13}$C | Area under the curve (AUC) (% of total areas of signals of Table 5) | Glycosidic Bond Type |
|---|---|---|---|---|
| 1 | 5.39 | 100.31 | 3.84-4.08 | alpha-1,4 |
| 3 | 5.35 | 99.77 | 7.33-7.60 | alpha-1,3 |
| 4 | 5.22 | 102.55 | 0.23-0.40 | — |

In some embodiments, the NMR spectrum of the oligosaccharide composition further comprises 1-2 signals selected from signals 8 and 9, each signal having a center position and an area:

| Signal | Center Position (ppm) $^1$H | $^{13}$C | Area under the curve (AUC) (% of total areas of signals of Table 5) | Glycosidic Bond Type |
|---|---|---|---|---|
| 8 | 5.03 | 93.95 | 0.00-0.89 | — |
| 9 | 4.97 | 98.49 | 32.69-40.14 | alpha-1,6 |

In some embodiments, signals 8 and 9 are defined as follows:

| Signal | Center Position (ppm) $^1$H | $^{13}$C | Area under the curve (AUC) (% of total areas of signals of Table 5) | Glycosidic Bond Type |
|---|---|---|---|---|
| 8 | 5.03 | 93.95 | 0.20-0.28 | — |
| 9 | 4.97 | 98.49 | 35.19-36.30 | alpha-1,6 |

In some embodiments, the NMR spectrum of the oligosaccharide composition further comprises 1-6 signals selected from signals 6, 7, 11, 12, 13, and 14, each signal having a center position and an area:

| Signal | Center Position (ppm) $^1$H | $^{13}$C | Area under the curve (AUC) (% of total areas of signals of Table 5) | Glycosidic Bond Type |
|---|---|---|---|---|
| 6 | 5.17 | 96.06 | 0.26-1.55 | — |
| 7 | 5.1 | 96.77 | 0.65-2.30 | alpha-1,2-alpha |
| 11 | 4.71 | 103.64 | 6.78-8.16 | beta-1,3 |
| 12 | 4.64 | 103.54 | 1.23-3.20 | beta-1-alpha-1' |
| 13 | 4.63 | 104.53 | 1.80-3.09 | beta-1,2-alpha |
| 14 | 4.52 | 103.34 | 28.46-32.06 | beta-1,4/beta-1,6 co-peak |

In some embodiments, signals 6, 7, 11, 12, 13, and 14 are defined as follows:

| Signal | Center Position (ppm) $^1$H | $^{13}$C | Area under the curve (AUC) (% of total areas of signals of Table 5) | Glycosidic Bond Type |
|---|---|---|---|---|
| 6 | 5.17 | 96.06 | 0.69-0.96 | — |
| 7 | 5.1 | 96.77 | 1.21-1.48 | alpha-1,2-alpha |
| 11 | 4.71 | 103.64 | 7.25-7.50 | beta-1,3 |
| 12 | 4.64 | 103.54 | 1.92-2.24 | beta-1-alpha-1' |
| 13 | 4.63 | 104.53 | 2.22-2.50 | beta-1,2-alpha |
| 14 | 4.52 | 103.34 | 29.58-30.28 | beta-1,4/beta-1,6 co-peak |

In some embodiments, the NMR spectrum of the oligosaccharide composition further comprises signal 1-3 signals selected from signals 2, 5, and 10:

| Signal | Center Position (ppm) $^1$H | $^{13}$C | Area under the curve (AUC) (% of total areas of signals of Table 5) | Glycosidic Bond Type |
|---|---|---|---|---|
| 2 | 5.36 | 98.48 | 0.69-1.78 | alpha-1,2-beta |
| 5 | 5.19 | 93.95 | 1.56-4.45 | alpha-1-alpha-1' |
| 10 | 4.8 | 96.77 | 0.26-1.35 | beta-1,2-beta, reducing |

In some embodiments, signals 2, 5, and 10 are defined as follows:

| Signal | Center Position (ppm) $^1$H | Center Position (ppm) $^{13}$C | Area under the curve (AUC) (% of total areas of signals of Table 5) | Glycosidic Bond Type |
|---|---|---|---|---|
| 2 | 5.36 | 98.48 | 1.05-1.21 | alpha-1,2-beta |
| 5 | 5.19 | 93.95 | 2.47-2.98 | alpha-1-alpha-1' |
| 10 | 4.8 | 96.77 | 0.61-0.84 | beta-1,2-beta, reducing |

In some embodiments, signals 1-14 of the NMR spectrum of the oligosaccharide composition are further characterized by an $^1$H integral region and a $^{13}$C integral region, defined as follows:

| | $^1$H Position (ppm) | | | $^{13}$C Position (ppm) | | |
|---|---|---|---|---|---|---|
| | Center | $^1$H Integral Region | | Center | $^{13}$C Integral Region | |
| Signal | Position | from | to | Position | from | to |
| 1 | 5.39 | 5.4229 | 5.3620 | 100.31 | 99.9518 | 100.6747 |
| 2 | 5.36 | 5.3877 | 5.3310 | 98.48 | 98.2048 | 98.7590 |
| 3 | 5.35 | 5.3971 | 5.2958 | 99.77 | 99.3614 | 100.1807 |
| 4 | 5.22 | 5.2357 | 5.1994 | 102.55 | 102.1205 | 102.9759 |
| 5 | 5.19 | 5.2047 | 5.1684 | 93.95 | 93.6506 | 94.2530 |
| 6 | 5.17 | 5.1933 | 5.1540 | 96.06 | 95.7590 | 96.3614 |
| 7 | 5.1 | 5.1207 | 5.0772 | 96.77 | 96.5181 | 97.0120 |
| 8 | 5.03 | 5.0545 | 5.0009 | 109.19 | 108.7831 | 109.6024 |
| 9 | 4.97 | 5.0194 | 4.9173 | 98.49 | 97.8795 | 99.0964 |
| 10 | 4.8 | 4.8197 | 4.7827 | 96.77 | 96.5904 | 96.9518 |
| 11 | 4.71 | 4.7641 | 4.6658 | 103.64 | 103.2169 | 104.0723 |
| 12 | 4.64 | 4.6670 | 4.6193 | 103.54 | 103.1807 | 103.9036 |
| 13 | 4.63 | 4.6514 | 4.6008 | 104.53 | 104.2289 | 104.8313 |
| 14 | 4.52 | 4.5841 | 4.4476 | 103.34 | 102.8193 | 103.8675 |

In some embodiments, the NMR spectrum of the oligosaccharide composition is obtained by subjecting a sample of the composition to a multiplicity-edited gradient-enhanced $^1$H-$^{13}$C heteronuclear single quantum coherence (HSQC) experiment using an echo-antiecho scheme for coherence selection using the following pulse sequence diagram, acquisition parameters and processing parameters:

Pulse sequence diagram as shown in FIG. 6 having
Acquisition Parameters
 $^1$H Carrier Frequency=4 ppm
 $^{13}$C Carrier Frequency=65 ppm
 Number of points in acquisition dimension=596
 Spectral range in acquisition dimension=6.00 ppm to 2.03 ppm
 Number of points in indirect dimension=300 complex points
 Spectral range in indirect dimension=120 ppm to 10 ppm
 Recycle delay=1 second
 One-bond $^1$H-$^{13}$C coupling constant=$J_{CH}$=146 Hz
 Number of scans=8
 Temperature=298 K
 Solvent=D$_2$O
Processing Parameters
 Window function in direct dimension=Gaussian broadening, 7.66 Hz
 Window function in indirect dimension=Gaussian broadening 26.48 Hz
 Processing=512 complex points in direct dimension, 1024 complex points in indirect dimension In some embodiments, the NMR spectrum of the oligosaccharide composition is obtained by subjecting a sample of the composition to HSQC NMR, wherein the sample is a solution in D$_2$O.

In some embodiments, the mean degree of polymerization (DP) of the oligosaccharide composition is from about DP5 to about DP11. In some embodiments, the mean degree of polymerization (DP) of the oligosaccharide composition is from about DP4 to about DP8. In some embodiments, the mean degree of polymerization (DP) of the oligosaccharide composition is from about DP5 to about DP6.

In some embodiments, the composition comprises 16% to 24% dextrose equivalent (dry basis). In some embodiments, the composition comprises 13% to 27% dextrose equivalent (dry basis). In some embodiments, the composition comprises 50% to 95% total dietary fiber (dry basis). In some embodiments, the composition comprises at least 60%, 70%, 80%, or 90% total dietary fiber (dry basis).

In some aspects, provided herein is an oligosaccharide composition comprising a plurality of oligosaccharides, each oligosaccharide comprising a plurality of monomer radicals;
 the plurality of oligosaccharides comprising two or more types of monomer radicals selected from radicals (1)-(7), wherein the selected radicals are present in the plurality of oligosaccharides in the defined molar percentage (mol %) range:
  (1) 2-glucopyranose diradicals, representing 6.15-9.54 mol % of monomer radicals in the plurality of oligosaccharides;
  (2) 6-glucopyranose diradicals, representing 18.94-24.61 mol % of monomer radicals in the plurality of oligosaccharides;
  (3) 4-glucopyranose diradicals, representing 6.63-8.64 mol % of monomer radicals in the plurality of oligosaccharides;
  (4) 3,4-glucopyranose triradicals, representing less than 1.42 mol % of monomer radicals in the plurality of oligosaccharides;
  (5) 2,3-glucopyranose triradicals, representing at least 1.41 mol % of monomer radicals in the plurality of oligosaccharides;
  (6) 3,4,6-glucopyranose tetraradicals, representing 0.11-1.00 mol % of monomer radicals in the plurality of oligosaccharides; and
  (7) 2,4,6-glucopyranose tetraradicals, representing less than 0.72 mol % of monomer radicals in the plurality of oligosaccharides;
 wherein at least one of the two or more types of monomer radicals is (4), (5), or (7).

In some embodiments, at least one of the two or more types of monomer radicals is:
 (4) 3,4-glucopyranose triradicals, representing less than 1.42 mol % of monomer radicals in the plurality of oligosaccharides.

In some embodiments, at least one of the two or more types of monomer radicals is:
 (4) 3,4-glucopyranose triradicals, representing less than 1.22 mol % of monomer radicals in the plurality of oligosaccharides.

In some embodiments, at least one of the two or more types of monomer radicals is:
 (5) 2,3-glucopyranose triradicals, representing at least 1.41 mol % of monomer radicals in the plurality of oligosaccharides.

In some embodiments, at least one of the two or more types of monomer radicals is:
 (5) 2,3-glucopyranose triradicals, representing at least 1.54 mol % of monomer radicals in the plurality of oligosaccharides.

In some embodiments, at least one of the two or more types of monomer radicals is:
(7) 2,4,6-glucopyranose tetraradicals, representing less than 0.72 mol % of monomer radicals in the plurality of oligosaccharides.

In some embodiments, at least one of the two or more types of monomer radicals is:
(7) 2,4,6-glucopyranose tetraradicals, representing less than 0.64 mol % of monomer radicals in the plurality of oligosaccharides.

In some embodiments, the oligosaccharide composition comprises three, four, five, six, or seven types of monomer radicals selected from radicals (1)-(7).

In some embodiments, the oligosaccharide composition comprises two or three of the monomer radicals selected from radicals (4), (5), or (7).

In some embodiments, the oligosaccharide composition further comprises one or more types of monomer radicals selected from radicals (8)-(12):
(8) t-glucopyranose monoradicals, representing 26.87-46.98 mol % of monomer radicals in the plurality of oligosaccharides;
(9) 3-glucopyranose diradicals, representing 6.94-9.25 mol % of monomer radicals in the plurality of oligosaccharides;
(10) 2,4-glucopyranose triradicals, representing 0.64-1.43 mol % of monomer radicals in the plurality of oligosaccharides;
(11) 2,6-glucopyranose/4,6-glucopyranose triradicals, representing 5.09-9.66 mol % of monomer radicals in the plurality of oligosaccharides; and
(12) 2,3,4-glucopyranose radicals, representing 0.08-0.85 mol % of monomer radicals in the plurality of oligosaccharides.

In some embodiments, the oligosaccharide composition comprises one, two, three, four, or five types of monomer radicals selected from radicals (8)-(12).

In some embodiments, the oligosaccharide composition further comprises one or more types of monomer radicals selected from radicals (13)-(15):
(13) 3,6-glucopyranose triradicals, representing 2.35-6.01 mol % of monomer radicals in the plurality of oligosaccharides;
(14) 2,3,6-glucopyranose tetraradicals, representing 0.06-0.86 mol % of monomer radicals in the plurality of oligosaccharides; and
(15) 2,3,4,6-glucopyranose pentaradicals, representing less than 0.61 mol % of monomer radicals in the plurality of oligosaccharides.

In some embodiments, the oligosaccharide composition comprises one, two, or three types of monomer radicals selected from radicals (13)-(15).

In some embodiments, the oligosaccharide composition comprises radicals (1)-(15):
(1) 2-glucopyranose diradicals, representing 6.15-9.54 mol % of monomer radicals in the plurality of oligosaccharides;
(2) 6-glucopyranose diradicals, representing 18.94-24.61 mol % of monomer radicals in the plurality of oligosaccharides;
(3) 4-glucopyranose diradicals, representing 6.63-8.64 mol % of monomer radicals in the plurality of oligosaccharides;
(4) 3,4-glucopyranose triradicals, representing less than 1.42 mol % of monomer radicals in the plurality of oligosaccharides;
(5) 2,3-glucopyranose triradicals, representing 0.64-1.43 mol % of monomer radicals in the plurality of oligosaccharides;
(6) 3,4,6-glucopyranose tetraradicals, representing less than 0.72 mol % of monomer radicals in the plurality of oligosaccharides;
(7) 2,4,6-glucopyranose tetraradicals, representing less than 0.61 mol % of monomer radicals in the plurality of oligosaccharides;
(8) t-glucopyranose monoradicals, representing 26.87-46.98 mol % of monomer radicals in the plurality of oligosaccharides;
(9) 3-glucopyranose diradicals, representing 6.94-9.25 mol % of monomer radicals in the plurality of oligosaccharides;
(10) 2,4-glucopyranose triradicals, representing 0.64-1.43 mol % of monomer radicals in the plurality of oligosaccharides;
(11) 2,6-glucopyranose/4,6-glucopyranose triradicals, representing 5.09-9.66 mol % of monomer radicals in the plurality of oligosaccharides;
(12) 2,3,4-glucopyranose radicals, representing 0.08-0.85 mol % of monomer radicals in the plurality of oligosaccharides;
(13) 3,6-glucopyranose triradicals, representing 2.35-6.01 mol % of monomer radicals in the plurality of oligosaccharides;
(14) 2,3,6-glucopyranose tetraradicals, representing 0.06-0.86 mol % of monomer radicals in the plurality of oligosaccharides; and
(15) 2,3,4,6-glucopyranose pentaradicals, representing less than 0.61 mol % of monomer radicals in the plurality of oligosaccharides.

In some embodiments, the plurality of oligosaccharides comprises:
25-45 mol % glucopyranose monoradicals;
35-55 mol % glucopyranose diradicals;
10-25 mol % glucopyranose triradicals; and
0.5-5 mol % glucopyranose tetraradicals.

In some embodiments, the plurality of oligosaccharides comprises:
30-43 mol % glucopyranose monoradicals;
41-50 mol % glucopyranose diradicals;
12-19 mol % glucopyranose triradicals; and
0.8-3 mol % glucopyranose tetraradicals.

In some embodiments, an oligosaccharide composition comprises a plurality of oligosaccharides, each oligosaccharide comprising a plurality of monomer radicals;
the plurality of oligosaccharides comprising two or more types of monomer radicals selected from radicals (1)-(7), wherein the selected radicals are present in the plurality of oligosaccharides in a defined molar percentage (mol %) range:
(1) 2-glucopyranose diradicals, representing 6.15-9.54 mol % of monomer radicals in the plurality of oligosaccharides;
(2) 6-glucopyranose diradicals, representing at least 18.94 mol % of monomer radicals in the plurality of oligosaccharides;
(3) 4-glucopyranose diradicals, representing 6.63-8.74 mol % of monomer radicals in the plurality of oligosaccharides;
(4) 3,4-glucopyranose triradicals, representing less than 1.42 mol % of monomer radicals in the plurality of oligosaccharides;

(5) 2,3-glucopyranose triradicals, representing 1.01-2.59 mol % of monomer radicals in the plurality of oligosaccharides;
(6) 3,4,6-glucopyranose tetraradicals, representing less than 1.00 mol % of monomer radicals in the plurality of oligosaccharides; and
(7) 2,4,6-glucopyranose tetraradicals, representing less than 0.72 mol % of monomer radicals in the plurality of oligosaccharides;
wherein at least one of the two or more types of monomer radicals is (4) or (7).

In some embodiments, an oligosaccharide composition comprises a plurality of oligosaccharides, each oligosaccharide comprising a plurality of monomer radicals; the plurality of oligosaccharides comprising two or more (e.g., 2, 3, 4, 5, 6, 7, 8, 9, 10, 11, 12, 13, 14, or 15) types of monomer radicals selected from radicals (1)-(15), wherein the selected radicals are present in the plurality of oligosaccharides in the defined molar percentage (mol %) range:
(1) 2-glucopyranose diradicals, representing 6.15-9.54 mol % of monomer radicals in the plurality of oligosaccharides;
(2) 6-glucopyranose diradicals, representing at least 18.94 mol % of monomer radicals in the plurality of oligosaccharides;
(3) 4-glucopyranose diradicals, representing 6.63-8.74 mol % of monomer radicals in the plurality of oligosaccharides;
(4) 3,4-glucopyranose triradicals, representing less than 1.42 mol % of monomer radicals in the plurality of oligosaccharides;
(5) 2,3-glucopyranose triradicals, representing 1.01-2.59 mol % of monomer radicals in the plurality of oligosaccharides;
(6) 3,4,6-glucopyranose tetraradicals, representing less than 1.00 mol % of monomer radicals in the plurality of oligosaccharides;
(7) 2,4,6-glucopyranose tetraradicals, representing less than 0.72 mol % of monomer radicals in the plurality of oligosaccharides;
(8) t-glucopyranose monoradicals, representing 26.87-46.98 mol % of monomer radicals in the plurality of oligosaccharides;
(9) 3-glucopyranose diradicals, representing at least 6.94 mol % of monomer radicals in the plurality of oligosaccharides;
(10) 2,4-glucopyranose triradicals, representing less than 1.43 mol % of monomer radicals in the plurality of oligosaccharides;
(11) 2,6-glucopyranose/4,6-glucopyranose triradicals, representing less than 9.66 mol % of monomer radicals in the plurality of oligosaccharides;
(12) 2,3,4-glucopyranose radicals, representing 0.07-0.85 mol % of monomer radicals in the plurality of oligosaccharides
(13) 3,6-glucopyranose triradicals, representing 2.35-6.01 mol % of monomer radicals in the plurality of oligosaccharides;
(14) 2,3,6-glucopyranose tetraradicals, representing 0.06-0.86 mol % of monomer radicals in the plurality of oligosaccharides; and/or
(15) 2,3,4,6-glucopyranose pentaradicals, representing less than 0.61 mol % of monomer radicals in the plurality of oligosaccharides.

In some embodiments, the oligosaccharide composition comprises:
(4) 3,4-glucopyranose triradicals, representing less than 0.70 mol % of monomer radicals in the plurality of oligosaccharides.

In some embodiments, the oligosaccharide composition comprises:
(7) 2,4,6-glucopyranose tetraradicals, representing less than 0.50 mol % of monomer radicals in the plurality of oligosaccharides.

In some embodiments, the oligosaccharide composition comprises:
(6) 3,4,6-glucopyranose tetraradicals, representing less than 0.40 mol % of monomer radicals in the plurality of oligosaccharides 40. The composition of any one of claims 36-39. wherein the oligosaccharide composition comprises:
(8) t-glucopyranose monoradicals, representing 30.00-40.00 mol % of monomer radicals in the plurality of oligosaccharides.

In some embodiments, the oligosaccharide composition comprises:
(9) 3-glucopyranose diradicals, representing 6.94-9.25 mol % of monomer radicals in the plurality of oligosaccharides.

In some embodiments, the oligosaccharide composition comprises:
(9) 3-glucopyranose diradicals, representing at least 9.10 mol % of monomer radicals in the plurality of oligosaccharides.

In some embodiments, the oligosaccharide composition comprises:
(10) 2,4-glucopyranose triradicals, representing less than 1.10 mol % of monomer radicals in the plurality of oligosaccharides.

In some embodiments, the oligosaccharide composition comprises:
(11) 2,6-glucopyranose/4,6-glucopyranose triradicals, representing less than 6.00 mol % of monomer radicals in the plurality of oligosaccharides;

In some embodiments, the oligosaccharide composition comprises:
(15) 2,3,4,6-glucopyranose pentaradicals, representing less than 0.10 mol % of monomer radicals in the plurality of oligosaccharides.

In some embodiments, the molar percentages of monomer radicals are determined using a permethylation assay, wherein the permethylation assay comprises the use of gas chromatography-mass spectroscopy (GC-MS) analysis, optionally wherein a sample comprising a composition is analyzed by GC-MS while heating at a rate of 4° C./min from 170° C. to 240° C. over a period of 20.0 minutes.

In some aspects, provided herein is an oligosaccharide composition comprising a plurality of oligosaccharides that comprise Formula (I):

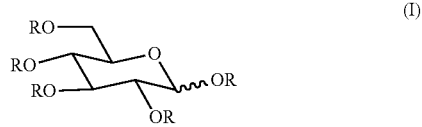

wherein R is independently selected from hydrogen, and Formulae (Ia), (Ib), (Ic), and (Id):

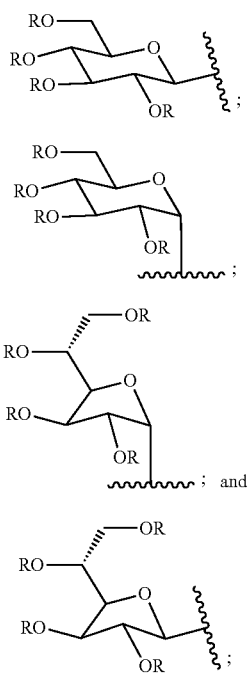

wherein R in Formulae (Ia), (Ib), (Ic), and (Id) is independently defined as above in Formula (I); wherein the composition is produced by a process comprising:
(a) forming a reaction mixture comprising a dextrose preparation with a catalyst comprising acidic protons; and
(b) promoting acid catalyzed oligosaccharide formation in the reaction mixture by transferring sufficient heat to the reaction mixture to maintain the reaction mixture at its boiling point until the molar ratio of net water condensate produced by the reaction mixture relative to total dextrose in the dextrose preparation prior to loading in (a) is in a range of 0.35-1.0, wherein the reaction mixture is maintained at a pressure in a range of 0.5-1.5 atm.

In some embodiments, the process further comprises:
(c) quenching the reaction mixture using water while bringing the temperature of the reaction mixture to 100° C. or below.

In some embodiments, the process further comprises:
(d) separating at least a portion of the oligosaccharides from the acid catalyst.

In some embodiments, the acid catalyst is a solid substrate that comprises acidic protons. An acid catalyst may be a strong acid cation exchange resin having one or more physical and chemical properties according to Table 1 and/or wherein the catalyst comprises >3.0 mmol/g sulfonic acid moieties and <1.0 mmol/gram cationic moieties. In some embodiments, the catalyst has a nominal moisture content of 45-50 weight percent.

In some embodiments, in step (a), the acid catalyst is present in an amount such that the molar ratio of acidic protons to dextrose is in a range of 0.001-0.25. In some embodiments, in step (a), the acid catalyst is present in an amount such that the molar ratio of acidic protons to dextrose is in a range of 0.0016-0.022.

In some embodiments, in step (a), the dextrose preparation comprises dextrose monomer. In some embodiments, in step (a), the dextrose preparation comprises dextrose monohydrate or 70DS corn syrup.

In some embodiments, the plurality of oligosaccharides that comprise Formula (I) comprises at least 60%, at least 70%, at least 80%, or at least 90% of the total oligosaccharide composition. In some embodiments, the plurality of oligosaccharides that comprise Formula (I) comprises at least 95% of the total oligosaccharide composition. In some embodiments, the plurality of oligosaccharides that comprise Formula (I) comprises at least 98% of the total oligosaccharide composition. In some embodiments, the plurality of oligosaccharides that comprise Formula (I) comprises 100% of the total oligosaccharide composition.

In some embodiments, no more than 1%, 2%, 3%, 5%, 7%, or 10% of monomers of the oligosaccharide composition are different from Formula (I) or Formulae Ia, Ib, Ic, and Id.

In some embodiments, no more than 1% of monomers of the oligosaccharide composition are different from Formula (I) or Formulae Ia, Ib, Ic, and Id. In some embodiments, no more than 5% of monomers of the oligosaccharide composition are different from Formula (I) or Formulae Ia, Ib, Ic, and Id. In some embodiments, monomers of the oligosaccharide composition that are different from Formula (I) or Formulae Ia, Ib, Ic, and Id comprise derivatized or chemically altered (e.g., degraded) sugar units (e.g., anhydro-forms).

In some embodiments, the reaction mixture is maintained at its boiling point until the molar ratio of net water condensate produced by the reaction mixture relative to total dextrose in the dextrose preparation prior to loading in (a) is in a range of 0.40-0.90.

In some embodiments, prior to step (b), the temperature of the reaction mixture is gradually increased from room temperature to the boiling point of the reaction mixture under suitable conditions to achieve homogeneity and uniform heat transfer.

In some embodiments, the reaction mixture comprises less than 1% sorbitol. In some embodiments, the oligosaccharide composition comprises less than 0.1% sorbitol. In some embodiments, the oligosaccharide composition comprises at least 90%, 95%, or 99% dextrose.

In some embodiments, the mean degree of polymerization (DP) of the oligosaccharide composition is from about DP4 to about DP8. In some embodiments, the mean degree of polymerization (DP) of the oligosaccharide composition is from about DP5 to about DP6.

In some embodiments, step (b) further comprises removing water from the reaction mixture by evaporation. In some embodiments, in step (c) the water is deionized water (at a temperature of about 60-100° C.). In some embodiments, in step (c) the water is added to the reaction mixture under conditions sufficient to avoid solidifying the mixture. In some embodiments, in step (d) said separating comprises removing the catalyst by filtration. In some embodiments, step (d) comprises cooling the reaction mixture to below about 85° C. before filtering.

In some embodiments, the process further comprises diluting the oligosaccharide composition of (d) with deionized water to a concentration of about 5-65 weight percent. In some embodiments, the process further comprises one or more (e.g., two or more, or three) of steps (e) to (g):
(e) passing the diluted composition through a cationic exchange resin;
(f) passing the diluted composition through an anionic exchange resin; and
(g) passing the diluted composition through a decolorizing polymer resin;

wherein each of (e), (f), and (g) can be performed one or more times in any order.

In some embodiments, the composition comprises total water content at a level below that which is necessary for microbial growth upon storage at room temperature. In some embodiments, the composition comprises total water content in a range of 24-33 weight percent.

In some embodiments, the oligosaccharides in the composition have a MWw (g/mol) in a range of 852-1475. In some embodiments, the oligosaccharides in the composition have a MWw (g/mol) in a range of 855-1100. In some embodiments, the oligosaccharides in the composition have a MWn (g/mol) in a range of 612-912. In some embodiments, the oligosaccharides in the composition have a MWw (g/mol) in a range of 612-710.

In some embodiments, the oligosaccharide composition has a pH in a range of 2.5-7.5. In some embodiments, the oligosaccharide composition has a pH in a range of 2.5-5.0.

In some embodiments, the oligosaccharide composition comprises oligomers having two or more monomers (DP2+) from about 75 to about 95 weight percent (dry basis). In some embodiments, the composition comprises oligomers having a degree of polymerization of two or more monomers (DP2+) from about 80 to about 90 weight percent (dry basis). In some embodiments, the oligosaccharide composition comprises less than 25%, less than 15%, or less than 3% or less than 1% monomer.

In some embodiments, the oligosaccharide composition comprises less than 3% w/w impurities. In some embodiments, the oligosaccharide composition is substantially non-absorbable in a human. In some embodiments, the oligosaccharide composition is minimally digestible by a human.

In some embodiments, the oligosaccharide composition comprises 16% to 24% dextrose equivalent (dry basis). In some embodiments, the oligosaccharide composition comprises 13% to 27% dextrose equivalent (dry basis). In some embodiments, the oligosaccharide composition comprises at least 70%, at least 80%, at least 90% total dietary fiber (dry basis). In some embodiments, the oligosaccharide composition comprises 65% to 95% total dietary fiber (dry basis).

In some embodiments, the composition does not contain detectable quantities of soluble dietary fiber precipitate (SDFP), insoluble dietary fiber (IDF), and/or high molecular weight dietary fiber (HMWDF).

In some aspects, provided herein are methods of reducing ammonia levels in a human subject. In some embodiments, method of reducing ammonia levels in a human subject comprise administering to the human subject an effective amount of an oligosaccharide composition described herein.

In some embodiments, the ammonia levels are systemic ammonia levels in the human subject. In some embodiments, ammonia levels are reduced by at least 20% compared to the ammonia levels prior to treatment.

In some embodiments, the subject has or has been diagnosed as having a urea cycle disorder. In some embodiments, the subject is of a pediatric population.

In some aspects, provided herein are methods of treating an urea cycle disorder (UCD) in a human subject, comprising administering to the subject an effective amount of an oligosaccharide composition described herein.

In some embodiments, the subject is of a pediatric population. In some embodiments, the human subject is at least 2 years of age. In some embodiments, the human subject is at least 2 months of age.

In some embodiments, the human subject has hepatic encephalopathy (HE).

In some aspects, provided herein are methods of treating a human subject who has or has been diagnosed as having liver cirrhosis, comprising administering to the human subject an oligosaccharide composition described herein.

In some embodiments, the subject has or has been diagnosed as having decompensated liver cirrhosis. In some embodiments, the subject has or has been diagnosed as having over hepatic encephalopathy (OHE). In some embodiments, the subject has or is being treated with lactulose and/or Xifaxin.

In some aspects, provided herein are methods of producing a oligosaccharide composition comprising a plurality of oligosaccharides, the method comprising:
(a) heating a dextrose preparation comprising dextrose monomer, under agitation conditions, to a temperature in a range of 120° C. to 145° C.;
(b) forming a reaction mixture comprising a dextrose preparation comprising dextrose monomer with a catalyst comprising acidic protons, wherein the molar ratio of acidic protons to dextrose monomer is in a range of 0.001-0.25; and
(c) promoting acid catalyzed oligosaccharide formation in the reaction mixture by transferring sufficient heat to the reaction mixture to maintain the reaction mixture at its boiling point until the weight percent of dextrose monomer in the reaction mixture is less than 30%, wherein the reaction mixture is maintained at a pressure in a range of 0.5-1.5 atm.

In some embodiments, the method further comprises:
(d) quenching the reaction mixture using water while bringing the temperature of the reaction mixture to 100° C. or below; and
(e) separating oligosaccharides from the acid catalyst.

In some embodiments, in step (a), the acid catalyst is present in an amount such that the molar ratio of acidic protons to dextrose is in a range of 0.0016-0.022.

In some embodiments, the reaction mixture is maintained at its boiling point until the weight percent of dextrose monomer in the reaction mixture is less than 25% (e.g., less than 20%, less than 15%, less than 10%). In some embodiments, the reaction mixture is maintained at its boiling point until the weight percent of dextrose monomer in the reaction mixture is in a range of 13-18%.

In some embodiments, the oligosaccharide composition is produced by a process comprising: (a) forming a reaction mixture comprising a dextrose preparation with a catalyst comprising acidic protons; and (b) promoting acid catalyzed oligosaccharide formation in the reaction mixture by transferring sufficient heat to the reaction mixture to maintain the reaction mixture at its boiling point until the weight percent of dextrose monomer in the reaction mixture is less than 30%, wherein the reaction mixture is maintained at a pressure in a range of 0.5-1.5 atm.

In some embodiments, the oligosaccharide composition comprises <10% sorbitol, e.g., about 10%, about 8%, about 6%, about 4%, about 2%, about 1% sorbitol, or about 0.1% or less sorbitol. In some embodiments, the reaction mixture comprises >90% glucose, e.g., about 95%, about 99%, or about 100% glucose. In some embodiments, the reaction mixture comprises <10% sorbitol and greater than 90% glucose, e.g., <1% sorbitol and greater than 99% glucose.

In some embodiments, the oligosaccharide composition comprises <10% sorbitol, e.g., about 10%, about 8%, about 6%, about 4%, about 2%, about 1% sorbitol, or about 0.1% or less sorbitol. In some embodiments, the oligosaccharide composition comprises <1% sorbitol, e.g., about 0.9%, about 0.5%, or about 0.1% sorbitol. In certain embodiments, the oligosaccharide composition comprises <0.1% sorbitol. In some embodiments, the oligosaccharide composition comprises >90% glucose, e.g., about 95%, about 99%, or about 100% glucose. In some embodiments, the oligosaccharide composition comprises <10% sorbitol and greater than 90% glucose, e.g., <1% sorbitol and greater than 99% glucose. In some embodiments, the mean degree of polymerization of all oligosaccharides is in a range of 5-6. In other embodiments, the mean degree of polymerization of all oligosaccharides is in a range of 4-9.

In some embodiments, the dextrose preparation comprises dextrose monohydrate or corn syrup, e.g., 70DS corn syrup. In some embodiments, heating a dextrose preparation comprises melting the dextrose preparation and/or heating the dextrose preparation under suitable conditions to achieve homogeneity and uniform heat transfer.

In some embodiments, the catalyst is a strong acid cation exchange resin having physical and chemical properties according to the following table:

TABLE 1

Non-Limiting Example of Strong Acid Cation Exchange Resin Properties

| Physical Form | | Amber translucent spherical beads |
|---|---|---|
| Matrix | | Styrene-DVB, gel |
| Function group | | Sulfonic acid |
| Ionic form as shipped | | H+ form |
| Total volume capacity, min. | eq/L | 1.8 |
| | kgr/ft³ as CaCO₃ | 39.3 |
| Moisture retention capacity | % | 50-56 |
| Particle size | | |
| Uniformity coefficient, max. | | 1.1 |
| Harmonic mean diameter | μm | 600 ± 50 |
| Whole uncracked beads | % | 95-100 |
| Total swelling (Na+ → H+) | % | 8 |
| Particle density | g/mL | 1.2 |
| Shipping density | g/L | 800 |
| | lbs/ft³ | 50 |

In some embodiments, the catalyst comprises >3.0 mmol/g sulfonic acid moieties and <1.0 mmol/gram cationic moieties. In some embodiments, the catalyst has a nominal moisture content of 45-50 weight percent.

In some embodiments, oligosaccharide composition is prepared by gradually increasing the temperature to about 130° C., under suitable conditions to achieve homogeneity and uniform heat transfer. In some embodiments, water is removed from the reaction mixture by evaporation. In some embodiments, the reaction mixture is maintained at 93-94 weight percent dissolved solids.

In some embodiments, the water is deionized water. In some embodiments, the water has a temperature of about 60-100° C. In some embodiments, the water is added to the reaction mixture under conditions sufficient to avoid solidifying the mixture. In some embodiments, separating comprises removing the catalyst by filtration. In some embodiments, the reaction mixture is cooled to below about 85° C. before filtering.

In some embodiments, the process of preparing an oligosaccharide composition further comprises: (f) diluting the oligosaccharide composition of (e) with, e.g., deionized water to a concentration of about 5-65 weight percent and passing the diluted composition through a cationic exchange resin; (g) passing the diluted composition through an anionic exchange resin; and (h) passing the diluted composition through a decolorizing polymer resin. In some embodiments, each of (f), (g), and (h) can be performed one or more times in any order.

In some embodiments, the oligosaccharide composition further comprises water at a level below that which is necessary for microbial growth upon storage at room temperature. In some embodiments, the oligosaccharide composition comprises water in a range of 24-33 weight percent. Methods for controlling moisture levels to address microbial growth are described in Ergun, R. et al, "Moisture and Shelf Life in Sugar Confections, Critical Reviews in Food Science and Nutrition", 2010, 50:2, 162-192; and NIROOMAND, F. et al. "Fate of Bacterial Pathogens and Indicator Organisms in Liquid Sweeteners" Journal of Food Protection, Vol. 61, No. 3, 1998, Pages 295-299; the contents of each are incorporated in their entirety.

In some embodiments, the oligosaccharide composition comprises oligosaccharides that have a MWw (weight-average molecular weight) (g/mol) in a range of 852-1475. In some embodiments, the oligosaccharide composition comprises oligosaccharides that have a MWn (number-average molecular weight) (g/mol) in a range of 612-912. In some embodiments, the oligosaccharide composition has a pH in a range of 3.0-7.5. In some embodiments, the oligosaccharide composition comprises oligomers having two or more monomers (DP2+) in a range of 83-86 weight percent. In some embodiments, the oligosaccharide composition comprises oligomers having two or more monomers (DP2+) in a range of 80-99 weight percent. In some embodiments, the oligosaccharide composition is substantially non-absorbable by a human (e.g., the oligosaccharide composition is not substantially absorbed by the stomach or intestines).

In one aspect, oligosaccharide compositions are provided herein that comprise oligosaccharides of the Formula (I):

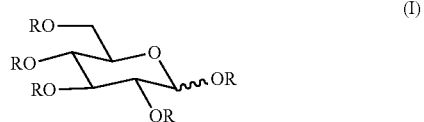

(I)

in which each R independently is selected from hydrogen, and Formulae (Ia), (Ib), (Ic), and (Id):

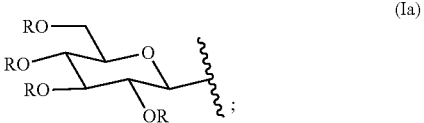

(Ia)

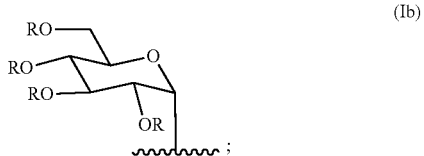

(Ib)

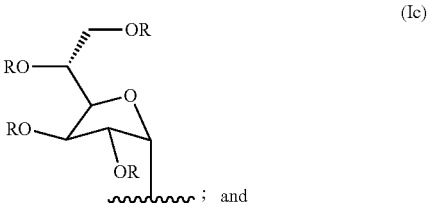

(Ic)

; and

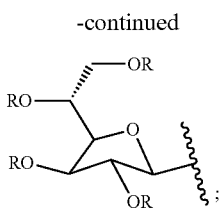

(Id)

in which each R independently is as defined above, and in which:
 i) the average degree of branching (DB) of the oligosaccharides is between 0.1 and 0.4;
 ii) 45% to 55% of the oligosaccharides have a degree of polymerization (DP) of at least 3 and less than or equal to 10 glycan units;
 iii) the average degree of polymerization (DP) (mean DP) of oligosaccharides is between about 5 and 8;
 iv) the ratio of alpha- to beta-glycosidic bonds present in the oligosaccharides of the composition is between about 1:1 to about 1.5:1 or 1:1 to about 3:1;
 v) the oligosaccharide composition comprises between 20 mol % and 60 mol % 1,6 glycosidic bonds;
 vi) the oligosaccharide composition comprises between 5 mol % and 25 mol % of at least one, two, or three of 1,2; 1,3; and 1,4 glycosidic bonds;
 vii) the oligosaccharide composition has a final solubility limit in water of at least about 70 Brix at 23° C.; and
 viii) the oligosaccharide composition has a dietary fiber content of at least 70%.

In another aspect, the present disclosure features a method of reducing ammonia levels in a human subject, comprising: administering to the human subject an oligosaccharide composition as described herein.

In some embodiments, the ammonia levels are systemic ammonia levels in the human subject. In some embodiments, the reduction in ammonia levels is measured in the blood. In some embodiments, the reduction in ammonia levels includes reduction of ammonia levels in cerebrospinal fluid. In some embodiments, the reduction in ammonia levels (e.g., systemic ammonia levels or blood ammonia levels) is a reduction of at least about 5%, 10%, 15%, or at least about 20% relative to the ammonia levels in the human subject prior to administration of the oligosaccharide composition. In some embodiments, the reduction in ammonia levels (e.g., systemic ammonia levels) is a reduction of at least about 5%, 10%, 15%, or at least about 20% relative to the ammonia levels in a healthy human subject. In some embodiments, the reduction in ammonia levels (e.g., systemic ammonia levels or blood ammonia levels) is a reduction of at least about 5%, 10%, 15%, or at least about 20% relative to the average ammonia levels in a population of human subjects (e.g., a population of healthy human subjects). In some embodiments, the reduction in ammonia levels is that of microbially-derived ammonia levels. In some embodiments, the reduction in ammonia levels (e.g., microbially-derived ammonia levels (e.g., in the gut)) is at least about 10%, 20%, or at least about 30% relative to the ammonia levels in the human subject prior to administration of the oligosaccharide composition. In some embodiments, the reduction in ammonia levels (e.g., microbially-derived ammonia levels (e.g., in the gut)) is at least about 10%, 20%, or at least about 30% relative to the ammonia levels in a healthy human subject. In some embodiments, the reduction in ammonia levels (e.g., microbially-derived ammonia levels (e.g., in the gut)) is at least about 10%, 20%, or at least about 30% relative to the ammonia levels in a population of human subjects (e.g., a population of healthy human subjects).

In another aspect, the present disclosure features a method for treating an urea cycle disorder (UCD) (e.g., carbamyl phosphate synthetase I (CPSI) deficiency, ornithine transcarbamylase (OTC) deficiency, argininosuccinate synthetase (ASS) deficiency, argininosuccinate lyase (ASL) deficiency, N-acetyl glutamate synthetase (NAGS) deficiency, arginase deficiency, ornithine translocase deficiency (HHH), or citrin deficiency(CIT II)) in a subject, e.g., a human subject, comprising: administering to the subject an oligosaccharide composition as described herein. In some embodiments, UCD does not include N-acetyl glutamate synthetase (NAGS) deficiency.

In some embodiments, administering an oligosaccharide composition to a subject having UCD reduces the risk, severity and/or frequency of a hyperammonemic crisis (e.g., when compared to a subject (including the same subject) who is not administered the oligosaccharide composition). In some embodiments, the subject is on a low protein or other supplemented diet. In some embodiments, the subject is concurrently treated with glycerol phenylbutyrate (e.g., Ravicti) (or a similar nitrogen scavenger therapy). In some embodiments, the subject is on a low protein or other supplemented diet and is being concurrently treated with glycerol phenylbutyrate (e.g., Ravicti) (or a similar nitrogen scavenger therapy). In some embodiments, the subject does not respond to treatment with a nitrogen scavenger (e.g., glycerol phenylbutyrate). In some embodiments, the subject is an infant, child, or young adult. In some embodiments, the subject has not (yet) received a liver transplant. In some embodiments, the subject has a urea cycle disorder (UCD) (e.g., carbamyl phosphate synthetase I (CPSI) deficiency, ornithine transcarbamylase (OTC) deficiency, argininosuccinate synthetase (ASS) deficiency, argininosuccinate lyase (ASL) deficiency, N-acetyl glutamate synthetase (NAGS) deficiency, or arginase deficiency, ornithine translocase deficiency (HHH), or citrin (CIT II) deficiency. In some embodiments, a UCD in a subject, e.g., a chronic UCD, is treated by administering an oligosaccharide composition described herein for a duration of at least 1 year, e.g., 1 year, 5 years, 10 years, 20 years, 50 years, or for life. In some embodiments, the oligosaccharide composition can be used as described in Examples 3 and 4.

In some embodiments, a human subject is at least 2 years of age. In some embodiments, the human subject is at least 2 months of age.

In some embodiments, the human subject is administered a nitrogen-scavenger therapy. In some embodiments, the human subject is administered a restricted diet (e.g., dietary restrictions on protein intake). In some embodiments, administration of the oligosaccharide dietary restrictions on protein intake can be liberated (e.g., the number or quantity of amino acid intake is increased). In some embodiments, the subject is poorly controlled with nitrogen-scavenger therapy (e.g., as determined by, e.g., i) the average level of ammonia in the subject's circulation; and/or ii) the number of ammonia crises experienced by the subject). In some embodiments, the subject exhibits systemic ammonia levels persistently above 0.5 upper limit of normal.

In some embodiments, one or both of the following is reduced: i) the number of ammonia crises over a period of 1 year (e.g., by at least 1, 2, or at least 3 crises), ii) the severity of complications from ammonia crises, including neurodevelopmental delays and/or cognitive declines (e.g., compared to a suitable control group not receiving the oligosaccharide composition). In some embodiments, the time period between ammonia crises is increased, e.g., by at least 15%, 30%, 60%, 100%, or 200% (e.g., compared to a suitable control group not receiving the oligosaccharide).

In another aspect, the present disclosure features a method for treating hepatic encephalopathy (HE) (e.g., overt HE (OHE) or minimal HE (MHE).

In some embodiments, methods are provided for treating a human subject who has or has been diagnosed as having liver cirrhosis. In some embodiments, the method comprise administering to the human subject an oligosaccharide composition as disclosed herein. In some embodiments, the subject has or has been diagnosed as having decompensated liver cirrhosis. In some embodiments, the subject has or has been diagnosed as having overt hepatic encephalopathy (OHE). In some embodiments, the subject has or is being treated with lactulose and/or Xifaxin. In some embodiments, the subject has been determined (e.g., by a physician) to benefit from or to be a candidate for such treatment based on one or more neuropsychiatric tests and/or a diagnosis of advance liver disease.

In some embodiments, administering an oligosaccharide composition to a subject having HE reduces the risk for and/or recurrence of HE (e.g., severity and/or frequency of HE), e.g., when compared to a subject (including the same subject) who is not administered the oligosaccharide composition. In some embodiments, the subject is concurrently treated with lactulose. In some embodiments, the subject is concurrently treated with rifaximin. In some embodiments, the subject has been treated with lactulose prior to administering an oligosaccharide composition. In some embodiments, the subject has been treated with rifaximin prior to administering an oligosaccharide composition. In some embodiments, the subject has been treated with lactulose and rifaximin prior to administering an oligosaccharide composition.

In some embodiments, the subject has or has been diagnosed with overt hepatic encephalopathy (OHE). In some embodiments, the subject has not (yet) been treated for HE (e.g., prior to administering an oligosaccharide composition). In some embodiments, the subject has minimal hepatic encephalopathy (MHE) and, in some embodiments, the subject is largely non-symptomatic (e.g., for OHE symptoms).

In some embodiments, a subject having hyperammonemia is suffering from hepatic encephalopathy (HE). In some embodiments, hyperammonemia is caused by or associated with, at least in part, alcohol and/or alcoholic cirrhosis, autoimmune hepatitis, chronic hepatitis B, or chronic hepatitis C, fatty liver, hepatitis C., hepatitis C and alcohol, iron overload and steatosis, nonalcoholic steatohepatitis, nonalcoholic steatohepatitis and hepatitis B, or primary biliary cirrhosis. In some embodiments, a subject having hyperammonemia has been previously treated or administered with lactulose or rifaximin. In some embodiments, a subject the subject is an adult (e.g., 20-64 years), or an elderly adult (e.g., 65 years and older). In some embodiments, HE in a subject, e.g., a chronic HE, is treated by administering an oligosaccharide composition described herein for a duration of at least 1 year (e.g., for a duration of 1 year, 5 years, 10 years, 20 years, 50 years, or for life). In some embodiments, the HE is overt hepatic encephalopathy (OHE). In some embodiments, the HE is minimal hepatic encephalopathy (MHE). In some embodiments, the oligosaccharide composition can be used as described in Example 2.

In another aspect, the present disclosure features a method of producing an oligosaccharide composition comprising a plurality of oligosaccharides that are minimally digestible by humans. In some embodiments, the method comprises: (a) heating a dextrose preparation comprising dextrose monomer, under agitation conditions, to a temperature in a range of 120° C. to 135° C.; (b) loading the dextrose preparation with a solid catalyst comprising acidic protons, in an amount such that the molar ratio of acidic protons to dextrose monomer is in a range of 0.016-0.022, thereby forming a reaction mixture; and (c) maintaining the reaction mixture at atmospheric pressure, at a temperature in a range of 120° C. to 135° C., under conditions that promote acid catalyzed oligosaccharide formation, until the weight percent of dextrose monomer in the composition is in a range of 14-17; (d) quenching the reaction mixture using water while bringing the temperature of the reaction mixture to 100° C. or below; and optionally (e) separating oligosaccharides from the acid catalyst; thereby obtaining the oligosaccharide composition.

In some embodiments, oligosaccharide compositions are provided herein that comprise a plurality of oligosaccharides that are minimally digestible in humans and that comprise Formula (I):

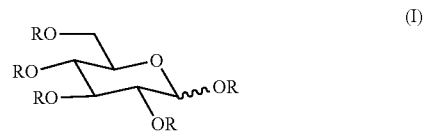
(I)

in which each R independently is selected from hydrogen, and Formulae (Ia), (Ib), (Ic), and (Id):

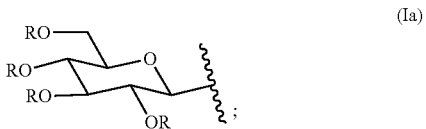
(Ia)

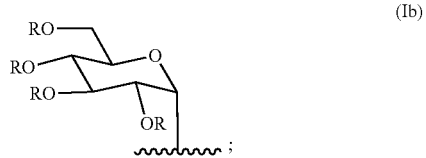
(Ib)

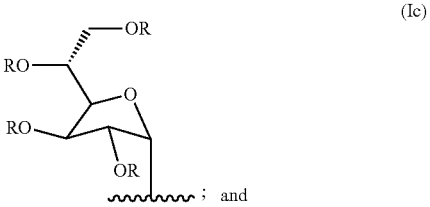
(Ic)

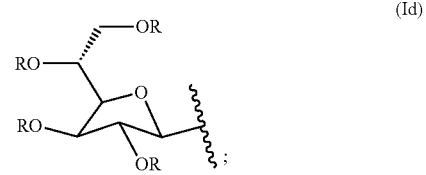
(Id)

in which each R independently is as defined above.

In other embodiments, the oligosaccharide composition is produced by a process comprising: (a) heating a dextrose preparation comprising dextrose monomer, e.g., under agitation conditions, to a temperature in a range of 120° C. to 135° C.; (b) loading the dextrose preparation with a solid catalyst comprising acidic protons, e.g., in an amount such that the molar ratio of acidic protons to dextrose monomer is in a range of 0.016-0.022, thereby forming a reaction mixture; and (c) maintaining the reaction mixture at atmospheric pressure, at a temperature in a range of 120° C. to 135° C., under conditions that promote acid catalyzed oligosaccharide formation, until the weight percent of dextrose monomer in the composition is in a range of 14-17; (d) quenching the reaction mixture using water while bringing the temperature of the reaction mixture to 100° C. or below; and optionally (e) separating oligosaccharides from the acid catalyst, thereby obtaining the oligosaccharide composition.

In other embodiments, the method comprises: (a) heating a dextrose preparation comprising dextrose monomer, under agitation conditions, to a temperature in a range of 120° C. to 135° C.; (b) loading the dextrose preparation with a solid catalyst comprising acidic protons, in an amount such that the molar ratio of acidic protons to dextrose monomer is in a range of 0.016-0.022, thereby forming a reaction mixture; and (c) maintaining the reaction mixture at its boiling point, at a pressure in the range of 0.5-1.5 atm, under conditions that promote acid catalyzed oligosaccharide formation, until the weight percent of dextrose monomer in the composition is in a range of 14-17; (d) quenching the reaction mixture using water while bringing the temperature of the reaction mixture to 100° C. or below; and optionally (e) separating oligosaccharides from the acid catalyst; thereby obtaining the oligosaccharide composition.

BRIEF DESCRIPTION OF THE DRAWINGS

FIG. 1A is a graph that demonstrates a rank-order of oligosaccharide compositions based on their effectiveness in modulating ammonia levels, normalized to a negative control (water). Arrows indicate the negative control (water) and a selected oligosaccharide composition. FIG. 1B shows a bar graph of ammonia levels normalized to the negative control (water).

FIG. 2 shows the number of patients reporting diarrhea (out of 12 patients per arm: maltodextrin (placebo), selected oligosaccharide composition, and positive control fiber) at different intake dose levels.

FIG. 3A is a graph showing reduction of ammonia by the selected oligosaccharide composition in samples from urea cycle disorder (UCD) patients. FIG. 3B is a graph showing reduction of ammonia by the selected oligosaccharide composition in samples from hepatically impaired patients.

DETAILED DESCRIPTION OF INVENTION

Figure 1A:
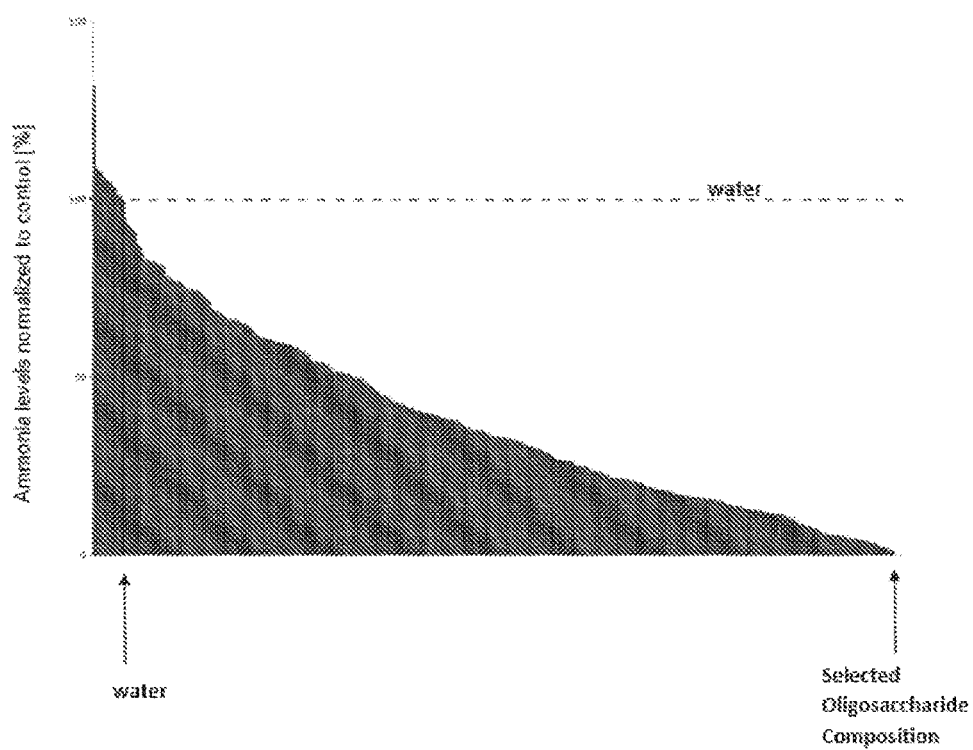
FIGS. 1A-1B provide non-limiting graphs showing ammonia reduction results (normalized to water controls) in an ex vivo ammonia reduction assay where fecal slurries were incubated with different oligosaccharide compositions.

Aspects of the disclosure relate to oligosaccharide compositions that are effective for reducing ammonia levels in a subject, e.g., a human subject. Accordingly, in some embodiments, oligosaccharide compositions disclosed herein are useful for treating a subject having a disorder associated with hyperammonemia, such as, e.g., urea cycle disorders (UCD). In some embodiments, oligosaccharide compositions disclosed herein are useful for treating a subject having another disorder associated with hyperammonemia, such as, e.g., hepatic encephalopathy (HE, e.g. minimal HE (MHE) or overt HE (OHE)).

Some aspects of the disclosure are based on the results of an extensive screening effort that was performed to identify oligosaccharide compositions that are capable of modulating, e.g., reducing, levels of ammonia in a subject. Hundreds of unique oligosaccharide compositions were assayed for their effect on ammonia levels. The oligosaccharide compositions examined in the screen were produced using different saccharide monomers, e.g., dextrose monomers, xylose monomers, etc., and under conditions involving differing reaction temperatures, for varying periods of time, and/or in the presence of different catalyst conditions.

From this screening effort, a selected oligosaccharide composition was identified as a highly effective modulator of ammonia levels that was significantly more effective for reducing ammonia levels than comparator compositions examined in the screen (Example 1). In further studies, the oligosaccharide composition was also found to be safe and well-tolerated in a placebo controlled study in healthy human adults (Example 2). Accordingly, in some embodiments, this oligosaccharide composition is particularly useful for treating a subject having a disorder associated with hyperammonemia, such as urea cycle disorders and hepatic encephalopathy.

Further aspects of the disclosure, including a description of defined terms, are provided below.

I. Definitions

Agitation conditions: As used herein, the term "agitation conditions" refers to conditions that promote or maintain a substantially uniform or homogeneous state of a mixture (e.g., a reaction mixture comprising a dextrose preparation) with respect to dispersal of solids (e.g., solid catalysts), uniformity of heat transfer, or other similar parameters. Agitation conditions generally include stirring, shaking, and/or mixing of a reaction mixture. In some embodiments, agitation conditions may include the addition of gases or other liquids into a solution. In some embodiments, agitation conditions are used to maintain substantially uniform or homogenous distribution of a catalyst, e.g., an acid catalyst. In some embodiments, a dextrose preparation is heated in the presence of an acid catalyst under suitable conditions to achieve homogeneity and uniform heat transfer in order to synthesize an oligosaccharide composition.

Approximately: As used herein, the term "approximately" or "about," as applied to one or more values of interest, refers to a value that is similar to a stated reference value. In certain embodiments, the term "approximately" or "about" refers to a range of values that fall within 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Dextrose monomer: As used herein, the term "dextrose monomer" refers to a D-isomer of a glucose monomer, known as D-glucose.

Dextrose preparation: As used herein, the term "dextrose preparation" refers to a preparation that comprises two or more saccharide units that comprise dextrose. In some embodiments, a saccharide unit that comprises dextrose is a dextrose monomer. In some embodiments, a dextrose preparation comprises dextrose monohydrate. In some embodiments, the dextrose preparation comprises dextrose monohydrage. In some embodiments, a dextrose preparation comprises 70DS corn syrup. In some embodiments, a dextrose preparation comprises a starch hydrolysate, such as, e.g., a corn syrup (e.g., a corn syrup with a reducing sugar content of greater than 20% dextrose equivalent (DE)) or a maltodextrin (e.g., a maltodextrin with a reducing sugar content of less than 20% DE). n some embodiments, a dextrose preparation can be a solid, e.g., a powder, or a syrup, e.g., a liquid comprising greater than 70% solids. In some embodiments, dextrose monomers are compliant under good manufacturing practices (GMP) conditions.

Effective amount: As used herein, the term "effective amount" refers to an administered amount or concentration of an oligosaccharide composition that is necessary and sufficient to elicit a biological response, e.g., in a subject or patient. In some embodiments, an effective amount of an oligosaccharide composition is capable of modulating, e.g., increasing or decreasing, the activity or levels of an enzyme in a subject. In some embodiments, an effective amount of an oligosaccharide composition is capable of modulating, e.g., increasing or decreasing, the processing of a metabolite. In some embodiments, an effective amount of an oligosaccharide composition is capable of modulating, e.g., increasing or decreasing, the concentration or number of at least one microbial species. In some embodiments, an effective amount of an oligosaccharide composition is capable of modulating, e.g., decreasing, the symptoms of a disease associated with hyperammonemia in a subject (e.g., the severity or number of symptoms). In some embodiments, an effective amount of an oligosaccharide composition is capable of treating a disease associated with hyperammonemia in a subject. In some embodiments, an effective amount of an oligosaccharide composition is capable of modulating, e.g., decreasing, the symptoms associated with urea cycle disorder in a subject (e.g., the severity or number of symptoms). In some embodiments, an effective amount of an oligosaccharide composition is capable of treating urea cycle disorder in a subject. In some embodiments, an effective amount of an oligosaccharide composition is capable of modulating, e.g., decreasing, the symptoms associated with hepatic encephalopathy in a subject (e.g., the severity or number of symptoms). In some embodiments, an effective amount of an oligosaccharide composition is capable of treating hepatic encephalopathy in a subject.

Hepatic encephalopathy (HE): As used herein, the term "hepatic encephalopathy (HE)" refers to a class of disease that includes multiple adverse neurological symptoms which occur as a results of advanced liver disease or otherwise when the liver is unable to remove toxic substances such as ammonia from the blood. In some embodiments, HE arises as a consequence of or in conjunction with liver cirrhosis. In some embodiments, a subject having hepatic encephalopathy has elevated levels of ammonia relative to a normal, healthy subject. In some embodiments, a subject having hepatic encephalopathy may have mild HE, severe HE, or overt HE. Standard-of-care treatments for HE include lactulose, lactitol, and antibiotics (e.g., rifaximin or neomycin). Treatments may also include dietary modifications and probiotics. Treatment efficacy may be assessed by resolution of the symptoms above (e.g., reduction in serum ammonia levels), decreased incidence of future episodes of HE, or, in a subject at risk of HE, by decreased occurrence of an initial episode of HE. In some embodiments, a patient who has experienced an extended duration of hyperammonemia or high peak ammonia, particularly a patient with liver damage (e.g., a patient with liver cirrhosis, e.g., an elderly patient), may develop hepatic encephalopathy (HE) associated with profound and chronic neurologic morbidity, including severe intellectual disability, deficits in executive function impacting daily activities, e.g., such as, confusion, forgetfulness, anxiety or excitation, sudden changes in personality or behavior, changes in sleep patterns, disorientation, sweet or musty smelling breath, slurred speech, and/or difficulty controlling motor functions.

Hyperammonemia: As used herein, the term "hyperammonemia" refers to a condition in a subject (e.g., a human subject) associated with elevated levels of ammonia. Generally, a subject having hyperammonemia has elevated levels of ammonia in circulation, e.g., in blood. In some embodiments, the duration and severity of hyperammonemia is positively correlated with brain damage. In some embodiments, a patient who has experienced an extended duration of hyperammonemia or high peak ammonia, particularly a pediatric patient, may develop profound and chronic neurologic morbidity, including developmental delay, severe intellectual disability, deficits in executive function impacting daily activities, cerebral palsy, and seizure disorder.

Oligosaccharide: As used herein, the term "oligosaccharide" (which may be used interchangeably with the term "glycan" in some contexts) refers to a saccharide molecule comprising at least two monosaccharides (e.g., dextrose monomers) linked together via a glycosidic bond (having a degree of polymerization (DP) of at least 2 (e.g., DP2+)). In some embodiments, an oligosaccharide comprises at least two, at least three, at least four, at least five, at least six, at least seven, at least eight, at least nine, or at least ten monosaccharides subunits linked by glycosidic bonds. In some embodiments, an oligosaccharide in the range of 10-25, 20-50, 40-80, 75-100, 100-150, or at least 100 monosaccharides linked by glycosidic bonds. In some embodiments, an oligosaccharide comprises at least one 1,2; 1,3; 1,4; and/or 1,6 glycosidic bond. Oligosaccharides may be linear or branched. Oligosaccharides may have one or more glycosidic bonds that are in alpha-configurations and/or one or more glycosidic bonds that are in beta-configurations.

Pharmaceutical Composition: As used herein, a "pharmaceutical composition" refers to a composition having pharmacological activity or other direct effect in the mitigation, treatment, or prevention of disease, and/or a finished dosage form or formulation thereof and is for human use. A pharmaceutical composition or pharmaceutical preparation is typically produced under good manufacturing practices (GMP) conditions. Pharmaceutical compositions or preparations may be sterile or non-sterile. If non-sterile, such pharmaceutical compositions or preparations typically meet the microbiological specifications and criteria for non-sterile pharmaceutical products as described in the U.S. Pharmacopeia (USP) or European Pharmacopoeia (EP). Any oligosaccharide composition described herein may be formulated as a pharmaceutical composition.

Subject: As used herein, the term "subject" refers to a human subject or patient. A subject may include a newborn (a preterm newborn, a full-term newborn), an infant up to one year of age, young children (e.g., 1 yr to 12 yrs), teenagers, (e.g., 13-19 yrs), adults (e.g., 20-64 yrs), and elderly adults (65 yrs and older). In some embodiments, a subject is of a pediatric population, or a subpopulation thereof, including neonates (birth to 1 month), infants (1 month to 2 years), developing children (2-12 years), and adolescents (12-16 years).

Treatment and Treating: As used herein, the terms "treating" and "treatment" refer to the administration of a composition to a subject (e.g., a symptomatic subject afflicted with an adverse condition, disorder, or disease) so as to affect a reduction in severity and/or frequency of a symptom, eliminate a symptom and/or its underlying cause, and/or facilitate improvement or remediation of damage, and/or preventing an adverse condition, disorder, or disease in an asymptomatic subject who is susceptible to a particular adverse condition, disorder, or disease, or who is suspected of developing or at risk of developing the condition, disorder, or disease.

Urea Cycle Disorders: As used herein, the term "urea cycle disorders" refers to a group of genetic diseases caused by mutation that result in a deficiency of one or more enzymes in the urea cycle. In some embodiments, such enzymes are generally responsible for removing ammonia from the blood stream. For example, the urea cycle generally encompasses a series of reactions that transform nitrogen from peripheral (muscle) and enteral (protein ingestion) sources into urea for excretion. In some embodiments, genetic defects in the enzymes involved in this metabolic pathway result in a variety of malfunctions of ammonia detoxification/arginine synthesis. In some embodiments, defects in the urea cycle lead to a metabolic state of elevated levels of ammonia (hyperammonemia) that can cause cerebral edema, neurologic injury, respiratory alkalosis, coma, and sometimes death. The severity of the disease varies significantly based on the level of deficiency in the enzyme/transporter, the urea cycle disorder (UCD) subtype, and other factors. In some embodiments, there are two types of onset for UCD: neonatal and late onset. Over 69% of cases are late onset, meaning that they occur after the newborn period. More than 50% of cases occur in the pediatric population in the US, aged 0-18 years of age.

II. Oligosaccharide Compositions

Provided herein are oligosaccharide compositions (e.g., glycan polymers), and their methods of use for modulating levels of ammonia in a human subject and for treatment of urea cycle disorders.

In one aspect, oligosaccharide compositions are provided herein that comprise a plurality of oligosaccharides (e.g., a plurality of oligosaccharides that are minimally digestible by humans) that comprise Formula (I):

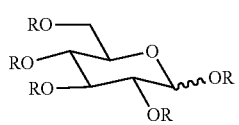
(I)

wherein each R independently is selected from hydrogen, and Formulae (Ia), (Ib), (Ic), and (Id):

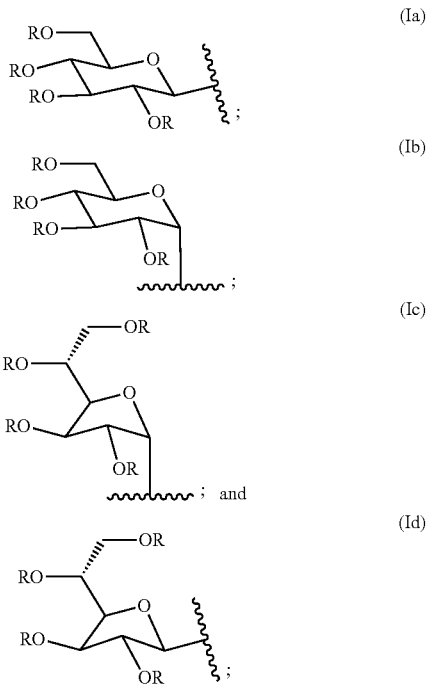

in which each R independently is as defined above.

In some embodiments, an oligosaccharide is minimally digestible by a human (e.g., not broken down or catalyzed by human cells or by enzymatic function of human enzymes).

Generation of Oligosaccharide Compositions

Preparations comprising oligosaccharide compositions can be generated using a non-enzymatic catalyst, e.g., as described in WO 2019/090181, METHODS OF PRODUCING GLYCAN POLYMERS. In some cases, the oligosaccharide compositions can be produced using a polymeric catalyst described in WO 2012/118767, "POLYMERIC ACID CATALYSTS AND USES THEREOF" or by other suitable methods, e.g., as described in WO 2016/007778, "OLIGOSACCHARIDE COMPOSITIONS AND METHODS FOR PRODUCING THEREOF", each of which is incorporated herein by reference in its entirety. Other acid catalysts (e.g. solid catalysts) may be used. Methods to prepare the polymeric and solid-supported catalysts described herein can be found in WO 2014/031956, "POLYMERIC AND SOLID-SUPPORTED CATALYSTS, AND METHODS OF DIGESTING CELLULOSIC MATERIALS USING SUCH CATALYSTS," which is incorporated herein by reference in its entirety.

In some embodiments, such oligosaccharide compositions are produced by a process that initially involves heating a dextrose preparation comprising dextrose (e.g., dextrose monomers or monosaccharides) to a temperature in a range of about 120° C. to about 135° C., e.g., 120° C. to 130° C., 125° C. to 130° C., 125° C. to 135° C., 128° C. to 132° C., 130° C. to 133° C., 130° C. to 135° C. or 132° C. to 135° C. In some embodiments, the dextrose preparation comprising dextrose monomers is heated to a temperature of 120° C., 121° C., 122° C., 123° C., 124° C., 125° C., 126° C., 127° C., 128° C., 129° C., 130° C., 131° C., 132° C., 133° C., 134° C., or 135° C. Heating may be performed under agitation conditions.

A catalyst comprising acidic protons is added to the dextrose preparation (e.g., during or following heating) to promote the formation of one or more glycosidic bonds between dextrose units (e.g., dextrose monomers), thereby producing an oligosaccharide composition. Suitable catalysts comprise acidic monomers, optionally, wherein each acidic monomer has at least one Bronsted-Lowry acid. Typically, the catalyst will be added in an amount such that the molar ratio of acidic protons to dextrose monomer is in a range of 0.001-0.25, e.g., 0.001-0.1, 0.01-0.1, 0.001-0.08, 0.01-0.05, 0.016-0.022, 0.05-0.1 or 0.05-0.2. In some embodiments, the catalyst comprises >3.0 mmol/g sulfonic acid moieties and <1.0 mmol/gram cationic moieties. In some embodiments, the catalyst has a nominal moisture content of 45-50 weight percent.

In some embodiments, the catalyst can be an alkaline or acidic catalyst, a catalytic resin, or a metal catalyst. In some embodiments, the catalyst is an organic acid, an inorganic acid, or an anhydride. In some embodiments, the catalyst is a homogenous acid catalyst. In some embodiments, the catalyst is a heterogeneous acid catalyst. In some embodiments, the catalyst is not an enzyme.

Non-limiting examples of acid catalysts than can be used to produce an oligosaccharide as described herein include: adipic acid, acetic acid, citric acid, fumaric acid, gluconic acid, itaconic acid, lactic acid, maleic acid, malic acid, succinic acid, tartaric acids, terephthalic acids, hydrochloric acid, sulfuric acid, sulfurous acid, thiosulfuric acid, dithionic acid, pyrosulfuric acid, selenic acid, selenious acid, nitric acid, phosphoric acid, phosphorous acid, hypophosphorous acid, pyrophosphoric acid, polyphosphoric acid, hypophosphoric acid, boric acid, perchloric acid, hypochlorous acid, hydrobromic acid. In some embodiments, the acid catalyst is an acidic alkali metal or alkaline earth metal salts of an inorganic acid.

In some embodiments, the catalyst used to prepare the oligosaccharide composition is a solid acidic catalyst, e.g., a solid-supported or resin-bound acidic catalyst. In some embodiments, the catalyst used to prepare a glycan polymer preparation is a solid acid catalyst (e.g., clay minerals (e.g., montaiorillonite, bentonite, kaolinite or cation exchanged zeolites and clays, and/or their sulfated or acidified forms), zeolites, alumina, silico-alumino-phosphates, heteropolyoxometallates, metal oxides and sulphides (ALA and ZnS), metals salts (MgSO4), mixed oxides (SiO2-Al2O3), sulphate-promoted metal oxides and mixed oxides (SO4(2-)/ZrO2, SO4(2-)/TiO2 and SO4(2-)/Fe2O3), mounted acids (suitable carriers like porous oxides, graphite, metal salts, treated or combined with liquid acids like H2SO4/SiO2, SbF5/SiO2-Al$_2$O3. AlCI3/CuSO4), cation exchange resins, pcrfluorinated polymer sulphuric acid (Nafion-H) and hcteropolyacids (12-tungstophosphoric acid), heteropolyoxometallates, sultonated carbon, sulfated carbon, sulfated ash. In certain embodiments, the catalyst is an ion exchange resin (e.g., AMBERLITE FPC11 Na, AMBERLITE FPC14 Na, DOWEX 88, DOWEX 88 H, DOWEX 88 MB, DOWEX 88 MB H, DOWEX FPC16UPS H, DOWEX FPC16UPS Na, DOWEX FPC23UPS H, DOWEX MAC-3, DOWEX MONOSPHERE 88, DOWEX MONOSPHERE 88 H, DOWEX MONOSPHERE 99 Ca/310, DOWEX MONOSPHERE 99 Ca/320, DOWEX MONOSPHERE 99 K/310, DOWEX MONOSPHERE 99 K/320, DOWEX MONOSPHERE 99 K/350, DOWEX™ PSR-2, DOWEX™ G-26 H, AMBERJET 1600 H, AMBERJET 2000 H, AMBERLITE IRN150, AMBERLITE IRN160, AMBERLITE IRN170, AMBERLITE IRN217, AMBERLITE IRN317, AMBERLITE IRN360, AMBERLITE IRN77, AMBERLITE IRN97 H, AMBERLITE IRN99 H, AMBERLITE IRN9652, AMBERLITEIRN9882, AMBERLITE IRN9687, AMBERSEP 252 H, DOWEX MONOSPHERE 1400PC H, DOWEX MONOSPHERE 650C H, AMBERLITE 200C Na, AMBERLITE IR120 H, AMBERLITE IR120 Na, AMBERLITE IRC83, AMBERLITE MB20, DOWEX MARATHON 1200 H, DOWEX MARATHON 1200 Na, DOWEX MARATHON 1300 H, DOWEX MARATHON 8300, DOWEX MARATHON C, DOWEX MARATHON C-10, DOWEX MARATHON MR-3, DOWEX MARATHON MSC, DOWEX MARATHON MSC H, DOWEX™ HCR-S/S, IMAC™ HP333, AMBERJET UP1400, AMBERJET UP6040, AMBERJET UP6150, DOWEX MONOSPHERE MR-3 UPW, DOWEX MONOSPHERE MR-450 UPW, AMBERLITE CG50 Type 1, AMBERLITE COBALAMION, AMBERLITE FPC3500, AMBERLITE IRP476, AMBERLITE IRP64, AMBERLITE IRP69, AMBERLITE IRP88, DOWEX 50WX2 (H+), DOWEX 50WX4 (H+), DOWEX 50WX8 (H+), AMBERLITE BD10, AMBERLITE IRC84SPI H, AMBERLYST 123, AMBERLYST 125, AMBERLYST 131, AMBERLYST 15, AMBERLYST 16, AMBERLYST 19, AMBERLYST 33, AMBERLYST 35, AMBERLYST 36, AMBERLYST 39, AMBERLYST 40, AMBERLYST 45, AMBERLYST BD20, AMBERLYST CH28, AMBERSEP BD19, AMBERSEP 200 H) in its protonated form.

In some embodiments, the catalyst is selected from poly[styrene-co-4-vinylbenzenesulfonic acid-co-3-methyl-1-(4-vinylbenzyl)-3H-imidazol-1-ium chloride-co-divinylbenzene]; poly[styrene-co-4-vinylbenzenesulfonic acid-co-3-methyl-1-(4-vinylbenzyl)-3H-imidazol-1-ium bisulfate-co-divinylbenzene]; poly[styrene-co-4-vinylbenzenesulfonic acid-co-3-methyl-1-(4-vinylbenzyl)-3H-imidazol-1-ium acetate-co-divinylbenzene]; poly[styrene-co-4-vinylbenzenesulfonic acid-co-3-methyl-1-(4-vinylbenzyl)-3H-imidazol-1-ium nitrate-co-divinylbenzene]; poly[styrene-co-4-vinylbenzenesulfonic acid-co-3-ethyl-1-(4-vinylbenzyl)-3H-imidazol-1-ium chloride-co-divinylbenzene]; poly[styrene-co-4-vinylbenzenesulfonic acid-co-3-ethyl-1-(4-vinylbenzyl)-3H-imidazol-1-ium bisulfate-co-divinylbenzene]; poly[styrene-co-4-vinylbenzenesulfonic acid-co-3-ethyl-1-(4-vinylbenzyl)-3H-imidazol-1-ium acetate-co-divinylbenzene]; poly[styrene-co-4-vinylbenzenesulfonic acid-co-3-ethyl-1-(4-vinylbenzyl)-3H-imidazol-1-ium nitrate-co-divinylbenzene]; poly[styrene-co-4-vinylbenzenesulfonic acid-co-1-(4-vinylbenzyl)-3H-imidazol-1-ium chloride-co-divinylbenzene]; poly[styrene-co-4-vinylbenzenesulfonic acid-co-1-(4-vinylbenzyl)-3H-imidazol-1-ium iodide-co-divinylbenzene]; poly[styrene-co-4-vinylbenzenesulfonic acid-co-1-(4-vinylbenzyl)-3H-imidazol-1-ium bromide-co-divinylbenzene]; poly[styrene-co-4-vinylbenzenesulfonic acid-co-1-(4-vinylbenzyl)-3H-imidazol-1-ium bisulfate-co-divinylbenzene]; poly[styrene-co-4-vinylbenzenesulfonic acid-co-1-(4-vinylbenzyl)-3H-imidazol-1-ium acetate-co-divinylbenzene]; poly[styrene-co-4-vinylbenzenesulfonic acid-co-3-methyl-1-(4-vinylbenzyl)-3H-benzoimidazol-1-ium chloride-co-divinylbenzene]; poly[styrene-co-4-vinylbenzenesulfonic acid-co-3-methyl-1-(4-vinylbenzyl)-3H-benzoimidazol-1-ium bisulfate-co-divinylbenzene]; poly[styrene-co-4-vinylbenzenesulfonic acid-co-3-methyl-1-(4-vinylbenzyl)-3H-benzoimidazol-1-ium acetate-co-divinylbenzene]; poly[styrene-co-4-vinylbenzenesulfonic acid-co-3-methyl-1-(4-vinylbenzyl)-3H-benzoimidazol-1-ium formate-co-divinylbenzene]; poly[styrene-co-4-vinylbenzenesulfonic acid-co-1-(4-vinylbenzyl)-pyridinium-chloride-co-divinylbenzene]; poly[styrene-co-4-vinylbenzenesulfonic acid-co-1-(4-vinylbenzyl)-pyridinium-bisulfate-codivinylbenzene]; poly[styrene-co-4-vinylbenzenesulfonic acid-co-1-(4-vinylbenzyl)-pyridinium-acetate-co-divinylbenzene]; poly[styrene-co-4-vinylbenzenesulfonic acid-co-1-(4-vinylbenzyl)-pyridinium-nitrate-co-divinylbenzene]; poly[styrene-co-4-vinylbenzenesulfonic acid-co-1-(4-vinylbenzyl)-pyridinium-chloride-co-3-methyl-1-(4-vinylbenzyl)-3H-imidazol-1-ium bisulfate-co-divinylbenzene]; poly[styrene-co-4-vinylbenzenesulfonic acid-co-1-(4-vinylbenzyl)-pyridinium-bromide-co-3-methyl-1-(4-vinylbenzyl)-3H-imidazol-1-ium bisulfate-co-divinylbenzene]; poly[styrene-co-4-vinylbenzenesulfonic acid-co-1-(4-vinylbenzyl)-pyridinium-iodide-co-3-methyl-1-(4-vinylbenzyl)-3H-imidazol-1-ium bisulfate-co-divinylbenzene]; poly[styrene-co-4-vinylbenzenesulfonic acid-co-1-(4-vinylbenzyl)-pyridinium-bisulfate-co-3-methyl-1-(4-vinylbenzyl)-3H-imidazol-1-ium bisulfate-co-divinylbenzene]; poly[styrene-co-4-vinylbenzenesulfonic acid-co-1-(4-vinylbenzyl)-pyridinium-acetate-co-3-methyl-1-(4-vinylbenzyl)-3H-imidazol-1-ium bisulfate-co-divinylbenzene]; poly[styrene-co-4-vinylbenzenesulfonic acid-co-4-methyl-4-(4-vinylbenzyl)-morpholin-4-ium chloride-co-divinylbenzene]; poly[styrene-co-4-vinylbenzenesulfonic acid-co-4-methyl-4-(4-vinylbenzyl)-morpholin-4-ium bisulfate-co-divinylbenzene]; poly[styrene-co-4-vinylbenzenesulfonic acid-co-4-methyl-4-(4-vinylbenzyl)-morpholin-4-ium acetate-co-divinylbenzene]; poly[styrene-co-4-vinylbenzenesulfonic acid-co-4-methyl-4-(4-vinylbenzyl)-morpholin-4-ium formate-co-divinylbenzene]; poly[styrene-co-4-vinylbenzenesulfonic acid-co-triphenyl-(4-vinylbenzyl)-phosphonium chloride-co-divinylbenzene]; poly[styrene-co-4-vinylbenzenesulfonic acid-co-triphenyl-(4-vinylbenzyl)-phosphonium bisulfate-co-divinylbenzene]; poly[styrene-co-4-vinylbenzenesulfonic acid-co-triphenyl-(4-vinylbenzyl)-phosphonium acetate-co-divinylbenzene]; poly[styrene-co-4-vinylbenzenesulfonic acid-co-1-methyl-1-(4-vinylbenzyl)-piperidin-1-ium chloride-co-divinylbenzene]; poly[styrene-co-4-vinylbenzenesulfonic acid-co-1-methyl-1-(4-vinylbenzyl)-piperidin-1-ium bisulfate-co-divinylbenzene]; poly[styrene-co-4-vinylbenzenesulfonic acid-co-1-methyl-1-(4-vinylbenzyl)-piperidin-1-ium acetate-co-divinylbenzene]; poly[styrene-co-4-vinylbenzenesulfonic acid-co-4-(4-vinylbenzyl)-morpholine-4-oxide-co-divinyl benzene]; poly[styrene-co-4-vinylbenzenesulfonic acid-co-triethyl-(4-vinylbenzyl)-ammonium chloride-co-divinylbenzene]; poly[styrene-co-4-vinylbenzenesulfonic acid-co-triethyl-(4-vinylbenzyl)-ammonium bisulfate-co-divinylbenzene]; poly[styrene-co-4-vinylbenzenesulfonic acid-co-triethyl-(4-vinylbenzyl)-ammonium acetate-co-divinylbenzene]; poly[styrene-co-3-methyl-1-(4-vinylbenzyl)-3H-imidazol-1-ium chloride-co-4-boronyl-1-(4-vinylbenzyl)-pyridinium chloride-co-divinylbenzene]; poly[styrene-co-3-methyl-1-(4-vinylbenzyl)-3H-imidazol-1-ium chloride-co-1-(4-vinylphenyl)methylphosphonic acid-co-divinylbenzene]; poly[styrene-co-3-methyl-1-(4-vinylbenzyl)-3H-imidazol-1-ium bisulfate-co-1-(4-vinylphenyl)methylphosphonic acid-co-divinylbenzene]; poly[styrene-co-3-methyl-1-(4-vinylbenzyl)-3H-imidazol-1-ium acetate-co-1-(4-vinylphenyl)methylphosphonic acid-co-divinylbenzene]; poly [styrene-co-3-methyl-1-(4-vinylbenzyl)-3H-imidazol-1-ium nitrate-co-1-(4-vinylphenyl)methylphosphonic acid-co-divinylbenzene]; poly[styrene-co-4-vinylbenzenesulfonic acid-co-vinylbenzylchloride-co-1-methyl-2-vinyl-pyridinium chloride-co-divinylbenzene]; poly[styrene-co-4-vinylbenzenesulfonic acid-co-vinylbenzylchloride-co-1-methyl-2-vinyl-pyridinium bisulfate-co-divinylbenzene]; poly[styrene-co-4-vinylbenzenesulfonic acid-co-vinylbenzylchloride-co-1-methyl-2-vinyl-pyridinium acetate-co-divinylbenzene]; poly[styrene-co-4-vinylbenzenesulfonic acid-co-4-(4-vinylbenzyl)-morpholine-4-oxide-co-divinyl benzene]; poly[styrene-co-4-vinylphenylphosphonic acid-co-3-methyl-1-(4-vinylbenzyl)-3H-imidazol-1-ium chloride-co-divinylbenzene]; poly[styrene-co-4-vinylphenylphosphonic acid-co-3-methyl-1-(4-vinylbenzyl)-3H-imidazol-1-ium bisulfate-co-divinylbenzene]; poly[styrene-co-4-vinylphenylphosphonic acid-co-3-methyl-1-(4-vinylbenzyl)-3H-imidazol-1-ium acetate-co-divinylbenzene]; polyj[styrene-co-3-carboxymethyl-1-(4-vinylbenzyl)-3H-imidazol-1-ium chloride-co-divinylbenzene]; poly[styrene-co-3-carboxymethyl-1-(4-vinylbenzyl)-3H-imidazol-1-ium bisulfate-co-divinylbenzene]; poly[styrene-co-3-carboxymethyl-1-(4-vinylbenzyl)-3H-imidazol-1-ium acetate-co-divinylbenzene]; poly [styrene-co-5-(4-vinylbenzylamino)-isophthalic acid-co-3-methyl-1-(4-vinylbenzyl)-3H-imidazol-1-ium chloride-co-divinylbenzene]; poly [styrene-co-5-(4-vinylbenzylamino)-isophthalic acid-co-3-methyl-1-(4-vinylbenzyl)-3H-imidazol-1-ium bisulfate-co-divinylbenzene]; poly [styrene-co-5-(4-vinylbenzylamino)-isophthalic acid-co-3-methyl-1-(4-vinylbenzyl)-3H-imidazol-1-ium acetate-co-divinylbenzene]; poly[styrene-co-(4-vinylbenzylamino)-acetic acid-co-3-methyl-1-(4-vinylbenzyl)-3H-imidazol-1-ium chloride-co-divinylbenzene]; poly[styrene-co-(4-vinylbenzylamino)-acetic acid-co-3-methyl-1-(4-vinylbenzyl)-3H-imidazol-1-ium bisulfate-co-divinylbenzene]; poly[styrene-co-(4-vinylbenzylamino)-acetic acid-co-3-methyl-1-(4-vinylbenzyl)-3H-imidazol-1-ium acetate-co-divinylbenzene]; poly(styrene-co-4-vinylbenzenesulfonic acid-co-vinylbenzylmethylimidazolium chloride-co-vinylbenzylmethylmorpholinium chloride-co-vinylbenzyltriphenyl phosphonium chloride-co-divinylbenzene); poly(styrene-co-4-vinylbenzenephosphonic acid-co-vinylbenzylmethylimidazolium chloride-co-vinylbenzylmethylmorpholinium chloride-co-vinylbenzyltriphenyl phosphonium chloride-co-divinylbenzene); poly(styrene-co-4-vinylbenzenesulfonic acid-co-vinylbenzylmethylimidazolium bisulfate-co-vinylbenzylmethylmorpholinium bisulfate-co-vinylbenzyltriphenyl phosphonium bisulfate-co-divinylbenzene); poly(styrene-co-4-vinylbenzenephosphonic acid-co-vinylbenzylmethylimidazolium bisulfate-co-vinylbenzylmethylmorpholinium bisulfate-co-vinylbenzyltriphenyl phosphonium bisulfate-co-divinylbenzene); poly(styrene-co-4-vinylbenzenesulfonic acid-co-vinylbenzylmethylimidazolium acetate-co-vinylbenzylmethylmorpholinium acetate-co-vinylbenzyltriphenyl phosphonium acetate-co-divinylbenzene); poly(styrene-co-4-vinylbenzenephosphonic acid-co-vinylbenzylmethylimidazolium acetate-co-vinylbenzylmethylmorpholinium acetate-co-vinylbenzyltriphenyl phosphonium acetate-co-divinylbenzene); poly(styrene-co-4-vinylbenzenesulfonic acid-co-vinylbenzylmethylmorpholinium chloride-co-vinylbenzyltriphenylphosphonium chloride-co-divinylbenzene); poly(styrene-co-4-vinylbenzenephosphonic acid-co-vinylbenzylmethylmorpholinium chloride-co-vinylbenzyltriphenylphosphonium chloride-co-divinylbenzene); poly(styrene-co-4-vinylbenzenesulfonic acid-co-vinylbenzylmethylmorpholinium bisulfate-co-vinylbenzyltriphenylphosphonium bisulfate-co-divinylbenzene); poly(styrene-co-4-vinylbenzenephosphonic acid-co-vinylbenzylmethylmorpholinium bisulfate-co-vinylbenzyltriphenylphosphonium bisulfate-co-divinylbenzene); poly(styrene-co-4-vinylbenzenesulfonic acid-co-vinylbenzylmethylmorpholinium acetate-co-vinylbenzyltriphenylphosphonium bisulfate-co-divinylbenzene); poly(styrene-co-4-vinylbenzenephosphonic acid-co-vinylbenzylmethylmorpholinium acetate-co-vinylbenzyltriphenylphosphonium bisulfate-co-divinylbenzene); poly (styrene-co-4-vinylbenzenesulfonic acid-co-vinylmethylimidazolium chloride-co-divinylbenzene); poly(styrene-co-4-vinylbenzenesulfonic acid-co-vinylmethylimidazolium bisulfate-co-divinylbenzene); poly(styrene-co-4-vinylbenzenesulfonic acid-co-vinylmethylimidazolium acetate-co-divinylbenzene); poly(styrene-co-4-vinylbenzenesulfonic acid-co-vinylmethylimidazolium nitrate-co-divinylbenzene); poly(styrene-co-4-vinylbenzenephosphonic acid-co-vinylmethylimidazolium chloride-co-divinylbenzene); poly(styrene-co-4-vinylbenzenephosphonic acid-co-vinylmethylimidazolium bisulfate-co-divinylbenzene); poly(styrene-co-4-vinylbenzenephosphonic acid-co-vinylmethylimidazolium acetate-co-divinylbenzene); poly(styrene-co-4-vinylbenzenesulfonic acid-co-vinylbenzyl-triphenylphosphonium chloride-co-divinylbenzene); poly(styrene-co-4-vinylbenzenesulfonic acid-co-vinylbenzyltriphenylphosphonium bisulfate-co-divinylbenzene); poly(styrene-co-4-vinylbenzenesulfonic acid-co-vinylbenzyltriphenylphosphonium acetate-co-divinylbenzene); poly(styrene-co-4-vinylbenzenephosphonic acid-co-vinylbenzyl-triphenylphosphonium chloride-co-divinylbenzene); poly(styrene-co-4-vinylbenzenephosphonic acid-co-vinylbenzyl-triphenylphosphonium bisulfate-co-divinylbenzene); poly(styrene-co-4-vinylbenzenephosphonic acid-co-vinylbenzyltriphenylphosphonium acetate-co-divinylbenzene); poly(styrene-co-4-vinylbenzenesulfonic acid-co-vinylbenzylmethylimidazolium chloride-co-divinylbenzene); poly(styrene-co-4-vinylbenzenesulfonic acid-co-vinylbenzylmethylimidazolium bisulfate-co-divinylbenzene); poly(styrene-co-4-vinylbenzenesulfonic acid-co-vinylbenzyl-methylimidazolium acetate-co-divinylbenzene); poly(styrene-co-4-vinylbenzenephosphonic acid-co-vinylbenzylmethylimidazolium chloride-co-divinylbenzene); poly(styrene-co-4-vinylbenzenephosphonic acid-co-vinylbenzylmethylimidazolium bisulfate-co-divinylbenzene); poly(styrene-co-4-vinylbenzenephosphonic acid-co-vinylbenzylmethylimidazolium acetate-co-divinylbenzene); poly(styrene-co-4-vinylbenzenesulfonic acid-co-vinylbenzyl-triphenylphosphonium chloride-co-divinylbenzene); poly(styrene-co-4-vinylbenzenesulfonic acid-co-vinylbenzyltriphenylphosphonium bisulfate-co-divinylbenzene); poly(styrene-co-4-vinylbenzenesulfonic acid-co-vinylbenzyltriphenylphosphonium acetate-co-divinylbenzene); poly(styrene-co-4-vinylbenzenephosphonic acid-co-vinylbenzyltriphenylphosphonium chloride-co-divinylbenzene); poly(styrene-co-4-vinylbenzenephosphonic acid-co-vinylbenzyl-triphenylphosphonium bisulfate-co-divinylbenzene); poly(styrene-co-4-vinylbenzenephosphonic acid-co-vinylbenzyltriphenylphosphonium acetate-co-divinylbenzene); poly(butyl-vinylimidazolium chloride-co-butylimidazolium bisulfate-co-4-vinylbenzenesulfonic acid); poly(butyl-vinylimidazolium bisulfate-co-butylimidazolium bisulfate-co-4-vinylbenzenesulfonic acid); poly(benzyl alcohol-co-4-vinylbenzylalcohol sulfonic acid-co-vinylbenzyl-triphenylphosphonium chloride-co-divinylbenzyl alcohol); poly(benzyl alcohol-co-4-vinylbenzylalcohol sulfonic acid-co-vinylbenzyltriphenylphosphonium bisulfate-co-divinylbenzyl alcohol); poly(styrene-co-vinylbenzenesulfonic acid-co-divinylbenzene); poly(styrene-co-vinylbenzenephosphonic acid-co-divinylbenzene); poly(styrene-co-vinylbenzeneboronic acid-co-divinylbenzene); sulfonated polystyrene-co-divinylbenzene microporous gel resin; sulfonated polystyrene-co-divinylbenzene macroporous resin.

In some embodiments, the catalyst is a strong acid cation exchange resin having one or more physical and chemical properties according to Table 1. In some embodiments, the catalyst comprises >3.0 mmol/g sulfonic acid moieties and <1.0 mmol/gram cationic moieties.

In some embodiments, the catalyst used to prepare the oligosaccharide composition is a soluble acidic catalyst.

In some embodiments, after loading of the catalyst with the dextrose preparation, the resultant reaction mixture is held at atmospheric pressure and at a temperature in a range of about 120° C. to 135° C. under conditions that promote acid catalyzed oligosaccharide formation.

In some embodiments, after loading the catalyst, the reaction mixture is maintained at its boiling point, under conditions that promote acid catalyzed oligosaccharide formation. The ambient pressure of the reaction mixture may be a pressure in the range of 0.5-1.5 atm. For example, the pressure may be less than 1 atm (e.g., about 0.5, 0.6, 0.7, 0.8, or 0.9 atm), about 1 atm, or greater than 1 atm (e.g., about 1.1, 1.2, 1.3, 1.4, or 1.5 atm). In some embodiments, after loading of the catalyst with the dextrose preparation, the resultant reaction mixture is held outside of atmospheric pressure (e.g., at less than 0.5 atm or greater than 1.5 atm), but at a temperature and under conditions that promote acid catalyzed oligosaccharide formation.

In some embodiments, the reaction mixture is maintained at its boiling point until the weight percent of dextrose monomer in the synthesized oligosaccharide composition is in a particular range, e.g., once the weight percent of dextrose monomer in the synthesized oligosaccharide composition is 30% or less (e.g., 28% or less, 25% or less, 22% or less, 20% or less, 19% or less, 18% or less, 17% or less, 16% or less, 15% or less, 14% or less, 13% or less, 12% or less, 11% or less, or 10% or less). In some embodiments, the reaction mixture is maintained at its boiling point until the weight percent of dextrose monomer in the synthesized oligosaccharide composition is in a particular range, e.g., 10% to 20%, 12% to 22%, 14% to 22%, 14% to 20%, 14% to 18%, 12% to 18%, or 16% to 24%. In some embodiments, once the weight percent of dextrose monomer in the synthesized oligosaccharide composition is in a particular range, e.g., once the weight percent of dextrose monomer in the synthesized oligosaccharide composition is 30% or less (e.g., 28% or less, 25% or less, 22% or less, 20% or less, 19% or less, 18% or less, 17% or less, 16% or less, 15% or less, 14% or less, 13% or less, 12% or less, 11% or less, or 10% or less), the reaction mixture is quenched. In some embodiments, once the weight percent of dextrose monomer in the synthesized oligosaccharide composition is in a particular range, e.g., 10% to 20%, 12% to 22%, 14% to 22%, 14% to 20%, 14% to 18%, 12% to 18%, or 16% to 24%, the reaction mixture is quenched. In some embodiments, quenching involves using water (e.g., deionized water) to dilute the reaction mixture, and gradually decrease the temperature of the reaction mixture to 100° C. or below.

In some embodiments, the reaction mixture is maintained at its boiling point until the molar ratio of net water condensate to the total dextrose that was present in the reaction mixture prior to heating is in a particular range, e.g., a range of 0.35 to 1.0 (e.g., a range of 0.35 to 0.8, 0.4 to 0.9, 0.5 to 0.9, 0.5 to 0.8, 0.6 to 0.9, 0.6 to 0.8, or 0.7 to 0.9). For example, in some embodiments, the reaction mixture is maintained at its boiling point until the molar ratio of net water condensate to total dextrose monomer in a reaction mixture prior to heating is 0.4 to 0.9 (e.g., about 0.6 to 0.8).

In some embodiments, once the molar ratio of net water condensate to the total dextrose that was present in the reaction mixture prior to heating is in a particular range, e.g., a range of 0.35 to 1.0 (e.g., a range of 0.35 to 0.8, 0.4 to 0.9, 0.5 to 0.9, 0.5 to 0.8, 0.6 to 0.9, 0.6 to 0.8, or 0.7 to 0.9), the reaction mixture is quenched. For example, in some embodiments, once the molar ratio of net water condensate to total dextrose monomer in a reaction mixture prior to heating is 0.4 to 0.9 (e.g., about 0.6 to 0.8), the reaction mixture is quenched. In some embodiments, quenching involves using water (e.g., deionized water) to dilute the reaction mixture, and gradually decrease the temperature of the reaction mixture to 100° C. or below.

In some embodiments, the oligosaccharide composition comprises less than 10% sorbitol, e.g., about 10%, about 8%, about 6%, about 4%, about 2%, about 1% sorbitol, or about 0.1% or less sorbitol, in the reaction mixture. In some embodiments, the oligosaccharide composition comprises less than 10% sorbitol, e.g., about 10%, about 8%, about 6%, about 4%, about 2%, about 1% sorbitol, or about 0.1% or less sorbitol, in the reaction mixture, and less than 10% sorbitol, e.g., about 10%, about 8%, about 6%, about 4%, about 2%, about 1% sorbitol, or about 0.1% or less sorbitol, in the oligosaccharide composition.

Generally, the catalyst and the dextrose preparation are introduced into an interior chamber of a reactor, either concurrently or sequentially. Oligosaccharide synthesis can be performed in a batch process or a continuous process. For example, in one embodiment, glycan polymer synthesis is performed in a batch process, where the contents of the reactor are continuously mixed or blended, and all or a substantial amount of the products of the reaction are removed (e.g. isolated and/or recovered). In one variation, glycan polymer synthesis is performed in a batch process, where the contents of the reactor are initially intermingled or mixed but no further physical mixing is performed. In another variation, glycan polymer synthesis is performed in a batch process, wherein once further mixing of the contents, or periodic mixing of the contents of the reactor, is performed (e.g., at one or more times per hour), all or a substantial amount of the products of the reaction are removed (e.g. isolated and/or recovered) after a certain period of time.

In other embodiments, oligosaccharide synthesis is performed in a continuous process, where the contents flow through the reactor with an average continuous flow rate. After introduction of the catalyst and glucose into the reactor, the contents of the reactor are continuously or periodically mixed or blended, and after a period of time, less than all of the products of the reaction are removed (e.g. isolated and/or recovered). In one variation, glycan polymer synthesis is performed in a continuous process, where the mixture containing the catalyst and glucose is not actively mixed. Additionally, mixing of catalyst and dextrose may occur as a result of the redistribution of catalysts settling by gravity, or the non-active mixing that occurs as the material flows through a continuous reactor. In another variation, the reactor is continuously fed by a reactant stream, while a product stream is continuously removed from the reactor. In yet another variation, the reactor is operated in steady state, wherein the reactant stream and product stream are held at fixed flow rates. In other variations, a fraction of the reactor contents are continuously pumped through an external recycle loop, e.g. for the purpose of controlling or measuring properties of the reactor contents such as temperature, density, pH, viscosity, water content, and/or chemical composition. In some variations, mixing of the reactor contents is achieved by the action of pumping a fraction of the reactor contents through such an external recycle loop. In a particular variation, the external recycle loop contains an in-line heat exchanger, flash, or blowdown tank. In another variation, the external recycle loop contains a static mixing element or mixing chamber.

In some embodiments of methods provided herein, the starting material for the polymerization reaction is one or more monosaccharides, one or more disaccharides, one or more trisaccharides, one or more oligosaccharides, or a combination thereof. For example, the starting material for the polymerization reaction can be a dextrose preparation made up of dextrose monomers, dextrose dimers, and/or dextrose trimers. In some embodiments, the starting material for the polymerization reaction is dextrose monohydrate. In some embodiments, the starting material for the polymerization reaction is one or more glucose monomer, dimer, and/or trimer. In some embodiments of the method, the starting material for the polymerization reaction is a furanose sugar and/or a pyranose sugar. In some embodiments of the method, the starting material for the polymerization reaction is one or more glycan units selected from a tetrose, a pentose, a hexose, or a heptose. In some embodiments of the method, the starting material for the polymerization reaction is a glucose, optionally in either its L- or D-form, in alpha or beta configuration (for glucose dimers), and/or a deoxy-form, where applicable, and any combination thereof. In some embodiments, the glucose is substituted or derivatized with one or more of an acetate ester, sulfate half-ester, phosphate ester, or a pyruvyl cyclic acetal group, or have been otherwise derivatized at, e.g., at one or more hydroxyl groups.

In some embodiments, the starting material for the polymerization reaction is a starch hydrolysate, such as a glucose syrup, corn syrup, or mixtures thereof. In some embodiments, the starting material for the polymerization reaction is a dextrose syrup. In some embodiments, the starting material can be a syrup chosen from any syrup within a range of dextrose equivalent (DE) syrups, e.g., a syrup chosen from 20-99DE syrups.

In one embodiment, the glucose (e.g., dextrose) used in the methods described herein can be one or more C5 or C6 monosaccharides. In some embodiments, the glucose is a C5 monosaccharide. In some embodiments, the glucose is a C6 monosaccharide.

In some embodiments, the starting material for the polymerization reaction is one or more glycan units selected from an amino sugar, a deoxy sugar, an imino sugar, a sugar acid, a sugar amide, a sugar ether, a short-chained fatty acid, a sugar alcohol, or any combination therof.

In some embodiments, to obtain a purified oligosaccharide composition, the composition can be separated from the acid catalyst, for example, by diluting the quenched reaction mixture with water to a concentration of about 5-65 weight percent and then passing the mixture through a series of chromatographic resins. This series of chromatographic resins can involve a cationic exchange resin, followed by an anionic exchange resin, and finishing with a decolorizing polymer resin. In some embodiments, any or all of the types of resins may be used one or more times in any order.

For some applications, it is desirable to reduce the level of residual saccharide monomers below that achieved during synthesis, for example, from about 20% to less than 10% (e.g., less than 5%, less than 2%, or less than 1% monomer). In some embodiments, oligosaccharide compositions may be de-monomerized. In some embodiments, de-monomerization involves the removal of residual saccharide monomers from the oligosaccharide compositions. A variety of methods may be used to remove monomeric sugars from oligosaccharide preparations, such as, for example, fractional precipitations, membrane separations, chromatographic separations, and fermentation. See, e.g., Sen, et al., 2011, Food Chem., 128(3), 773-777; Pinelo, et al., 2009, Separation Purification Technol., 70, 1-11; Vanneste, et al., 2011, Separation Purification Technol., 80, 600-609; and Guerrero, et al., 2014, Int. Dairy J., 39, 78-88, which are all incorporated by reference herein. These de-monomerization methods may be used alone or in combination to reduce the level of monomers in an oligosaccharide preparation. In some embodiments, de-monomerization is performed using chromatographic resin. Accordingly, in some embodiments, different compositions can be prepared depending upon the percent of monomer present. In some embodiments, the oligosaccharide composition is de-monomerized to a monomer content of about 1%, about 3%, about 5%, about 10%, or about 15%. In one embodiment, the oligosaccharide composition is de-monomerized to a monomer content of less than 1%. In one embodiment, the oligosaccharide composition is de-monomerized to a monomer content between about 12% and 18%. In one embodiment, the oligosaccharide composition is de-monomerized to a monomer content between about 13% and 17%. In some embodiments, de-monomerization is achieved by osmotic separation. In some embodiments, de-monomerization is achieved by tangential flow filtration (TFF). In some embodiments, de-monomerization is achieved by ethanol precipitation.

In some embodiments, oligosaccharide compositions with different monomer contents may also have different measurements for total dietary fiber, moisture, total dietary fiber (dry basis), or percent DE, as reflected in Table 2.

or 16 and 24 (dry basis). In some embodiments, the oligosaccharide composition has a total dietary fiber (dry basis) of at least 70%, e.g., 70% to 99% (dry basis). In some embodiments, the oligosaccharide composition has a total dietary fiber content of at least 70% (dry basis), at least 80%, at least 90%, at least 95%, or at least 99%. In some embodiments, the oligosaccharide composition comprises soluble dietary fiber precipitate (SDFP) that is below the limits of quantification. In some embodiments, the oligosaccharide composition comprises insoluble dietary fiber (IDF) that is below the limits of quantification. In some embodiments, the oligosaccharide composition comprises high molecular weight dietary fiber (HMWDF), which is the SDFP and the IDF, that is below the limits of quantification. In some embodiments, production of oligosaccharides compositions according to methods provided herein can be performed in a batch process or a continuous process. For example, in one embodiment, oligosaccharide compositions are produced in a batch process, where the contents of the reactor are subjected to agitation conditions (e.g., continuously mixed or blended), and all or a substantial amount of the products of the reaction are removed (e.g., isolated and/or recovered).

In certain embodiments, the methods of using the catalyst are carried out in an aqueous environment. One suitable aqueous solvent is water, which may be obtained from various sources. Generally, water sources with lower concentrations of ionic species (e.g., salts of sodium, phosphorous, ammonium, or magnesium) may be used, in some embodiments, as such ionic species may reduce effectiveness of the catalyst. In some embodiments where the aque-

TABLE 2

Effect of De-monomerization on Oligosaccharide Composition Characteristics

| | Method of analysis | Unmodified Composition (~12-15% monomer) | Composition w/<1% monomer | Composition w/3% monomer | Composition w/5% monomer | Composition w/10% monomer |
|---|---|---|---|---|---|---|
| Total Dietary Fiber | AOAC 2011.25 | 70.7% | 90.5% | 90.5% | 88.7% | 77.4% |
| Moisture | Vaccum Oven @ 60 C. | 4.0% | 1.8% | 2.7% | 2.9% | 6.9% |
| Total Dietary Fiber (dry basis) | Calculated | 73.6% | 92.1% | 93.0% | 91.3% | 83.1% |
| Reducing Sugar Content (% DE, dry basis) | FCC | 27.3% | 13.9% | 17.6% | 19.0% | 23.6% |

In some embodiments, total dietary fiber is measured according to the methods of AOAC 2011.25. In some embodiments, moisture is measured by using a vacuum oven at 60° C. In some embodiments, total dietary fiber is (dry basis) is calculated. In some embodiments, the percent Dextrose Equivalent (DE) (dry basis) is measured according to the Food Chemicals Codex (FCC).

In some embodiments, the oligosaccharide composition is de-monomerized, e.g., by the methods described in Example 9. In some embodiments, the oligosaccharide composition has about 13 to 27 percent DE (dry basis), about 18 to 28 percent DE (dry basis), about 16 to 24 percent (dry basis), or 20 to 26 percent (dry basis). In some embodiments, the oligosaccharide composition has a DE of between 15 and 25, ous solvent is water, the water has less than 10% of ionic species (e.g., salts of sodium, phosphorous, ammonium, magnesium). In some embodiments where the aqueous solvent is water, the water has a resistivity of at least 0.1 megaohm-centimeters, of at least 1 megaohm-centimeters, of at least 2 megaohm-centimeters, of at least 5 megaohm-centimeters, or of at least 10 megaohm-centimeters. In some embodiments, as reactions described herein progress, water (such as evolved water) is produced with each glycosidic coupling, e.g., between two or more saccharide monomers. In certain embodiments, the methods described herein may further include monitoring the amount of water present in the reaction mixture and/or the ratio of water to monomer or catalyst over a period of time. Thus, in some embodiments, the water content of the reaction mixture may be altered over the course of the reaction, for example, by removing evolved water that is produced. Appropriate methods may be used to remove water (e.g., evolved water) in the reaction mixture, including, for example, by evaporation, such as via distillation. In some embodiments, the method comprises including water in the reaction mixture. In certain embodiments, the method comprises removing water from the reaction mixture through evaporation.

In some embodiments, water is added to the reaction mixture to quench the reaction by bringing the temperature of the reaction mixture to 100° C. or below. In some embodiments, the added water is deionized water. In some embodiments, the added water has a temperature of about 60° C. to about 100° C. In some embodiments, the water is added to the reaction mixture under conditions sufficient to avoid solidifying the mixture.

The viscosity of the reaction mixture may be measured and/or altered over the course of the reaction. In general, viscosity refers to a measurement of a fluid's internal resistance to flow (e.g., "thickness") and is expressed in centipoise (cP) or pascal-seconds. In some embodiments, the viscosity of the reaction mixture is between about 100 cP and about 95,000 cP, about 5,000 cP and about 75,000 cP, about 5,000 and about 50,000 cP, or about 10,000 and about 50,000 cP. In certain embodiments, the viscosity of the reaction mixture is between about 50 cP and about 200 cP.

In some embodiments, oligosaccharide compositions provided herein may be subjected to one or more additional processing steps. Additional processing steps may include, for example, purification steps. Purification steps may include, for example, separation, demonomerization, dilution, concentration, filtration, desalting or ion-exchange, chromatographic separation, or decolorization, or any combination thereof.

In some embodiments, the methods described herein further include a decolorization step. The one or more oligosaccharide compositions produced may undergo a decolorization step using appropriate methods, including, for example, treatment with an absorbent, activated carbon, chromatography (e.g., using ion exchange resin), and/or filtration (e.g., microfiltration).

In some embodiments, the one or more oligosaccharide compositions produced are contacted with a material to remove salts, minerals, and/or other ionic species. For example, in certain embodiments, the one or more oligosaccharide compositions produced are flowed through an anioic exchange column. In other embodiments, oligosaccharide compositions produced are flowed through an anionic/cationic exchange column pair.

In some embodiments, the methods described herein may further include a concentration step. For example, in some embodiments, the oligosaccharide compositions may be subjected to evaporation (e.g., vacuum evaporation) to produce a concentrated oligosaccharide composition. In other embodiments, the oligosaccharide compositions may be subjected to a spray drying step to produce an oligosaccharide powder. In certain embodiments, the oligosaccharide compositions may be subjected to both an evaporation step and a spray drying step. In some embodiments, the oligosaccharide compositions be subjected to a lyophilization (e.g., freeze drying) step to remove water and produce powdered product.

In some embodiments, the methods described herein further include a fractionation step. Oligosaccharide compositions prepared and purified may subsequently separated by molecular weight using any method known in the art, including, for example, high-performance liquid chromatography, adsorption/desorption (e.g. low-pressure activated carbon chromatography), or filtration (for example, ultrafiltration or diafiltration). In certain embodiments, oligosaccharide compositions are separated into pools representing 60%, 65%, 70%, 75%, 80%, 85%, 90%, 95%, 97%, 98%, or greater than 98% short (about DP1-2), medium (about DP3-10), long (about DP11-18), or very long (about DP>18) species.

In certain embodiments, prepared oligosaccharide compositions are fractionated by adsorption onto a carbonaceous material and subsequent desorption of fractions by washing the material with mixtures of an organic solvent in water at a concentration of 1%, 5%, 10%, 20%, 50%, or 100%. In one embodiment, the adsorption material is activated charcoal. In another embodiment, the adsorption material is a mixture of activated charcoal and a bulking agent such as diatomaceous earth or Celite 545 in 5%, 10%, 20%, 30%, 40%, or 50% portion by volume or weight.

In further embodiments, oligosaccharide compositions prepared as described herein are separated by passage through a high-performance liquid chromatography system. In certain variations, prepared oligosaccharide compositions are separated by ion-affinity chromatography, hydrophilic interaction chromatography, or size-exclusion chromatography including gel-permeation and gel-filtration.

In some embodiments, catalyst is removed by filtration. In other embodiments, low molecular weight materials are removed by filtration methods. In certain variations, low molecular weight materials may be removed by dialysis, ultrafiltration, diafiltration, or tangential flow filtration. In certain embodiments, the filtration is performed in a static dialysis tube apparatus. In other embodiments, the filtration is performed in a dynamic flow filtration system. In other embodiments, the filtration is performed in centrifugal force-driven filtration cartridges. In certain embodiments, the reaction mixture is cooled to below about 85° C. before filtering.

Characterization of the Oligosaccharide Composition

In some embodiments, the mean degree of polymerization of all glycans is in a range of 4-10. In some embodiments, the mean degree of polymerization of all glycans is in a range of 4-8, 5-9, 5-8, 5-7, 6-9, 6-8, 4-5, 5-6, 6-7, 7-8, 8-9, or 9-10. In some embodiments, the mean degree of polymerization of all glycans is about 5.5-8.5. In certain embodiments, the mean degree of polymerization of all glycans is about 6. In certain embodiments, the mean degree of polymerization of all glycans is about 7. In some embodiments, the mean degree of polymerization of all glycans is in a range of about 4, about 5, about 6, about 7, about 8, about 9, or about 10.

In some embodiments, the oligosaccharide composition comprises oligosaccharides that have a MWw (g/mol) in a range of 700-1620. In some embodiments, the oligosaccharide composition comprises oligosaccharides that have a MWw (g/mol) in a range of 852-1475. In some embodiments, the oligosaccharide composition comprises oligosaccharides that have a MWw (g/mol) in a range of 850-14500, e.g., 850-1410, 870-1410, 850-1200, 900-1100, or 900-1050. In some embodiments, the oligosaccharide composition comprises oligosaccharides that have a MWw (g/mol) in a range of 1005-1315. In some embodiments, the oligosaccharide composition comprises oligosaccharides that have a MWw (g/mol) in a range of 700-850, 900-1000, 850-1000, 850-1050, 1000-1200, 1200-1400, 1400-1600, or 1500-1620. In some embodiments, the oligosaccharide composition comprises oligosaccharides that have a MWw (g/mol) of about 900, 950, 980, 1000, 1050, 1075, 1100, 1150, or 1200. In some embodiments, the oligosaccharide composition comprises oligosaccharides that have a MWw (g/mol) of about 960 or 1150. In some embodiments, the oligosaccharide composition comprises oligosaccharides that have a MWn (g/mol) in a range of 560-960. In some embodiments, the oligosaccharide composition comprises oligosaccharides that have a MWn (g/mol) in a range of 600-900, e.g., 600-850, 625-860, 650-850, 650-800, 600-700, or 700-800. In some embodiments, the oligosaccharide composition comprises oligosaccharides that have a MWn (g/mol) in a range of 612-912. In some embodiments, the oligosaccharide composition comprises oligosaccharides that have a MWn (g/mol) in a range of 700-820. In some embodiments, the oligosaccharide composition comprises oligosaccharides that have a MWn (g/mol) in a range of 600-700, e.g., 620-700 or 650-700. In some embodiments, the oligosaccharide composition comprises oligosaccharides that have a MWn (g/mol) in a range of 560-700, 600-750, 650-800, 700-850, 850-900, 900-960, or 900-1000.

In some embodiments, the oligosaccharide composition comprises oligomers having two or more monomers (DP2+) in a range of 70-99% weight percent (dry basis), e.g., as determined by, e.g., size exclusion chromatography (SEC), e.g., according to the methods described in Example 11. In some embodiments, the oligosaccharide composition comprises oligomers having two or more monomers (DP2+) in a range of 80-95% weight percent, 80-90% weight percent, 82-95% weight percent, 82-90% weight percent, 83-91% weight percent, 83-89% weight percent, 83-86% weight percent, 83-85% weight percent, 84-89% weight percent, 84-86% weight percent, 85-87% weight percent, 86-89% weight percent, 87-89% weight percent, 88-90% weight percent, or 89-91% weight percent. In some embodiments, the oligosaccharide composition comprises oligomers having two or more monomers (DP2+) in a range of 83-86 weight percent. In some embodiments, the oligosaccharide composition comprises oligomers having two or more monomers (DP2+) in a range of about 80%, about 81%, about 82, about 83, about 84, about 85, about 86, about 87 weight percent, about 88 percent, about 89 percent, or about 90 percent. In some embodiments, the composition comprises about 6% to about 23% monomer (DP1) and/or about 4% to about 12% disaccharide (DP2). In some embodiments, the composition comprises 8% to 17% monomer (DP1) and/or about 6% to about 10% disaccharide (DP2). In some embodiments, the composition comprises about 12% to about 21% monomer (DP1) and/or about 7% to about 12% disaccharide (DP2).

In some embodiments, the oligosaccharide composition comprises glucose (e.g., dextrose) monosaccharides. In some embodiments, the oligosaccharide composition contains no more than 30% monosaccharides or monomers (dry basis), as determined by, e.g., SEC HPLC, e.g., as described in Example 11. In some cases, the oligosaccharide composition contains less than 28% monomers (dry basis), less than 25% monomers, less than 22% monomers, less than 20% monomers, less than 18% monomers, less than 16% monomers, less than 14% monomers, less than 12% monomers, less than 10% monomers, less than 8% monomers, less than 6% monomers, less than 4% monomers, or less than 2% monomers. In some cases, the oligosaccharide composition contains in the range of 12-25% monomers (dry basis), 10-20% monomers, 12-22% monomers, 10-18% monomers, 12-18% monomers, 13-18% monomers, 1-10% monomers, or 5-10% monomers. In some cases, the oligosaccharide composition is de-monomerized, e.g., according to the method described in Example 9. In some cases, the oligosaccharide composition contains less than 5% monomers (dry basis), e.g., less than 4%, less than 2%, or less than 1% monomer. In some cases, the oligosaccharide composition contains 0-5% monomer or 2-5% monomer. In some embodiments, the oligosaccharide composition has a polydispersity index (PDI) of 1.3-1.8, e.g., a PDI of 1.4-1.7 or 1.5-1.7. In some embodiments, the oligosaccharide composition has a PDI of 1.0-1.2, 1.2-1.3, 1.3-1.4, 1.4-1.5, 1.5-1.6, 1.7-1.8, or 1.8-2.0. In some embodiments, the oligosaccharide composition has a PDI of about 1.2, about 1.3, about 1.4, about 1.5, about 1.6, about 1.7, or about 1.8.

In some embodiments, the MWw, MWn, PDI, monomer content (DP1) and/or DP2+ values for oligosaccharides in an oligosaccharide composition are determined using the size exclusion chromatagraphy method described in Example 11.

In some embodiments, the amount of monosaccharides and disaccharides in the oligosaccharide composition is determined using the size exclusion chromatography method described in Example 13. In some embodiments, the monomer (DP1), disaccharide (DP2), and DP3+ content of oligosaccharides in an oligosaccharide composition are determined using the size exclusion chromatagraphy method described in Example 13. In some embodiments, the oligosaccharide composition comprises 5.5% to 24%, monomer (DP1), e.g., 5.61% to 23.21% or 12% to 22% monomer (DP1). In some embodiments, the oligosaccharide composition comprises about 10% to about 20% monomer DP1. In some embodiments, the oligosaccharide composition comprises 5% to 8%, 5% to 10%, 7% to 10%, 10% to 15%, 9% to 12%, 11% to 14%, 15% to 20%, 13% to 16%, 15% to 18%, 12% to 19%, 17% to 20%, 20% to 25%, 19% to 22%, 21% to 24%, or 20% to 23% monomer (DP1). In some embodiments, the oligosaccharide composition comprises 8.27% to 16.89% or 12.34% to 21.39% monomer (DP1). In some embodiments, the oligosaccharide composition comprises 4% to 14% disaccharide (DP2), e.g., 4.45% to 12.30% or 7% to 12% disaccharide (DP2). In some embodiments, the oligosaccharide composition comprises about 6% to about 11% disaccharide (DP2), e.g., 6% to 9%, 7% to 11%, or 8% to 10% disaccharide (DP2). In some embodiments, the oligosaccharide composition comprises 4% to 5%, 5% to 6%, 6% to 7%, 7% to 8%, 8% to 9%, 9% to 10%, 10% to 11%, 11% to 12%, or 12% to 13% disaccharide (DP2). In some embodiments, the oligosaccharide composition comprises 5% to 10%, 5% to 15%, 10% to 15%, or 15% to 20% disaccharide (DP2). In some embodiments, the oligosaccharide composition comprises 5.73% to 9.68% or 6.97% to 11.86% disaccharide (DP2).

In some embodiments, the amounts of impurities in the oligosaccharide compositions described herein are determined by, e.g., SEC HPLC, e.g., as described in Example 12. In some embodiments, the oligosaccharide composition comprises 3.0% total impurities or less (excluding monomer), e.g., less than 3.0%, less than 2.5%, less than 2.0%, less than 1.5%, less than 1.0%, or less than 0.5% impurities. In some embodiments, the oligosaccharide composition comprises less than 0.2% total impurities (excluding monomer). In some embodiments, the oligosaccharide composition comprises less than 0.10% total impurities (excluding monomer). In some embodiments, the oligosaccharide composition comprises less than 0.05% total impurities (excluding monomer). In some embodiments, the oligosaccharide composition comprises less than 0.30%, 0.20%, 0.15%, 0.10%, or 0.05% total impurities (excluding monomer).

In some embodiments, the oligosaccharide composition has 0.2% w/w lactic acid or less (e.g., 0.0-0.05% w/w lactic acid), 0.7% w/w formic acid or less (e.g., 0.05-0.45% w/w formic acid), 0.2% w/w acetic acid or less (e.g., 0.0-0.05% w/w acetic acid), 2.0% w/w levulinic acid or less (e.e., 0.1-0.8% or 0.1-1.5% w/w levulinic acid), 2.0% w/w levoglucosan or less (e.g., 0.0-0.5% or 0.0-1.3% w/w levoglucosan), 1.0% w/w levoglucosan isomer or less (0.0-0.5% w/w levoglucosan isomer), and/or 0.2% w/w hydroxymethylfurfural (HMF) or less (e.g., 0.0-0.05% w/w HMF), or any combination thereof, e.g., any combination of these impurities in the oligosaccharide composition wherein the total impurities in the oligosaccharide composition is 3.0% or less. In some embodiments, the oligosaccharide composition comprises less than 0.1% w/w lactic acid, less than 0.1% w/w formic acid, less than 0.1% w/w acetic acid, and/or less than 0.1% w/w HMF.

In some embodiments, the oligosaccharide composition comprises about 0.01% w/w acetic acid, about 0.2% w/w formic acid, about 0.6% w/w, levulinic acid, and/or about 0.4% levoglucosan. In some embodiments, the oligosaccharide composition comprises 0.00% to 0.03% w/w acetic acid, 0.5% to 0.7% w/w levulinic acid, 0.2% to 0.3% w/w formic acid, and 0.4% to 0.5% levoglucosan. In some embodiments, the oligosaccharide composition does not contain detectable quantities of acetic acid, lactic acid, or HMF, or any combination thereof.

In some embodiments, the oligosaccharide composition comprises between about 0.0% w/w and 1.0% w/w lactic acid (e.g., 0.0-0.05% w/w lactic acid). In some embodiments, the oligosaccharide composition comprises between about 0.0% w/w and 0.5% w/w formic acid (e.g., 0.2-0.3% w/w formic acid). In some embodiments, the oligosaccharide composition comprises between about 0.0% w/w and 0.1% w/w acetic acid (e.g., 0.0-0.05% w/w acetic acid). In some embodiments, the oligosaccharide composition comprises between about 0.0% w/w and 1.2% w/w levulinic acid (e.g., 0.5-0.8% w/w levulinic acid). In some embodiments, the oligosaccharide composition comprises between about 0.0% w/w and 1.0% w/w HMF (e.g., 0.0-0.03% w/w HMF). In some embodiments, the oligosaccharide composition comprises between about 0.0% w/w and 1.3% w/w levoglucosan (e.g., 0.0-0.5% w/w levoglucosan). In some embodiments, the oligosaccharide composition comprises between about 0.0% w/w and 0.6% w/w levoglucosan isomer (e.g., 0.0-0.25% w/w laevoglucosan isomer) In some embodiments, the oligosaccharide composition contains no more than 0.1% w/w lactic acid, e.g., 0.05%, 0.03%, 0.02%, or 0.01% lactic acid or less. In some embodiments, the oligosaccharide composition contains no more than 0.5% w/w formic acid, e.g., 0.4%, 0.3%, 0.2%, or 0.1% formic acid or less. In some embodiments, the oligosaccharide composition contains no more than 0.1% w/w acetic acid, e.g., 0.05%, 0.03%, 0.02%, or 0.01% acetic acid or less. In some embodiments, the oligosaccharide composition contains no more than 1.0% w/w levulinic acid, e.g., 0.8%, 0.7%, 0.6%, 0.5%, 0.4%, 0.3%, 0.2% or 0.1% levulinic acid or less. In some embodiments, the oligosaccharide composition contains no more than 0.1% w/w HMF, e.g., 0.05%, 0.03%, 0.02%, or 0.01% HMF or less. In some embodiments, the oligosaccharide composition contains no more than 0.8% w/w levoglucosan, e.g., 0.8%, 0.7%, 0.6%, 0.5%, 0.45%, 0.4%, 0.3%, 0.2%, or 0.1% levoglucosan or less. In some embodiments, the oligosaccharide composition contains no more than 0.5% w/w levoglucosan isomer, e.g., 0.5%, 0.4%, 0.3%, 0.2%, or 0.1% levoglucosan isomer or less. In some embodiments, the oligosaccharide composition is de-monomerized. In some embodiments, the oligosaccharide composition is not de-monomerized. In some embodiments, the oligosaccharide composition contains 0.0% to 0.4% w/w formic acid (e.g., 0.1% to 0.3% w/w formic acid), 0.3% to 1.0% w/w levulinic acid (e.g., 0.5% to 0.7%), no detectable quantities of lactic acid, no detectable quantities of acetic acid, or no detectable quantities of HMF. In some embodiments, the oligosaccharide composition contains 0.0% to 0.4% w/w formic acid (e.g., 0.1% to 0.3% w/w formic acid), 0.3% to 1.0% w/w levulinic acid (e.g., 0.5% to 0.7%), no detectable quantities of lactic acid, no detectable quantities of acetic acid, and no detectable quantities of HMF.

In some embodiments, the oligosaccharide composition has a total water content of between 20-35% weight percent, e.g., a water content of 22-32%, 25-35%, 24-33%, 26-32%, or 28-30% weight percent.

In some embodiments, the oligosaccharide composition has a pH in the range of 2.5 to 7.5, e.g., 2.5 to 5.0 or 3.0 to 4.0.

Characterization by Permethylation Analysis

The oligosaccharide compositions described herein, and prepared according to methods described herein, can be characterized and distinguished from prior art compositions using permethylation analysis. See, e.g., Zhao, Y., et al. 'Rapid, sensitive structure analysis of oligosaccharides,' PNAS Mar. 4, 1997 94 (5) 1629-1633; Kailemia, M. J., et al. 'Oligosaccharide analysis by mass spectrometry: A review of recent developments,' Anal Chem. 2014 Jan. 7; 86(1): 196-212. Accordingly, in another aspect, oligosaccharide compositions are provided herein that comprise a plurality of oligosaccharides that are minimally digestible by humans, the plurality of oligosaccharides comprising monomer radicals. The molar percentages of different types of monomer radicals in the plurality of oligosaccharides can be quantified using a permethylation assay. In some embodiments, the permethylation assay is performed on a de-monomerized sample of the composition.

In certain embodiments, the plurality of oligosaccharides comprises monomer radicals selected from radicals (1)-(15) of Table 3:

TABLE 3

| Monomer Radicals | | |
|---|---|---|
| No. | Monomer radicals | Structure |
| 1 | 2-glucopyranose | |
| 2 | 6-glucopyranose | |
| 3 | 4-glucopyranose | |

TABLE 3-continued

Monomer Radicals

| No. | Monomer radicals | Structure |
|---|---|---|
| 4 | 3,4-glucopyranose | 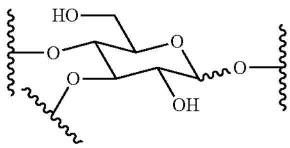 [SMILES: *OC1OC(CO)C(O*)C(O*)C1O] |
| 5 | 2,3-glucopyranose | 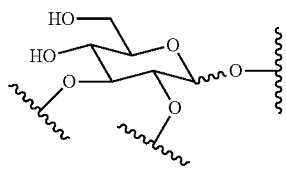 [SMILES: *OC1OC(CO)C(O)C(O*)C1O*] |
| 6 | 3,4,6-glucopyranose | 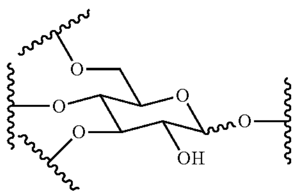 [SMILES: *OCC1OC(O*)C(O)C(O*)C1O*] |
| 7 | 2,4,6-glucopyranose | 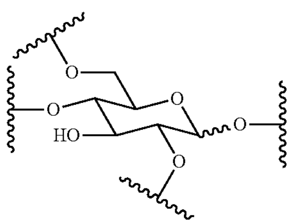 [SMILES: *OCC1OC(O*)C(O*)C(O)C1O*] |
| 8 | t-glucopyranose | 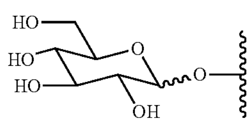 [SMILES: *OC1OC(CO)C(O)C(O)C1O] |
| 9 | 3-glucopyranose | 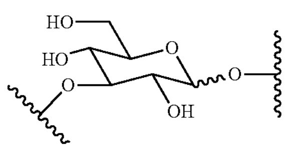 [SMILES: *OC1OC(CO)C(O)C(O*)C1O] |
| 10 | 2,4-glucopyranose | 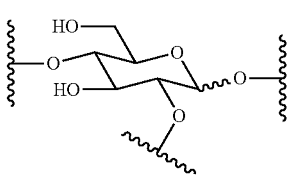 [SMILES: *OC1OC(CO)C(O*)C(O)C1O*] |
| 11 | 2,6-glucopyranose | 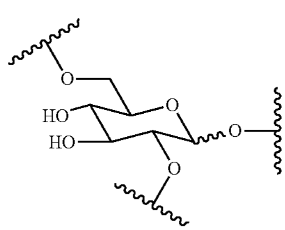 [SMILES: *OCC1OC(O*)C(O*)C(O)C1O] |
| 12 | 2,3,4-glucopyranose/ 4,6-glucopyranose | |
| 13 | 3,6-glucopyranose | |
| 14 | 2,3,6-glucopyranose | |
| 15 | 2,3,4,6-glucopyranose | |

In certain embodiments, the plurality of oligosaccharides comprises two or more monomer radicals selected from radicals (1)-(7):

(1) 2-glucopyranose diradicals, representing 6.8-8.9 mol % of monomer radicals in the plurality of oligosaccharides;

(2) 6-glucopyranose diradicals, representing 20.0-23.5 mol % of monomer radicals in the plurality of oligosaccharides;

(3) 4-glucopyranose diradicals, representing 7.0-8.3 mol % of monomer radicals in the plurality of oligosaccharides;

(4) 3,4-glucopyranose triradicals, representing 0.6-1.3 mol % of monomer radicals in the plurality of oligosaccharides;

(5) 2,3-glucopyranose triradicals, representing 1.5-2.4 mol % of monomer radicals in the plurality of oligosaccharides;

(6) 3,4,6-glucopyranose tetraradicals, representing 0.2-0.9 mol % of monomer radicals in the plurality of oligosaccharides; and (7) 2,4,6-glucopyranose tetraradicals, representing 0.4-0.7 mol % of monomer radicals in the plurality of oligosaccharides.

In certain embodiments, the plurality of oligosaccharides comprises two, three, four, five, six, or seven types of monomer radicals selected from radicals (1)-(7).

In certain embodiments, the plurality of oligosaccharides further comprises one or more types of monomer radicals selected from radicals (8)-(12):
  (8) t-glucopyranose monoradicals, representing 30.9-43 mol % of monomer radicals in the plurality of oligosaccharides;
  (9) 3-glucopyranose diradicals, representing 7.4-8.8 mol % of monomer radicals in the plurality of oligosaccharides;
  (10) 2,4-glucopyranose triradicals, representing 0.7-1.3 mol % of monomer radicals in the plurality of oligosaccharides;
  (11) 2,6-glucopyranose/4,6-glucopyranose triradicals, representing 6.0-8.8 mol % of monomer radicals in the plurality of oligosaccharides; and
  (12) 2,3,4-glucopyranose radicals, representing 0.2-0.7 mol % of monomer radicals in the plurality of oligosaccharides.

In certain embodiments, the plurality of oligosaccharides comprises one, two, three, four, or five types of monomer radicals selected from radicals (8)-(12).

In certain embodiments, the plurality of oligosaccharides further comprises one or more types of monomer radicals selected from radicals (13)-(15):
  (13) 3,6-glucopyranose triradicals, representing 3.0-5.3 mol % of monomer radicals in the plurality of oligosaccharides;
  (14) 2,3,6-glucopyranose tetraradicals, representing 0.2-0.7 mol % of monomer radicals in the plurality of oligosaccharides; and
  (15) 2,3,4,6-glucopyranose pentaradicals, representing 0.1-0.5 mol % of monomer radicals in the plurality of oligosaccharides.

In certain embodiments, the plurality of oligosaccharides comprises one, two, or three types of monomer radicals selected from radicals (13)-(15).

In certain embodiments, the plurality of oligosaccharides comprises the following monomer radicals:
  (1) 2-glucopyranose diradicals, representing 6.8-8.9 mol % of monomer radicals in the plurality of oligosaccharides;
  (2) 6-glucopyranose diradicals, representing 20.0-23.5 mol % of monomer radicals in the plurality of oligosaccharides;
  (3) 4-glucopyranose diradicals, representing 7.0-8.3 mol % of monomer radicals in the plurality of oligosaccharides;
  (4) 3,4-glucopyranose triradicals, representing 0.6-1.3 mol % of monomer radicals in the plurality of oligosaccharides;
  (5) 2,3-glucopyranose triradicals, representing 1.5-2.4 mol % of monomer radicals in the plurality of oligosaccharides;
  (6) 3,4,6-glucopyranose tetraradicals, representing 0.2-0.9 mol % of monomer radicals in the plurality of oligosaccharides;
  (7) 2,4,6-glucopyranose tetraradicals, representing 0.4-0.7 mol % of monomer radicals in the plurality of oligosaccharides;
  (8) t-glucopyranose monoradicals, representing 30.9-43 mol % of monomer radicals in the plurality of oligosaccharides;
  (9) 3-glucopyranose diradicals, representing 7.4-8.8 mol % of monomer radicals in the plurality of oligosaccharides;
  (10) 2,4-glucopyranose triradicals, representing 0.7-1.3 mol % of monomer radicals in the plurality of oligosaccharides;
  (11) 2,6-glucopyranose/4,6-glucopyranose triradicals, representing 6.0-8.8 mol % of monomer radicals in the plurality of oligosaccharides;
  (12) 2,3,4-glucopyranose radicals, representing 0.2-0.7 mol % of monomer radicals in the plurality of oligosaccharides;
  (13) 3,6-glucopyranose triradicals, representing 3.0-5.3 mol % of monomer radicals in the plurality of oligosaccharides;
  (14) 2,3,6-glucopyranose tetraradicals, representing 0.2-0.7 mol % of monomer radicals in the plurality of oligosaccharides; and
  (15) 2,3,4,6-glucopyranose pentaradicals, representing 0.1-0.5 mol % of monomer radicals in the plurality of oligosaccharides.

In a particular embodiment, an oligosaccharide composition is provided, comprising a plurality of oligosaccharides comprising monomer radicals (1)-(15) in the molar percentages shown in Table 4. In certain embodiments, the oligosaccharide composition is de-monomerized, e.g., the oligosaccharide composition comprises 3% glucose (e.g., dextrose) monomers or less (e.g., 2% glucose or dextrose monomers or less).

The defined molar percentage (mol %) range as it pertains to a radical refers to the amount of moles of an individual radical (e.g., a monomer radical) relative to the amount of moles of total radicals in a plurality of oligosaccharides. For example, a mol % of t-glucopyranose radical is determined by dividing the total number of moles of t-glucopyranose radical by the amount of moles of all radicals in a plurality of oligosaccharides.

In some embodiments, mol % of individual radicals is determined after removing radical signals derived from furanoses. In some embodiments, mol % of individual radicals is normalized to demonomerized oligosaccharide.

TABLE 4

Mean mol % of monomer radicals for the selected oligosaccharide composition

| Monomer radical | Mean mol % + 3 STD | Mean mol % + 3 STD | Mean mol % | Mean mol % − 3 STD | Mean mol % − 3 STD |
|---|---|---|---|---|---|
| t-glucopyranose | 46.98% | 42.95% | 36.92% | 30.89% | 26.87% |
| 3-glucopyranose | 9.25% | 8.79% | 8.10% | 7.40% | 6.94% |
| 2-glucopyranose | 9.54% | 8.86% | 7.85% | 6.83% | 6.15% |
| 6-glucopyranose | 24.61% | 23.48% | 21.78% | 20.08% | 18.94% |
| 4-glucopyranose | 8.64% | 8.24% | 7.64% | 7.03% | 6.63% |
| 3,4-glucopyranose | 1.42% | 1.22% | 0.91% | 0.61% | 0.41% |
| 2,3-glucopyranose | 2.59% | 2.33% | 1.93% | 1.54% | 1.28% |
| 2,4-glucopyranose | 1.42% | 1.27% | 1.03% | 0.79% | 0.64% |
| 3,6-glucopyranose | 6.01% | 5.28% | 4.18% | 3.08% | 2.35% |
| 2,6-glucopyranose/ 4,6-glucopyranose | 9.66% | 8.74% | 7.37% | 6.00% | 5.09% |

TABLE 4-continued

Mean mol % of monomer radicals for the selected oligosaccharide composition

| Monomer radical | Mean mol % + 3 STD | Mean mol % + 3 STD | Mean mol % | Mean mol % − 3 STD | Mean mol % − 3 STD |
|---|---|---|---|---|---|
| 2,3,4-glucopyranose | 0.85% | 0.69% | 0.47% | 0.24% | 0.08% |
| 3,4,6-glucopyranose | 1.00% | 0.83% | 0.56% | 0.29% | 0.11% |
| 2,4,6-glucopyranose | 0.72% | 0.64% | 0.52% | 0.41% | 0.33% |
| 2,3,6-glucopyranose | 0.86% | 0.70% | 0.46% | 0.22% | 0.06% |
| 2,3,4,6-glucopyranose | 0.61% | 0.48% | 0.29% | 0.10% | 0.00% |

In certain embodiments, the plurality of oligosaccharides comprises: 30-43 mol % glucopyranose monoradicals; 41-50 mol % glucopyranose diradicals; 12-19 mol % glucopyranose triradicals; and 0.8-3 mol % glucopyranose tetraradicals.

In certain embodiments, the oligosaccharide compositions are free from monomer. In other embodiments, the oligosaccharide compositions comprise monomer. In some embodiments, the oligosaccharide compositions have 5% or less monomer, e.g., 5%, 4%, 3%, 2%, or 1% or less monomer. In some embodiments, the oligosaccharide compositions have 10% or less monomer. In some embodiments, the oligosaccharide compositions have 30% or less monomer, 25% or less, 20% or less, or 18% or less monomer. In some embodiments, the oligosaccharide compositions are de-monomerized, e.g., using the methods described in Example 9.

In some embodiments, the oligosaccharide composition has a percent total branching of about 9% to about 13%, e.g., about 10% to about 12%. In some embodiments, the oligosaccharide composition has a percent total furanose (including terminal) of about 1% to about 4%, e.g., about 2% or about 3%. In some embodiments, the oligosaccharide composition has a percent total terminal sugars of about 42% to about 50%, e.g., about 45% to about 48%.

Characterization by 2DNMR Analysis

The oligosaccharide compositions described herein, and prepared according to methods described herein, can be characterized and distinguished from prior art compositions using two-dimensional heteronuclear NMR. Accordingly, in some embodiments, oligosaccharide compositions are provided that comprise a plurality of oligosaccharides (e.g., that are minimally digestible by humans), the compositions being characterized by a $^{1}H$-$^{13}C$ heteronuclear single quantum coherence (HSQC) NMR spectrum comprising signals 1-14, each signal having a center position and an area, as defined in Table 5. In some embodiments, a signal may be referred to as a peak.

TABLE 5

HSQC NMR signals/peaks belonging to oligosaccharide compositions

| | $^{1}H$ Integral (ppm) | | | $^{13}C$ Position (ppm) | | |
|---|---|---|---|---|---|---|
| | Center | $^{1}H$ Integral Region | | Center | $^{13}C$ Integral Region | |
| Signal | Position | from | to | Position | from | to |
| 1 | 5.39 | 5.4229 | 5.3620 | 100.31 | 99.9518 | 100.6747 |
| 2 | 5.36 | 5.3877 | 5.3310 | 98.48 | 98.2048 | 98.7590 |
| 3 | 5.35 | 5.3971 | 5.2958 | 99.77 | 99.3614 | 100.1807 |
| 4 | 5.22 | 5.2357 | 5.1994 | 102.55 | 102.1205 | 102.9759 |
| 5 | 5.19 | 5.2047 | 5.1684 | 93.95 | 93.6506 | 94.2530 |
| 6 | 5.17 | 5.1933 | 5.1540 | 96.06 | 95.7590 | 96.3614 |
| 7 | 5.1 | 5.1207 | 5.0772 | 96.77 | 96.5181 | 97.0120 |
| 8 | 5.03 | 5.0545 | 5.0009 | 109.19 | 108.7831 | 109.6024 |
| 9 | 4.97 | 5.0194 | 4.9173 | 98.49 | 97.8795 | 99.0964 |
| 10 | 4.8 | 4.8197 | 4.7827 | 96.77 | 96.5904 | 96.9518 |
| 11 | 4.71 | 4.7641 | 4.6658 | 103.64 | 103.2169 | 104.0723 |
| 12 | 4.64 | 4.6670 | 4.6193 | 103.54 | 103.1807 | 103.9036 |
| 13 | 4.63 | 4.6514 | 4.6008 | 104.53 | 104.2289 | 104.8313 |
| 14 | 4.52 | 4.5841 | 4.4476 | 103.34 | 102.8193 | 103.8675 |

In certain embodiments, the spectrum comprises signals 1, 3, and 4, each signal having a center position and an area:

| | Center Position (ppm) | | Area under the curve (AUC) (% of total areas of | Glycosidic |
|---|---|---|---|---|
| Signal | $^{1}H$ | $^{13}C$ | signals of Table 5) | Bond Type |
| 1 | 5.39 | 100.31 | 2.77-5.95 | alpha-1,4 |
| 3 | 5.35 | 99.77 | 4.99-10.49 | alpha-1,3 |
| 4 | 5.22 | 102.55 | 0.00-1.33 | — |

In certain embodiments, signals 1, 3, and 4 are defined as follows:

| | Center Position (ppm) | | Area under the curve (AUC) (% of total areas of | Glycosidic |
|---|---|---|---|---|
| Signal | $^{1}H$ | $^{13}C$ | signals of Table 5) | Bond Type |
| 1 | 5.39 | 100.31 | 3.61-5.11 | alpha-1,4 |
| 3 | 5.35 | 99.77 | 6.16-9.31 | alpha-1,3 |
| 4 | 5.22 | 102.55 | 0.09-0.92 | — |

In certain embodiments, signals 1, 3, and 4 are defined as follows:

| | Center Position (ppm) | | Area under the curve (AUC) (% of total areas of | Glycosidic |
|---|---|---|---|---|
| Signal | $^{1}H$ | $^{13}C$ | signals of Table 5) | Bond Type |
| 1 | 5.39 | 100.31 | 3.37-4.78 | alpha-1,4 |
| 3 | 5.35 | 99.77 | 6.64-8.71 | alpha-1,3 |
| 4 | 5.22 | 102.55 | 0.00-0.95 | — |

In certain embodiments, signals 1, 3, and 4 are defined as follows:

| | Center Position (ppm) | | Area under the curve (AUC) (% of total areas of | Glycosidic |
|---|---|---|---|---|
| Signal | $^{1}H$ | $^{13}C$ | signals of Table 5) | Bond Type |
| 1 | 5.39 | 100.31 | 3.61-4.56 | alpha-1,4 |
| 3 | 5.35 | 99.77 | 6.91-8.29 | alpha-1,3 |
| 4 | 5.22 | 102.55 | 0.07-0.74 | — |

In certain embodiments, signals 1, 3, and 4 are defined as follows:

| Signal | Center Position (ppm) $^1$H | Center Position (ppm) $^{13}$C | Area under the curve (AUC) (% of total areas of signals of Table 5) | Glycosidic Bond Type |
|---|---|---|---|---|
| 1 | 5.39 | 100.31 | 3.84-4.31 | alpha-1,4 |
| 3 | 5.35 | 99.77 | 7.33-8.02 | alpha-1,3 |
| 4 | 5.22 | 102.55 | 0.23-0.62 | — |

In certain embodiments, signals 1, 3, and 4 are defined as follows:

| Signal | Center Position (ppm) $^1$H | Center Position (ppm) $^{13}$C | Area under the curve (AUC) (% of total areas of signals of Table 5) | Glycosidic Bond Type |
|---|---|---|---|---|
| 1 | 5.39 | 100.31 | 3.91-4.21 | alpha-1,4 |
| 3 | 5.35 | 99.77 | 7.33-7.50 | alpha-1,3 |
| 4 | 5.22 | 102.55 | 0.23-0.47 | — |

In certain embodiments, the spectrum further comprises 1-2 (e.g., one or two) signals selected from signals 8 and 9:

| Signal | Center Position (ppm) $^1$H | Center Position (ppm) $^{13}$C | Area under the curve (AUC) (% of total areas of signals of Table 5) | Glycosidic Bond Type |
|---|---|---|---|---|
| 8 | 5.03 | 93.95 | 0.00-2.03 | — |
| 9 | 4.97 | 98.49 | 25.01-40.83 | alpha-1,6 |

In certain embodiments, the spectrum further comprises 1-2 (e.g., one or two) signals selected from signals 8 and 9:

| Signal | Center Position (ppm) $^1$H | Center Position (ppm) $^{13}$C | Area under the curve (AUC) (% of total areas of signals of Table 5) | Glycosidic Bond Type |
|---|---|---|---|---|
| 8 | 5.03 | 93.95 | 0.06-1.38 | — |
| 9 | 4.97 | 98.49 | 28.93-36.91 | alpha-1,6 |

In certain embodiments, signals 8 and 9 are defined as follows:

| Signal | Center Position (ppm) $^1$H | Center Position (ppm) $^{13}$C | Area under the curve (AUC) (% of total areas of signals of Table 5) | Glycosidic Bond Type |
|---|---|---|---|---|
| 8 | 5.03 | 93.95 | 0.00-0.89 | — |
| 9 | 4.97 | 98.49 | 32.69-40.14 | alpha-1,6 |

In certain embodiments, signals 8 and 9 are defined as follows:

| Signal | Center Position (ppm) $^1$H | Center Position (ppm) $^{13}$C | Area under the curve (AUC) (% of total areas of signals of Table 5) | Glycosidic Bond Type |
|---|---|---|---|---|
| 8 | 5.03 | 93.95 | 0.00-0.61 | — |
| 9 | 4.97 | 98.49 | 33.79-38.81 | alpha-1,6 |

In certain embodiments, signals 8 and 9 are defined as follows:

| Signal | Center Position (ppm) $^1$H | Center Position (ppm) $^{13}$C | Area under the curve (AUC) (% of total areas of signals of Table 5) | Glycosidic Bond Type |
|---|---|---|---|---|
| 8 | 5.03 | 93.95 | 0.20-0.55 | — |
| 9 | 4.97 | 98.49 | 35.19-37.63 | alpha-1,6 |

In certain embodiments, signals 8 and 9 are defined as follows:

| Signal | Center Position (ppm) $^1$H | Center Position (ppm) $^{13}$C | Area under the curve (AUC) (% of total areas of signals of Table 5) | Glycosidic Bond Type |
|---|---|---|---|---|
| 8 | 5.03 | 93.95 | 0.20-0.37 | — |
| 9 | 4.97 | 98.49 | 35.19-36.61 | alpha-1,6 |

In certain embodiments, the spectrum further comprises 1-6 (e.g., 1, 2, 3, 4, 5, or 6) signals selected from signals 6, 7, 11, 12, 13, and 14:

| Signal | Center Position (ppm) $^1$H | Center Position (ppm) $^{13}$C | Area under the curve (AUC) (% of total areas of signals of Table 5) | Glycosidic Bond Type |
|---|---|---|---|---|
| 6 | 5.17 | 96.06 | 0.11-1.84 | — |
| 7 | 5.1 | 96.77 | 0.35-2.33 | alpha-1,2-alpha |
| 11 | 4.71 | 103.64 | 4.45-9.84 | beta-1,3 |
| 12 | 4.64 | 103.54 | 1.13-4.01 | beta-1-alpha-1' |
| 13 | 4.63 | 104.53 | 1.31-3.72 | beta-1,2-alpha |
| 14 | 4.52 | 103.34 | 25.65-40.25 | beta-1,4/beta-1,6 co-peak |

In certain embodiments, signals 6, 7, 11, 12, 13, and 14 are defined as follows:

| Signal | Center Position (ppm) $^1$H | $^{13}$C | Area under the curve (AUC) (% of total areas of signals of Table 5) | Glycosidic Bond Type |
|---|---|---|---|---|
| 6 | 5.17 | 96.06 | 0.57-1.38 | — |
| 7 | 5.1 | 96.77 | 0.88-1.80 | alpha-1,2-alpha |
| 11 | 4.71 | 103.64 | 5.80-8.49 | beta-1,3 |
| 12 | 4.64 | 103.54 | 1.85-3.28 | beta-1-alpha-1' |
| 13 | 4.63 | 104.53 | 1.92-3.12 | beta-1,2-alpha |
| 14 | 4.52 | 103.34 | 29.59-36.31 | beta-1,4/beta-1,6 co-peak |

In certain embodiments, signals 6, 7, 11, 12, 13, and 14 are defined as follows:

| Signal | Center Position (ppm) $^1$H | $^{13}$C | Area under the curve (AUC) (% of total areas of signals of Table 5) | Glycosidic Bond Type |
|---|---|---|---|---|
| 6 | 5.17 | 96.06 | 0.26-1.55 | — |
| 7 | 5.1 | 96.77 | 0.65-2.30 | alpha-1,2-alpha |
| 11 | 4.71 | 103.64 | 6.78-8.16 | beta-1,3 |
| 12 | 4.64 | 103.54 | 1.23-3.20 | beta-1-alpha-1' |
| 13 | 4.63 | 104.53 | 1.80-3.09 | beta-1,2-alpha |
| 14 | 4.52 | 103.34 | 28.46-32.06 | beta-1,4/beta-1,6 co-peak |

In certain embodiments, signals 6, 7, 11, 12, 13, and 14 are defined as follows:

| Signal | Center Position (ppm) $^1$H | $^{13}$C | Area under the curve (AUC) (% of total areas of signals of Table 5) | Glycosidic Bond Type |
|---|---|---|---|---|
| 6 | 5.17 | 96.06 | 0.54-1.39 | — |
| 7 | 5.1 | 96.77 | 0.92-2.03 | alpha-1,2-alpha |
| 11 | 4.71 | 103.64 | 7.04-7.97 | beta-1,3 |
| 12 | 4.64 | 103.54 | 1.55-2.93 | beta-1-alpha-1' |
| 13 | 4.63 | 104.53 | 2.09-2.92 | beta-1,2-alpha |
| 14 | 4.52 | 103.34 | 29.16-31.40 | beta-1,4/beta-1,6 co-peak |

In certain embodiments, signals 6, 7, 11, 12, 13, and 14 are defined as follows:

| Signal | Center Position (ppm) $^1$H | $^{13}$C | Area under the curve (AUC) (% of total areas of signals of Table 5) | Glycosidic Bond Type |
|---|---|---|---|---|
| 6 | 5.17 | 96.06 | 0.69-1.13 | — |
| 7 | 5.1 | 96.77 | 1.21-1.75 | alpha-1,2-alpha |
| 11 | 4.71 | 103.64 | 7.25-7.70 | beta-1,3 |
| 12 | 4.64 | 103.54 | 1.92-2.51 | beta-1-alpha-1' |
| 13 | 4.63 | 104.53 | 2.22-2.68 | beta-1,2-alpha |
| 14 | 4.52 | 103.34 | 29.58-30.95 | beta-1,4/beta-1,6 co-peak |

In certain embodiments, signals 6, 7, 11, 12, 13, and 14 are defined as follows:

| Signal | Center Position (ppm) $^1$H | $^{13}$C | Area under the curve (AUC) (% of total areas of signals of Table 5) | Glycosidic Bond Type |
|---|---|---|---|---|
| 6 | 5.17 | 96.06 | 0.79-1.12 | — |
| 7 | 5.1 | 96.77 | 1.35-1.75 | alpha-1,2-alpha |
| 11 | 4.71 | 103.64 | 7.25-7.62 | beta-1,3 |
| 12 | 4.64 | 103.54 | 2.31-2.51 | beta-1-alpha-1' |
| 13 | 4.63 | 104.53 | 2.41-2.67 | beta-1,2-alpha |
| 14 | 4.52 | 103.34 | 29.58-30.95 | beta-1,4/beta-1,6 co-peak |

In certain embodiments, the spectrum further comprises 1-3 signals selected from signals 2, 5, and 10:

| Signal | Center Position (ppm) $^1$H | $^{13}$C | Area under the curve (AUC) (% of total areas of signals of Table 5) | Glycosidic Bond Type |
|---|---|---|---|---|
| 2 | 5.36 | 98.48 | 0.00-2.47 | alpha-1,2-beta |
| 5 | 5.19 | 93.95 | 0.00-4.17 | alpha-1-alpha-1' |
| 10 | 4.8 | 96.77 | 0.00-1.95 | beta-1,2-beta, reducing |

In certain embodiments, the spectrum further comprises 1-3 signals selected from signals 2, 5, and 10:

| Signal | Center Position (ppm) $^1$H | $^{13}$C | Area under the curve (AUC) (% of total areas of signals of Table 5) | Glycosidic Bond Type |
|---|---|---|---|---|
| 2 | 5.36 | 98.48 | 0.30-1.84 | alpha-1,2-beta |
| 5 | 5.19 | 93.95 | 0.22-3.00 | alpha-1-alpha-1' |
| 10 | 4.8 | 96.77 | 0.33-1.46 | beta-1,2-beta, reducing |

In certain embodiments, signals 2, 5, and 10 are defined as follows:

| Signal | Center Position (ppm) $^1$H | $^{13}$C | Area under the curve (AUC) (% of total areas of signals of Table 5) | Glycosidic Bond Type |
|---|---|---|---|---|
| 2 | 5.36 | 98.48 | 0.69-1.78 | alpha-1,2-beta |
| 5 | 5.19 | 93.95 | 1.56-4.45 | alpha-1-alpha-1' |
| 10 | 4.8 | 96.77 | 0.26-1.35 | beta-1,2-beta, reducing |

In certain embodiments, signals 2, 5, and 10 are defined as follows:

| Signal | Center Position (ppm) $^1$H | $^{13}$C | Area under the curve (AUC) (% of total areas of signals of Table 5) | Glycosidic Bond Type |
|---|---|---|---|---|
| 2 | 5.36 | 98.48 | 0.85-1.57 | alpha-1,2-beta |
| 5 | 5.19 | 93.95 | 2.08-3.89 | alpha-1-alpha-1' |
| 10 | 4.8 | 96.77 | 0.48-1.19 | beta-1,2-beta, reducing |

In certain embodiments, signals 2, 5, and 10 are defined as follows:

| Signal | Center Position (ppm) $^1$H | Center Position (ppm) $^{13}$C | Area under the curve (AUC) (% of total areas of signals of Table 5) | Glycosidic Bond Type |
|---|---|---|---|---|
| 2 | 5.36 | 98.48 | 1.05-1.43 | alpha-1,2-beta |
| 5 | 5.19 | 93.95 | 2.47-3.54 | alpha-1-alpha-1' |
| 10 | 4.8 | 96.77 | 0.61-1.00 | beta-1,2-beta, reducing |

In certain embodiments, signals 2, 5, and 10 are defined as follows:

| Signal | Center Position (ppm) $^1$H | Center Position (ppm) $^{13}$C | Area under the curve (AUC) (% of total areas of signals of Table 5) | Glycosidic Bond Type |
|---|---|---|---|---|
| 2 | 5.36 | 98.48 | 1.13-1.43 | alpha-1,2-beta |
| 5 | 5.19 | 93.95 | 3.02-3.54 | alpha-1-alpha-1' |
| 10 | 4.8 | 96.77 | 0.85-1.00 | beta-1,2-beta, reducing |

In certain embodiments, signals 1-14 are defined as follows:

| Signal | Center Position (ppm) $^1$H | Center Position (ppm) $^{13}$C | Area under the curve (AUC) (% of total areas of signals of Table 5) | Glycosidic Bond Type |
|---|---|---|---|---|
| 1 | 5.39 | 100.31 | 3.89-4.37 | alpha-1,4 |
| 2 | 5.36 | 98.48 | 1.06-1.45 | alpha-1,2-beta |
| 3 | 5.35 | 99.77 | 7.45-8.11 | alpha-1,3 |
| 4 | 5.22 | 102.55 | 0.23-0.62 | — |
| 5 | 5.19 | 93.95 | 2.50-3.60 | alpha-1-alpha-1' |
| 6 | 5.17 | 96.06 | 0.70-1.14 | — |
| 7 | 5.1 | 96.77 | 1.22-1.77 | alpha-1,2-alpha |
| 8 | 5.03 | 109.19 | 0.20-0.56 | — |
| 9 | 4.97 | 98.49 | 35.74-38.04 | alpha-1,6 |
| 10 | 4.8 | 96.77 | 0.62-1.02 | beta-1,2-beta, reducing |
| 11 | 4.71 | 103.64 | 7.35-7.78 | beta-1,3 |
| 12 | 4.64 | 103.54 | 1.94-2.55 | beta-1-alpha-1' |
| 13 | 4.63 | 104.53 | 2.24-2.72 | beta-1,2-alpha |
| 14 | 4.52 | 103.34 | 29.98-31.33 | beta-1,4/beta-1,6 co-peak |

In certain embodiments, signals 1-14 are defined as follows:

| Signal | Center Position (ppm) $^1$H | Center Position (ppm) $^{13}$C | Area under the curve (AUC) (% of total areas of signals of Table 5) | Glycosidic Bond Type |
|---|---|---|---|---|
| 1 | 5.39 | 100.31 | 3.61-4.56 | alpha-1,4 |
| 2 | 5.36 | 98.48 | 0.85-1.57 | alpha-1,2-beta |
| 3 | 5.35 | 99.77 | 6.91-8.29 | alpha-1,3 |
| 4 | 5.22 | 102.55 | 0.07-0.74 | — |
| 5 | 5.19 | 93.95 | 2.08-3.89 | alpha-1-alpha-1' |
| 6 | 5.17 | 96.06 | 0.54-1.39 | — |
| 7 | 5.1 | 96.77 | 0.92-2.03 | alpha-1,2-alpha |
| 8 | 5.03 | 109.19 | 0.00-0.61 | — |
| 9 | 4.97 | 98.49 | 33.79-38.81 | alpha-1,6 |
| 10 | 4.8 | 96.77 | 0.48-1.19 | beta-1,2-beta, reducing |
| 11 | 4.71 | 103.64 | 7.04-7.97 | beta-1,3 |
| 12 | 4.64 | 103.54 | 1.55-2.93 | beta-1-alpha-1' |
| 13 | 4.63 | 104.53 | 2.09-2.92 | beta-1,2-alpha |
| 14 | 4.52 | 103.34 | 29.16-31.40 | beta-1,4/beta-1,6 co-peak |

In certain embodiments, signals 1-14 are each further characterized by an $^1$H integral region and a $^{13}$C integral region, defined as follows:

| | $^1$H Position (ppm) | | | $^{13}$C Position (ppm) | | |
|---|---|---|---|---|---|---|
| | Center | $^1$H Integral Region | | Center | $^{13}$C Integral Region | |
| Signal | Position | from | to | Position | from | to |
| 1 | 5.39 | 5.4229 | 5.3620 | 100.31 | 99.9518 | 100.6747 |
| 2 | 5.36 | 5.3877 | 5.3310 | 98.48 | 98.2048 | 98.7590 |
| 3 | 5.35 | 5.3971 | 5.2958 | 99.77 | 99.3614 | 100.1807 |
| 4 | 5.22 | 5.2357 | 5.1994 | 102.55 | 102.1205 | 102.9759 |
| 5 | 5.19 | 5.2047 | 5.1684 | 93.95 | 93.6506 | 94.2530 |
| 6 | 5.17 | 5.1933 | 5.1540 | 96.06 | 95.7590 | 96.3614 |
| 7 | 5.1 | 5.1207 | 5.0772 | 96.77 | 96.5181 | 97.0120 |
| 8 | 5.03 | 5.0545 | 5.0009 | 109.19 | 108.7831 | 109.6024 |
| 9 | 4.97 | 5.0194 | 4.9173 | 98.49 | 97.8795 | 99.0964 |
| 10 | 4.8 | 4.8197 | 4.7827 | 96.77 | 96.5904 | 96.9518 |
| 11 | 4.71 | 4.7641 | 4.6658 | 103.64 | 103.2169 | 104.0723 |
| 12 | 4.64 | 4.6670 | 4.6193 | 103.54 | 103.1807 | 103.9036 |
| 13 | 4.63 | 4.6514 | 4.6008 | 104.53 | 104.2289 | 104.8313 |
| 14 | 4.52 | 4.5841 | 4.4476 | 103.34 | 102.8193 | 103.8675 |

In certain embodiments, the NMR spectrum is obtained by subjecting a sample of the composition to heteronuclear single quantum coherence (HSQC) NMR, wherein the sample is a solution in a deuterated solvent. Suitable deuterated solvents in include deuterated acetonitrile, deuterated acetone, deuterated methanol, D$_2$O, and mixtures thereof. In a particular embodiment, the deuterated solvent is D$_2$O.

The area under the curve (AUC) of an individual signal (or peak) is determined using peak integration that is centered around a $^1$H position (ppm) and $^{13}$C position (ppm) relative to the total AUC of all signals of a defined group (e.g., total AUC of all signal positions provided in Table 5). In some embodiments, the total area is the sum of the areas of each of signals 1-14 of Table 5. In some embodiments, the area under the curve (AUC) of each individual signal 1, 2, 3, 4, 5, 6, 7, 8, 9, 10, 11, 12, 13, and/or 14 is defined as a percentage of the total area of signals 1-14 provided in Table 5. In some embodiments, the percentage (%) of total areas of signals 1-14 are provided which represent the percentage that an area of a particular signal is relative to the total areas of signals (e.g., the sum of the areas of each of signals 1-14 of Table 5). In some embodiments, this percentage may be referred to as an area under the curve (AUC) parameter. In some embodiments, such parameters may be specified as a range within which a particular sample or composition falls. In some embodiments, the term "signal" is used interchangeably with the term "peak" when referring to NMR spectra. In some embodiments, the area under the curve for an individual signal or peak is derived from an integral region (e.g., an elliptical integral region). In some embodiments, an integral region (e.g., an elliptical integral region) for an individual signal or peak is defined by the expressed positions (e.g., $^1$H position (ppm) and $^{13}$C position (ppm)) provided in Table 5.

In certain embodiments, the NMR spectrum is obtained as described in Example 10. For example, the NMR spectrum of the composition is obtained by subjecting the sample of the composition to a multiplicity-edited gradient-enhanced $^1$H-$^{13}$C heteronuclear single quantum coherence (HSQC) experiment using the echo-antiecho scheme for coherence selection using the following pulse sequence diagram and acquisition and processing parameters.

Figure 6:
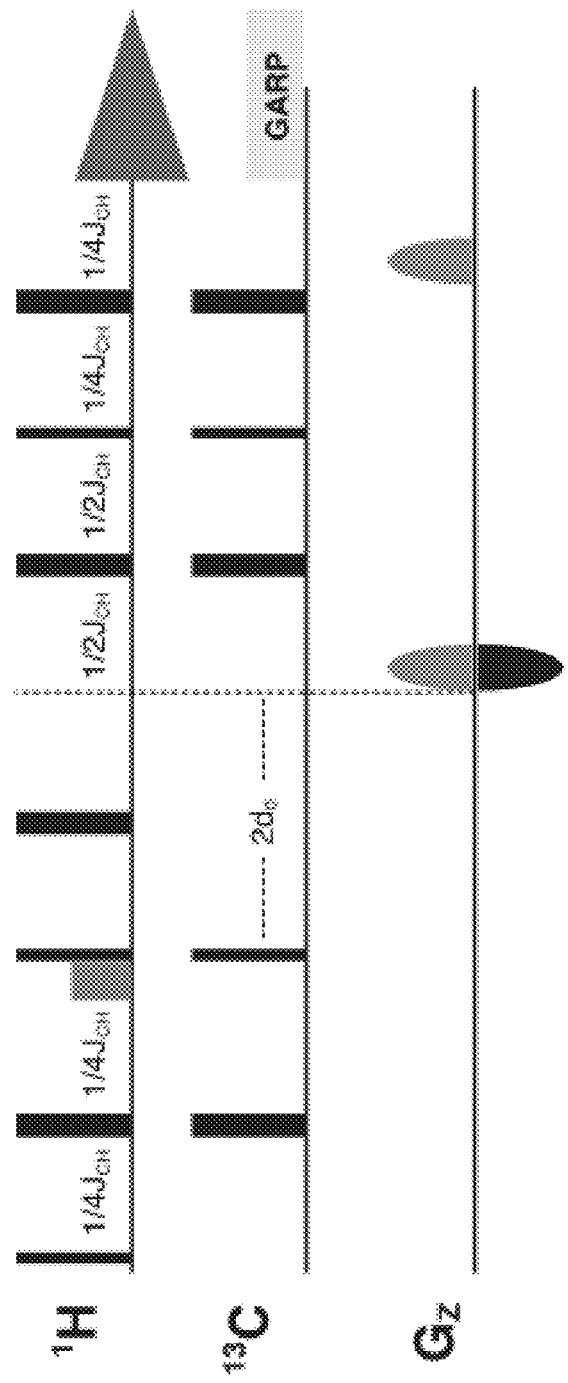
FIG. 6 depicts an NMR pulse sequence diagram.

Pulse sequence diagram as shown in FIG. 6 having
Acquisition Parameters
$^1$H Carrier Frequency=4 ppm
$^{13}$C Carrier Frequency=65 ppm
Number of points in acquisition dimension=596
Spectral range in acquisition dimension=6.00 ppm to 2.03 ppm
Number of points in indirect dimension=300 complex points
Spectral range in indirect dimension=120 ppm to 10 ppm
Recycle delay=1 second
One-bond $^1$H-$^{13}$C coupling constant=$J_{CH}$=146 Hz
Number of scans=8
Temperature=298 K
Solvent=D$_2$O
Processing Parameters
Window function in direct dimension=Gaussian broadening, 7.66 Hz
Window function in indirect dimension=Gaussian broadening 26.48 Hz Processing=512 complex points in direct dimension, 1024 complex points in indirect dimension In certain embodiments, the composition analyzed by NMR contains monosaccharide monomers (DP1), i.e., the DP1 component is not removed from the composition prior to NMR analysis. In certain embodiments, the composition analyzed by NMR is de-monomerized, i.e., the DP1 component of the composition is removed prior to NMR analysis.

III. Methods of Use i. Overview.

As described herein, oligosaccharide compositions (e.g., as described in Examples 1-4), may be used to reduce ammonia levels in a subject, e.g., a subject with elevated ammonia levels. In some embodiments, the oligosaccharide composition is formulated as powder, e.g., for reconstitution (e.g., in water) for oral administration. Accordingly, in some embodiments, methods are provided herein for treating urea cycle disorders (UCDs), which are associated with elevated ammonia levels. In some embodiments, the methods decrease the level of a metabolite, e.g., a metabolite that accumulates in a subject with a UCD. In some embodiments, the methods decrease or increase the prevalence of a microbe or taxa of microbes in a subject, e.g., in the gastrointestinal tract of a subject.

In some embodiments, the urea cycle disorder is associated with carbamyl phosphate synthetase I (CPSI) deficiency, ornithine transcarbamylase (OTC) deficiency, argininosuccinate synthetase (ASS), deficiency, argininosuccinate lyase (ASL) deficiency, N-acetyl glutamate synthetase (NAGS) deficiency, arginase deficiency, ornithine translocase deficiency (HHH), or citrin deficiency (CIT II)) in a subject, e.g., a human subject. In some embodiments, UCD does not include N-acetyl glutamate synthetase (NAGS) deficiency.

In some embodiments, a subject, e.g., patient, with a UCD may present with one or more (e.g., one, two, three, four, five, six, or more) symptoms of UCD. Symptoms of UCDs include neurologic symptoms (e.g., including: decreased level of consciousness, altered mental status, abnormal motor function, and seizures) and gastrointestinal symptoms (e.g., including: vomiting, poor feeding, diarrhea, nausea, constipation, and protein aversion). A subject with UCD may have elevated blood, e.g., plasma, serum, or whole blood, ammonia concentration. In some embodiments, the subject exhibits systemic ammonia levels persistently above 0.5 upper limit of normal. UCD may also be diagnosed with neuroimaging (e.g., MRI). DNA sequencing-based mutation testing and/or next generation sequencing may also be useful to evaluate whether a subject, e.g., patient, has a UCD associated mutation.

In some embodiments, a subject treated according to methods provided herein is undergoing or has undergone (e.g., within the prior year) a standard of care treatment for UCD, which generally includes nitrogen binding therapy or nitrogen-scavenger therapy, dietary (e.g., protein) restriction, and/or hemodialysis. In some embodiments, oligosaccharide compositions may be administered together with a standard of care treatment for UCD, e.g., the oligosaccharide compositions may be administered together with nitrogen binding therapy or nitrogen scavenger therapy.

In some embodiments, a subject with hepatic encephalopathy (HE) may be treated according to the methods provided herein. In some embodiments, the subject has HE as a consequence of liver cirrhosis. In some embodiments, such a subject displays hepatic multiple adverse neurological symptoms that occur when the liver is unable to remove toxic substances such as ammonia from the blood. In some embodiments, the subject has or is suspected of having minimal HE. In some embodiments, the subject has or is suspected of having overt HE. Standard-of-care treatments for overt HE include lactulose, lactitol, and antibiotics (e.g., rifaximin or neomycin). Treatments may also include dietary modifications and probiotics. In some embodiments, such methods result in decreased incidence of future episodes of ammonia crisis, or, in a subject at risk of HE, by decreased occurrence of an initial episode of ammonia crisis.

In some embodiments, the efficacy of a treatment provided herein may be assessed by resolution of the symptoms or diagnostic criteria listed above (e.g., reduction in serum ammonia levels). In some embodiments, one or both of the following is reduced: i) the number of ammonia crises over a period of 1 year (e.g., by at least 1, 2, or at least 3 crises), ii) the severity of complications from ammonia crises, including neurodevelopmental delays and/or cognitive declines (e.g., compared to a suitable control group not receiving the oligosaccharide composition). In some embodiments, the time period between ammonia crises is increased, e.g., by at least 15%, 30%, 60%, 100%, or 200% (e.g., compared to a suitable control group not receiving the oligosaccharide composition).

In some embodiments, administering an oligosaccharide composition (e.g., as produced according to Example 5, 6, or 14) modulates microbes (e.g., a microbial community, e.g., the microbiome) in a subject (e.g., in the gastrointestinal tract of a subject), e.g., a subject having UCD or HE (e.g., MHE or OHE) by modulating (e.g., increasing or decreasing) a microbial enzymatic activity and/or modulating (e.g., increasing or decreasing) a metabolite (e.g., the metabolite accumulating and associated with disease symptoms, e.g., ammonia), e.g., the level of a metabolite. In some embodiments, administering an oligosaccharide composition modulates (e.g., increases or decreases) the level of one or more taxa of microbes within a subject (e.g., the gastrointestinal tract of a subject), e.g., a subject having UCD or HE (e.g., MHE or OHE), effectively modulating (e.g., increasing or decreasing) a microbial enzymatic activity and/or modulating (e.g., increasing or decreasing) a metabolite (e.g., the metabolite accumulating and associated with disease symptoms, e.g., ammonia), e.g., the level of a metabolite.

ii. Ammonia Testing

A subject having, suspected of having, or at risk of having hyperammonemia (e.g., UCDs and hepatic encephalopathy (HE)) may have elevated blood ammonia levels, e.g., plasma ammonia levels, serum ammonia levels, or whole blood ammonia levels, relative to a control subject (e.g., a subject not suspected of having hyperammonemia). In some embodiments, blood ammonia levels in a healthy adult subject (e.g., a subject not suspected of having hyperammonemia) are less than 15, 20, 25, 30, 35, 40, 45, or 50 µmol/L, e.g., less than 30 µmol/L. In some embodiments, a blood ammonia level of about 0.5-fold, about 1-fold, about 1.5-fold, about 2-fold, about 2.5-fold, or about 3-fold above normal is suggestive of UCD or HE. In some embodiments, a subject having or suspected of having UCD or HE has blood ammonia levels of greater than or equal to 90, 95, 100, 105, 110, 115, 120, 125, 130, 135, 140, 145, 150, 155, 160, 165, 170, 175, or 180 µmol/L. In some embodiments, a subject having or suspected of having UCD or HE has blood ammonia levels of greater than or equal to 100, 105, 110, 115, 120, 125, 130, 135, 140, 145, or 150 µmol/L. In some embodiments, a subject having or suspected of having UCD or HE has blood ammonia levels of greater than or equal to 100 µmol/L. In some embodiments, a subject having or suspected of having UCD or HE has blood ammonia levels of greater than or equal to 150 µmol/L.

Newborns and children having, suspected of having, or at risk of having hyperammonemia (e.g., UCDs and hepatic encephalopathy, HE) may have elevated blood ammonia levels, e.g., plasma ammonia levels, serum ammonia levels, or whole blood ammonia levels, relative to a healthy newborn or child. In some embodiments, a healthy newborn or child has an average blood ammonia concentration of 45±10 µmol/L. In some embodiments, a healthy newborn or child (e.g., a subject not suspected of having hyperammonemia) has an average blood ammonia concentration of less than or equal to 70, 71, 72, 73, 74, 75, 76, 77, 78, 79, 80, 81, 82, 83, 84, 85, 86, 87, 87, 88, 89, 90, 91, 92, 93, 94, or 95 µmol/L, e.g., 80 or 90 µmol/L. In some embodiments, a newborn or child having or suspected of having UCD or HE has blood ammonia levels of greater than or equal to 55, 60, 65, 70, 75, 80, 90, or 95, 100, 105, 110, 115, 120, 125, 130, 135, 140, 145, 150, 155, 160, 165, 170, 175, or 180 µmol/L.

In some embodiments, blood ammonia concentration may be measured in venous and arterial blood samples. In some embodiments, measuring serum ammonia levels may be used for monitoring efficacy of glycan preparations described herein. For example, in some embodiments, the serum ammonia level is measured in a subject, e.g., a subject with elevated serum ammonia levels, at least one time point prior to administering an oligosaccharide composition described herein and at least one time point after the oligosaccharide composition is administered, e.g., one or more of 3 hours, 6 hours, 9 hours, 12 hours, 18 hours, 24 hours, 36 hours, 2 days, 3 days, 4 days, 5 days, 7 days, 10 days, 12 days, 14 days, 21 days, 30 days, or 45 days or more after the oligosaccharide composition is administered. A decrease in serum ammonia levels at a time point after the oligosaccharide composition is administered relative to at a time point before the oligosaccharide composition was administered indicates that the composition exhibits efficacy.

In some embodiments, the grade or severity of hyperammonemia may be assessed by measuring the partial pressure of gaseous ammonia (pNH3), e.g., in the brain. pNH3 values can be calculated from the total ammonia and pH. In some embodiments, a subject having hyperammonemia have elevated levels of pNH3 relative to a control subject (e.g., a subject not suspected of having hyperammonemia).

In some embodiments, serum levels of 3-nitrotyrosine may be elevated in a subject having, suspected of having, or at risk for minimal hepatic encephalopathy (MHE). In some embodiments, a subject having, suspected of having, or at risk for MHE has serum 3-nitrotyrosine levels of greater than about 10 nM, 15 nM, 20 nM, 30 nM, 40 nM, 50 nM, 60 nM, 70 nM, 80 nM, 90 nM, or 100 nM. In some embodiments, a subject having, suspected of having, or at risk for MHE has serum 3-nitrotyrosine levels of greater than about 10 nM or about 15 nM.

iii. Hepatic Encephalopathy (HE)

In some embodiments, a subject with hepatic encephalopathy (HE) may be treated according to the methods provided herein (e.g., using an oligosaccharide composition produced as described in Example 5, 6, or 14). Hepatic encephalopathy covers a complex set of neuropsychiatric symptoms and clinical signs affecting quality of life of both patients and their relatives. Hepatic encephalopathy is a common complication of advanced liver disease, including all forms of cirrhosis, and up to 80% of cirrhotic patients have some form of HE, ranging from minimal hepatic encephalopathy (MHE) to overt hepatic encephalopathy (OHE).

OHE is defined as neurologic abnormalities that are observable by a clinician without special testing. Symptoms can include shaking of the hands or arms, disorientation and slurred speech; patients can progress into coma. OHE can develop in patients with liver disease, cirrhosis and in patients with a transjugular intrahepatic portosystemic shunt (TIPS). This condition may follow a gastrointestinal bleed or infection. Development of OHE is associated with increased mortality. Admissions for OHE are frequent among patients with end stage liver disease (ESLD).

Patients with MHE have subtle symptoms that may only be detected using specialized psychometric tests and MHE is generally underdiagnosed. There is currently no common diagnostic paradigm in clinical practice to define MHE and there are no approved treatments for MHE. MHE can cause the loss of independent living skills (e.g., driving) and is predictive of subsequent development of OHE. Patients who have a single episode of OHE, often caused by a precipitant, and subsequently recover are also likely to have some level of MHE.

a. Presentation and Symptoms

Hepatic encephalopathy includes multiple adverse neurological symptoms that occur when the liver is unable to remove toxic substances such as ammonia from the blood. Liver dysfunction includes: liver cirrhosis (and portal hypertension), e.g., Types A (resulting from acute liver failure (ALF), B (resulting predominantly from PSS) or C (resulting from cirrhosis) (Child-Pugh Score for severity of liver cirrhosis); in the absence of cirrhosis—with either spontaneous or surgically created portosystemic shunts (portosystemic shunt surgery); portal-systemic bypass, acute liver failure (ALF), or acute-on-chronic liver failure (ACLF).

The 2014 AASLD and EASL clinical practice guidelines for managing HE recommend classifying HE according to the underlying liver disease, the severity of the manifestations, the time course, and precipitating factors. The severity of HE may be graded based upon clinical manifestations: Minimal (abnormal results on psychometric or neurophysiological testing with no clinical manifestations); Grade I (mild confusion, slurred speech, disordered sleep, behavioral changes); Grade II (lethargy, mild confusion); Grade III (marked confusion (stupor), incoherent speech, sleeping but arousable); and Grade IV (coma, unresponsive to pain). HE may be further subdivided according to the time course of the disease: episodic; recurrent (bouts of HE occur for 6 months or less); and persistent (patterns of behavioral alterations are always present and interspersed with relapses of overt HE).

'Minimal hepatic encephalopathy' (MHE), used interchangeably with the term 'covert hepatic encephalopathy' (CHE) is defined as the presence of test-dependent or clinical signs of brain dysfunction in patients with chronic liver disease (CLD) who are not disoriented or display asterixis. The term "minimal" conveys that there is no clinical sign, cognitive sign, or other sign of HE. The term "covert" includes minimal and grade 1 HE. Because the occurrence of MHE and CHE in patients with CLD may be as high as 50%, patients at risk should be tested.

A subject with HE may present with cognitive deficits including: confusion, forgetfulness, anxiety or excitation, sudden changes in personality or behavior, changes in sleep patterns, disorientation, sweet or musty smelling breath, slurred speech, and/or difficulty controlling motor functions. The condition reflects a diffuse disturbance of brain functions due to advanced liver disease or large portosystemic shunts (e.g., TIPS). Patients may present with neuromuscular impairments including bradykinesia, hyperreflexia, rigidity, myoclonus, and asterixis. Disturbances in the diurnal sleep pattern (insomnia and hypersomnia) are common initial manifestations of hepatic encephalopathy and typically precede other mental status changes or neuromuscular symptoms.

b. Diagnosis

Diagnosis of HE may be performed using tests of liver function, serum ammonia levels, EEG, and other blood and neurological tests. Psychometric tests for diagnosis include: Number Connection Test (Reitan Test) (timed connect-the-numbers test administered in two parts in which patients without hepatic encephalopathy should finish the test in a number of seconds less than or equal to their age in years); Psychometric Hepatic Encephalopathy Score (PHES) (five paper-pencil tests that evaluate cognitive and psychomotor processing speed and visuomotor coordination); Inhibitory Control Test (ICT) (computerized test of attention and response inhibition that has been used to characterize attention deficit disorder, schizophrenia, and traumatic brain injury); STROOP Task (test of psychomotor speed and cognitive flexibility that evaluates the functioning of the anterior attention system and is sensitive for the detection of cognitive impairment in minimal hepatic encephalopathy); Repeatable Battery for the Assessment of Neuropsychological Status (RBANS) (measures a wide range of neurocognitive functions relevant to minimal hepatic encephalopathy); and the Continuous Reaction Time (CRT) test (relies on repeated registration of the motor reaction time (pressing a button) to auditory stimuli (through headphones)).

Neurophysiological tests for diagnosis include the Critical Flicker Frequency (CFF) Test (psychophysiological tool defined as the frequency at which a fused light (presented from 60 Hz downward) appears to be flickering to the observer); Electroencephalography examination (which may detect changes in cortical cerebral activity across the spectrum of HE without patient cooperation or risk of a learning effect); and Evoked Potentials (externally recorded electrical signals that reflect synchronous volleys of discharges through neuronal networks in response to various afferent stimuli). In some embodiments, hepatic encephalopathy is diagnosed using any combination of two or more psychometric or neurophysiological tests.

c. Treatment of HE

Medical treatment of HE currently includes treatment of the underlying precipitant, if present, such as gastrointestinal bleeding or infection. Standard-of-care treatments for HE include lactulose, lactitol, and antibiotics (e.g., rifaximin or neomycin).

Lactulose is a non-absorbed disaccharide that has been used for several decades to reduce hyperammonemia in OHE patients. Lactulose's mechanism of action is thought to work primarily through purging of the stool and acidification of the colonic environment, leading to the conversion of ammonia to ammonium, which less readily crosses the colonic barrier and enters the bloodstream. Lactulose has also been shown to stimulate bacterial growth, thus promoting assimilation of ammonia into bacterial proteins. Lactulose reduces episodes of OHE by up to 50% compared to a placebo.

Rifaximin, a poorly-absorbed antibiotic derived from rifamycin, is currently approved as a second line treatment for OHE and is used in conjunction with lactulose when lactulose alone does not control OHE. When administered in combination with lactulose, rifaximin reduces episodes of OHE by approximately 50%. Neither lactulose nor rifaximin sufficiently reduces the risk of OHE recurrence, each episode of which significantly increases mortality risk.

Treatments may also include dietary modifications and probiotics. Treatment efficacy may be assessed by resolution of the symptoms or diagnostic criteria listed above (e.g., reduction in serum ammonia levels), decreased incidence of future episodes of HE, or, in a subject at risk of HE, by decreased occurrence of an initial episode of HE.

IV. Kits

Kits also are contemplated. For example, a kit can comprise unit dosage forms of the oligosaccharide composition, and a package insert containing instructions for use of the composition in treatment, e.g., of a disease associated with hyperammonemia, e.g., urea cycle disorder or hepatic encephalopathy. In some embodiments, the composition is provided in a dry powder format. In some embodiments, the composition is provided in solution. The kits include an oligosaccharide composition in suitable packaging for use by a subject in need thereof. Any of the compositions described herein can be packaged in the form of a kit. A kit can contain an amount of an oligosaccharide composition sufficient for an entire course of treatment, or for a portion of a course of treatment. Doses of an oligosaccharide composition can be individually packaged, or the oligosaccharide composition can be provided in bulk, or combinations thereof. Thus, in one embodiment, a kit provides, in suitable packaging, individual doses of an oligosaccharide composition that correspond to dosing points in a treatment regimen, wherein the doses are packaged in one or more packets.

Kits can further include written materials, such as instructions, expected results, testimonials, explanations, warnings, clinical data, information for health professionals, and the like. In one embodiment, the kits contain a label or other information indicating that the kit is only for use under the direction of a health professional. The container can further include scoops, syringes, bottles, cups, applicators or other measuring or serving devices.

EXAMPLES

Example 1. Reduction of Ammonia in Fecal Slurries from Humans in the Presence of Oligosaccharide Compositions Approximately three hundred and fifty oligosaccharide compositions were tested for their ability to modulate the levels of ammonia in a fecal slurry from a healthy human subject in vitro (also referred to as an ex vivo assay). Fecal samples and slurries were handled in an anaerobic chamber (AS-580, Anaerobe Systems) in the presence of a palladium catalyst. Oligosaccharide compositions were prepared at 5% w/v in water, filter-sterilized and added to 96-well deep well microplates assay plates for a final concentration of 0.5% or 0.05% w/v in the assay, with water supplied as a negative control.

A human fecal sample donation was stored at −80° C. To prepare working stocks of fecal slurry, the fecal sample was transferred into the anaerobic chamber and allowed to thaw. The fecal sample was then prepared in 20% w/v in phosphate buffered saline (PBS) pH 7.4 (P0261, Teknova Inc., Hollister, CA), 15% glycerol. The 20% w/v fecal slurry+ 15% glycerol was centrifuged at 2,000×g, supernatant was removed, and the pellet was suspended in 1% PBS prior to dilution in a media consisting of 900 mg/L sodium chloride, 26 mg/L calcium chloride dihydrate, 20 mg/L magnesium chloride hexahydrate, 10 mg/L manganese chloride tetrahydrate, 40 mg/L ammonium sulfate, 4 mg/L iron sulfate heptahydrate, 1 mg/L cobalt chloride hexahydrate, 300 mg/L potassium phosphate dibasic, 1.5 g/L sodium phosphate dibasic, 5 g/L sodium bicarbonate, 0.125 mg/L biotin, 1 mg/L pyridoxine, 1 m/L pantothenate, 75 mg/L histidine, 75 mg/L glycine, 75 mg/L tryptophan, 150 mg/L arginine, 150 mg/L methionine, 150 mg/L threonine, 225 mg/L valine, 225 mg/L isoleucine, 300 mg/L leucine, 400 mg/L cysteine, and 450 mg/L proline (Theriot C M et al. Nat Commun. 2014; 5:3114) that was further supplemented with 750 µM urea to provide a final dilution of 1% w/v fecal slurry.

The prepared 1% w/v fecal slurry was exposed to the 96-well plates of oligosaccharide compositions at a final concentration of 0.5% w/v, 350 µL final volume per well, at 37° C. for 45 hours, anaerobically.

Figure 1B:
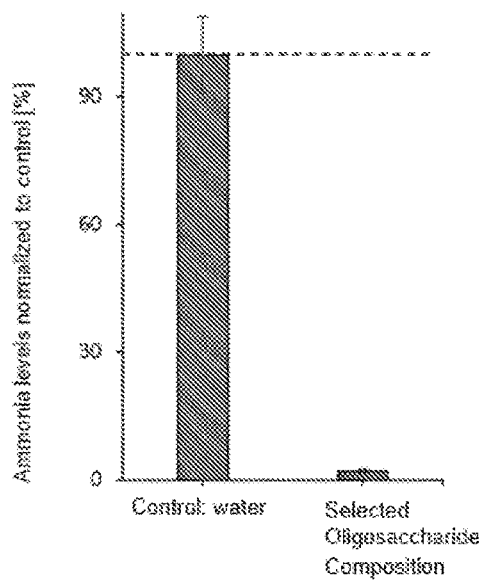

Following ex vivo incubation, cells were pelleted using centrifugation at 3,716×g for 10 minutes and the supernatant was stored at −80° C. or on dry ice prior to analysis. Samples were filtered using a 10 kDa filter (AcroPrep Omega 10K, Pall Corporation, Port Washington New York) at 1,500×g for 15 minutes and diluted in water to $1/10^{th}$ the original volume. Samples were then analyzed using Ammonia Colorimetric Assay Kit II (K470, Biovision Incorporated, Milpitas CA). Results of the Ammonia Colorimetric Assay for the oligosaccharide compositions are shown in FIGS. 1A and 1B. Ammonia levels were normalized to a negative control (water). As depicted in FIGS. 1A-1B, a selected oligosaccharide composition demonstrated greater than 95% efficacy in reduction of ammonia levels relative to the negative control.

Example 2: Studies of Selected Oligosaccharide Composition in Healthy Human Subjects The safety and tolerability of the selected oligosaccharide composition, as described in Example 1, was evaluated in healthy human adults in a randomized, double-blind, placebo-controlled study (n=47) designed to measure prebiotic activity in the presence of a high protein diet. Doses were titrated up in four stages to maximize tolerability, starting at 9 g twice daily with food for four days to 36 g twice daily for six days; subjects were allowed to decrease dosing (dose de-escalation) based on tolerability.

The gut (e.g., by fermentation of foods by gut bacteria and glutaminase activity by enterocytes) contributes a substantial amount of ammonia to the human metabolism. According to some estimates, up to 70% of excess ammonia in a hyperammonemic subject accumulates in the gastrointestinal tract (U.S. Pat. No. 9,487,764). In the gut, ammonia is generated by microbial urease and amino acid deamination, and enterocyte glutaminase (Romero-Gomez et al. Metab Brain Dis (2009) 24:147-157). Reducing the amount of ammonia originating in the gut microbiota may have a therapeutic effect in diseases associated with hyperammonemia. The hyperammonemia-associated disease hepatic encephalopathy (HE, including overt HE (OHE)) is treated with lactulose (4-O-β-D-Galactosyl-D-fructose) and/or rifaximin (an antibiotic derived from rifamycin SV). Both agents target gut bacterial ammonia contribution to the systemic ammonia load. Subjects with other diseases associated with hyperammonemia, e.g., urea cycle disorders (UCD) and subjects who are at risk for developing hyperammonemia (e.g., subjects exhibiting minimal HE, MHE) would likely also benefit from a reduction of gut bacterial ammonia contribution to the systemic ammonia load. However, lactulose and rifaximin are not used in these subjects.

A high protein challenge study in humans was conducted to test whether oral administration of glycans described herein can reduce the amount of gut-derived ammonia.

Healthy subjects do not develop hyperammonemia upon protein challenge due to intact liver metabolism (e.g., urea cycle capacity and no bypass of the liver) and kidney function (e.g., functioning urea and ammonia excretion). Serum ammonia levels are highly variable, e.g., in part due to measuring bias (e.g., venous blood captures ammonia after passage through muscle that store ammonia), volatility of the analyte, and influence of the subject's diet. Healthy subjects were challenged with a high protein diet (2 g/kg protein/day for 4 weeks) delivering substrate for colonic ammonia production and administered a stable isotope tracer ($^{15}$N lactoureide) to quantify gut bacteria-derived ammonia. Subjects consumed either the selected oligosaccharide composition, a control, a commercially available fiber preparation (positive control), or maltodextrin (MDX), as a placebo or negative control. MDX is fully digestible and does not reach the colon as substrate for bacterial fermentation. Subjects (N=12/group) were placed on a high-protein diet for 7 days (run-in) before administration of $^{15}$N-tracer. The diet was continued for additional 16 days with up-titration of glycan preparations before a second administration of $^{15}$N-tracer. Subjects were up-titrated from 9 g/d BID to 36 g/d BID (72 g/day total). Blood, urine and stool samples were collected.

Findings from this study showed that the selected oligosaccharide composition was safe and generally well tolerated (as assessed using the gastrointestinal tolerability questionnaire (GITQ) where the severity and frequency of gastrointestinal symptoms of flatulence, nausea, vomiting, abdominal cramping, bloating, borborygmus, burping and heartburn as well as the frequency and urgency of bowel movements are recorded in a daily questionnaire).

Figure 2:
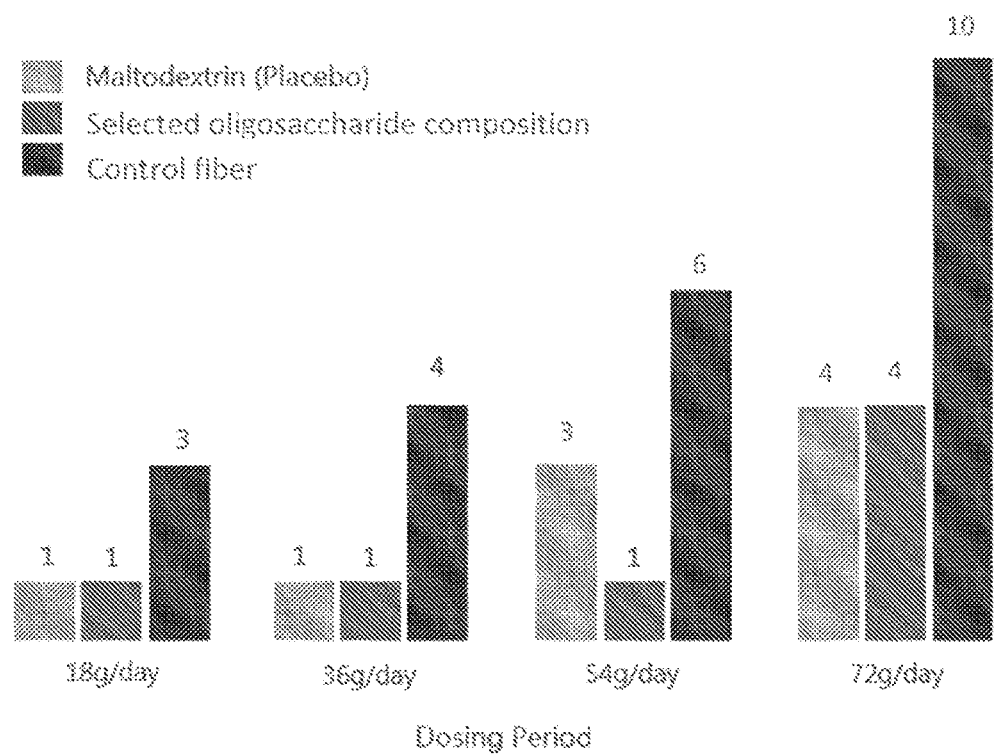
FIG. 2 provides a graph of patient tolerability in response to consuming oligosaccharide compositions.

Tolerability of the selected oligosaccharide composition was also assessed by diarrhea score (FIG. 2). Stool composition from each subject was assessed on a daily 7-point Bristol Stool Score questionnaire. As shown in FIG. 2, the selected oligosaccharide composition had the same or fewer subjects reporting diarrhea as the placebo, whereas the commercially available positive control fiber caused an increase in subjects reporting diarrhea, with 10 out of 12 subjects reporting diarrhea at the highest dose.

The maltodextrin control, on the background of a high protein diet, increased $^{15}$N-nitrogen excretion while both the selected oligosaccharide composition and the positive control fiber reduced urinary $^{15}$N-nitrogen excretion by 30-40% versus control (p=0.002). Reduction in urinary $^{15}$N-urea excretion by the selected oligosaccharide composition and the positive control fiber was significant versus control (p=0.0343 and p=0.0002, respectively) with similar effect size (30-40% reduction). $^{15}$N urinary ammonia excretion was variable and not statistically significant but showed a similar trend toward reduction.

2×10 g and 2×15 g/day lactulose over 4 weeks reduces urinary excretion of 15N nitrogen in healthy subjects on a normal diet by 12-22% compared to baseline (De Preter et al. Aliment Pharmacol Ther (2006) 23, 963-974). In a head to head trial in patients with HE, lactulose and rifaximin reduced blood ammonia by 33 and 32%, respectively (Paik et al. Yonsei Medical Journal Vol. 46, No. 3, pp. 399-407, 2005). In a study, lactulose reduced arterial ammonia by 23% (60 patients with HE) and showed complete reversal of HE in 53% of patients within 10 days (Sharma et al. Journal of Gastroenterology and Hepatology 32 (2017) 1234-1239). The reductions for gut-derived ammonia observed for the selected oligosaccharide composition tested herein, 30-40% reduction in urinary $^{15}$N-nitrogen excretion, suggest that the reduction is clinically relevant, and that the selected oligosaccharide composition described herein may be used to reduce blood ammonia.

The selected oligosaccharide composition did not cause considerable diarrhea, suggesting that the nitrogen-lowering effect is not caused by diarrhea-driven flushing out of nitrogen but likely an effect of changes in microbial taxa and/or associated nitrogen metabolism. The effect of the positive control fiber may largely be due to the diarrhea (and physical flushing out the nitrogen) caused the positive control fiber. Diarrhea is an undesirable side effect.

The selected oligosaccharide composition may thus be used for the treatment of subjects with diseases associated with hyperammonemia, such as, e.g., HE (e.g., OHE), and UCD, as well as subjects who are at risk for developing hyperammonemia, e.g., MHE.

Example 3: Decrease in Ammonia Levels in Ex Vivo Assay with Fecal Samples Obtained from Urea Cycle Disorder (UCD) Patients An ex vivo assay was performed to assess the ability of a human fecal community collected from urea cycle disorder (UCD) patients to utilize the selected oligosaccharide composition, as described in Example 1, and reduce production or increase consumption of ammonia. Fecal samples were collected from 12 patients (Pt 1 to Pt 12, FIG. 3A) diagnosed with urea cycle disorder (UCD).

Human fecal sample donations were stored at −80° C. To prepare working stocks the fecal samples were transferred into the anaerobic chamber and allowed to thaw. Each fecal sample was prepared to 20% w/v in phosphate buffered saline (PBS) pH 7.4 (P0261, Teknova Inc., Hollister, CA), 15% glycerol and stored at −80° C. The 20% w/v fecal slurry+15% glycerol was centrifuged at 2,000×g, supernatant was removed, and the pellet was suspended in 900 mg/L sodium chloride, 26 mg/L calcium chloride dihydrate, 20 mg/L magnesium chloride hexahydrate, 10 mg/L manganese chloride tetrahydrate, 40 mg/L ammonium sulfate, 4 mg/L iron sulfate heptahydrate, 1 mg/L cobalt chloride hexahydrate, 300 mg/L potassium phosphate dibasic, 1.5 g/L sodium phosphate dibasic, 5 g/L sodium bicarbonate, 0.125 mg/L biotin, 1 mg/L pyridoxine, 1 m/L pantothenate, 75 mg/L histidine, 75 mg/L glycine, 75 mg/L tryptophan, 150 mg/L arginine, 150 mg/L methionine, 150 mg/L threonine, 225 mg/L valine, 225 mg/L isoleucine, 300 mg/L leucine, 400 mg/L cysteine, and 450 mg/L proline (Theriot C M et al. Nat Commun. 2014; 5:3114) supplemented with 750 mL urea to prepare 1% w/v fecal slurry.

Prepared 1% w/v fecal slurries were exposed to selected oligosaccharide compositions and tested for effective reduction in ammonia levels. Selected oligosaccharide compositions were added at a final concentration of 0.5% w/v in 96-well deep well microplates, with water included in "No Added Glycan" controls, with 500 μL final volume per well. The glycan and slurry mixes were incubated at 37° C. for 45 hours, anaerobically.

Figure 3A:
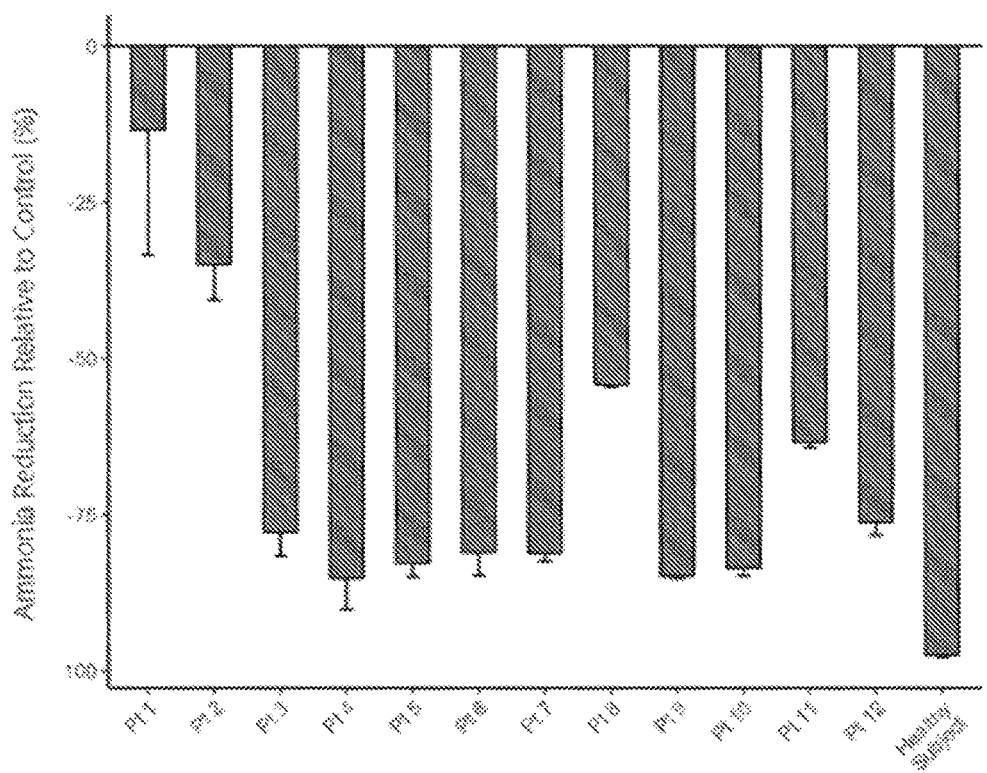
FIGS. 3A-3B provide graphs showing ammonia reduction (normalized to water controls) in an ex vivo ammonia reduction assay where fecal samples from patients were incubated with the selected oligosaccharide composition.

Following ex vivo incubation as described herein, cells were pelleted by centrifugation at 3,716×g for 10 minutes and the supernatant was stored at −80° C. or on dry ice until it was analyzed. Samples were filtered in 10 kDa filter (AcroPrep Omega 10K, Pall Corporation, Port Washington New York) at 1,500×g for 15 minutes and diluted in water to 1/10 the original concentration. Samples were analyzed using Ammonia Colorimetric Assay Kit II (K470, Biovision Incorporated, Milpitas CA). Results of the Ammonia Colorimetric Assay for the oligosaccharide compositions are shown in FIG. 3A. Ammonia levels were normalized to a negative control (water).

Across fecal samples tested at 45 hours, the selected oligosaccharide composition demonstrated reduction in ammonia levels in all urea cycle disorder (UCD) patient samples (FIG. 3A). In particular, the selected oligosaccharide composition produced a greater than about 50% reduction in ammonia levels compared to control across 10 out of 12 patient communities (FIG. 3A). This would suggest that administration of the selected oligosaccharide composition could be used to reduce ammonia levels in urea cycle disorder patients.

Example 4: Decrease in Ammonia Levels in Ex Vivo Assay with Fecal Samples Obtained from Hepatically Impaired Patients An ex vivo assay was performed to assess the ability of a human fecal community collected from hepatically impaired patients to utilize the selected oligosaccharide composition, as described in Example 1, and reduce production or increase consumption of ammonia compared to existing treatments. In the gut, ammonia is generated by microbial urease and amino acid deamination, and enterocyte glutaminase (Romero-Gomez et al. Metab Brain Dis (2009) 24:147-157). Reducing the amount of ammonia originating in the gut microbiota may have a therapeutic effect in diseases associated with hyperammonemia. The hyperammonemia-associated disease hepatic encephalopathy (HE) is treated with lactulose (4-O-β-D-Galactosyl-D-fructose) which targets gut bacterial ammonia contribution to the systemic ammonia load. Fecal samples were collected from 19 patients diagnosed with hepatic encephalopathy (HE) caused by alcohol, autoimmune hepatitis, chronic hepatitis B, fatty liver disease/NASH, or iron overload and steatosis.

Human fecal sample donations were stored at −80° C. To prepare working stocks the fecal samples were transferred into the anaerobic chamber and allowed to thaw. Each fecal sample was prepared to 20% w/v in phosphate buffered saline (PBS) pH 7.4 (P0261, Teknova Inc., Hollister, CA), 15% glycerol and stored at −80° C. The 20% w/v fecal slurry+15% glycerol was centrifuged at 2,000×g, supernatant was removed, and the pellet was suspended in 900 mg/L sodium chloride, 26 mg/L calcium chloride dihydrate, 20 mg/L magnesium chloride hexahydrate, 10 mg/L manganese chloride tetrahydrate, 40 mg/L ammonium sulfate, 4 mg/L iron sulfate heptahydrate, 1 mg/L cobalt chloride hexahydrate, 300 mg/L potassium phosphate dibasic, 1.5 g/L sodium phosphate dibasic, 5 g/L sodium bicarbonate, 0.125 mg/L biotin, 1 mg/L pyridoxine, 1 m/L pantothenate, 75 mg/L histidine, 75 mg/L glycine, 75 mg/L tryptophan, 150 mg/L arginine, 150 mg/L methionine, 150 mg/L threonine, 225 mg/L valine, 225 mg/L isoleucine, 300 mg/L leucine, 400 mg/L cysteine, and 450 mg/L proline (Theriot C M et al. Nat Commun. 2014; 5:3114) supplemented with 750 mL urea to prepare 1% w/v fecal slurry.

Prepared 1% w/v fecal slurries were exposed to the selected oligosaccharide composition or lactulose and tested for effective reduction in ammonia levels. Oligosaccharide compositions and lactulose were added at a final concentration of 0.5% w/v in 96-well deep well microplates, with water included in "No Added Glycan" controls, with 500 μL final volume per well. The test compound and slurry mixes were incubated at 37° C. for 45 hours, anaerobically.

Figure 3B:
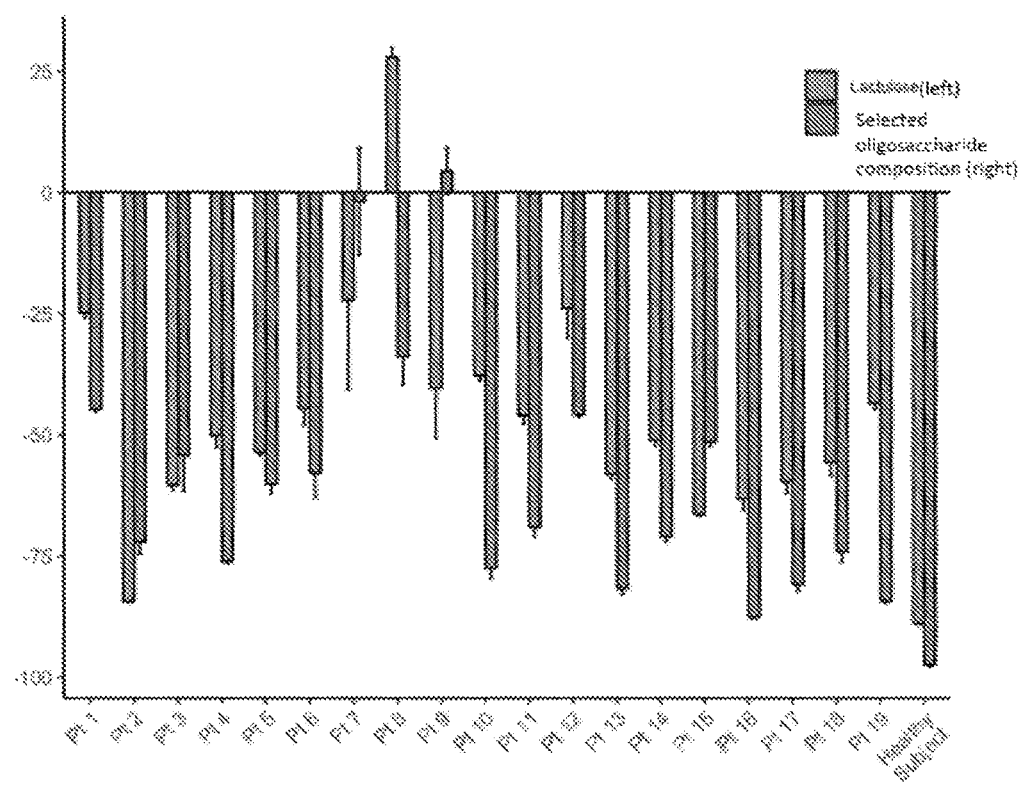

Following ex vivo incubation as described herein, cells were pelleted by centrifugation at 3,716×g for 10 minutes and the supernatant was stored at −80° C. or on dry ice until it was analyzed. Samples were filtered in 10 kDa filter (AcroPrep Omega 10K, Pall Corporation, Port Washington New York) at 1,500×g for 15 minutes and diluted in water to 1/10 the original concentration. Samples were analyzed using Ammonia Colorimetric Assay Kit II (K470, Biovision Incorporated, Milpitas CA). Results of the Ammonia Colorimetric Assay for the oligosaccharide compositions and lactulose are shown in FIG. 3B. Ammonia levels were normalized to a negative control (water).

Across fecal samples tested at 45 hours, the oligosaccharide compositions demonstrated reduction in ammonia levels in 18 of 19 hepatically impaired patient samples (FIG. 3B). The oligosaccharide composition outperformed lactulose in reducing ammonia levels in 14 out of 19 patient communities (FIG. 3B). This would suggest that administration of the oligosaccharide composition could be used to reduce ammonia levels in hepatically impaired patients.

Example 5: Production of Oligosaccharide Composition at 100 g Scale from Dextrose Monohydrate or 70DS Corn Dextrose Syrup A procedure was developed for the synthesis of the selected oligosaccharide composition described in Examples 1-4 at a 100-gram scale. The procedure allows for the synthesis of the selected oligosaccharide composition starting from a glucose source, such as either dextrose monohydrate or corn dextrose syrup, as described below. The procedure utilized a multi-neck reaction vessel with the heating mantle configured with an overhead stirrer. A probe thermocouple was disposed in the vessel through a septum, such that the probe tip sat above the stir blade and not in contact with the walls of the reaction vessel.

The procedure was run using D(+) glucose, as either dextrose monohydrate (100 grams, dry solids basis) or 95DE, 70DS corn dextrose syrup (100 grams, dry solids basis). When the oligosaccharide was produced using dextrose monohydrate, the condenser was configured initially in a re-flux reaction configuration. When the oligosaccharide was produced using 70DS corn dextrose syrup, the apparatus was configured initially for distillation.

According to the procedure, the multi-neck reaction vessel was first charged with 109.9 g dextrose monohydrate powder (or 142.9 g of 70DS 95 DE corn syrup) to provide 100 g dry glucose to the reaction.

The temperature controller was set to 130° C. and the contents of the vessel were stirred to promote uniform heat transfer and to melt the sugar solids. The temperature of the syrup was brought to approximately 130° C. under ambient (atmospheric) pressure.

When the reaction vessel was charged with dextrose monohydrate, the condenser reflux system was switched to a distillation configuration once the syrup was at a temperature of 130° C. approximately. When the reaction vessel was charged with 70DS corn dextrose syrup, the condenser reflux system was kept in a distillation configuration when the syrup reached 130° C.

Next, the vessel was charged with 7 grams (dry solids basis) of oligomerization catalyst (Dowex® Marathon® C) to generate the reaction mixture. In some cases, the catalyst was handled in wet form, e.g., at a nominal moisture content of 45-50 wt % $H_2O$. The exact catalyst moisture content was generally determined on a per-experiment basis using, for example, a moisture analyzing balance (e.g., Mettler-Toledo MJ-33).

Upon addition of the catalyst, the system was maintained at approximately 130° C. under continuous mixing for about 4 hours, determined by following the reaction by HPLC. Next, the heat was turned off while maintaining constant stirring.

The reaction was then quenched by slowly adding approximately 60 ml of hot (~80° C.) deionized (DI) water to dilute and cool the product mixture until it was at a final concentration of about 70 wt % dissolved solids. Generally, the rate at which the water was added to the product mixture was regulated to control the mixture viscosity as the oligosaccharide composition was cooled and diluted.

Following dilution, the oligosaccharide composition was cooled to approximately 60° C. The catalyst was then removed by vacuum filtration through a 100-micron mesh screen or fritted-glass filter to obtain the final oligosaccharide composition.

Example 6: Production of Oligosaccharide Composition at 10 kg Scale from Dextrose Monohydrate The present example demonstrates the synthesis of the selected oligosaccharide composition described in Examples 1-4 at the 10 kg scale in a 22 L horizontal-mixed reactor.

About 10 kg of food grade dextrose monohydrate was charged into a 22 L horizontal plough mixer (Littleford-Day, Lexington, KY) equipped with a hot-oil jacket. The dextrose was melted by gradually heating to a temperature of about 120° C. with continuous mixing at 30 RPM. 1.27 kg (0.70 kg on a dry solid basis) solid acid catalyst (e.g., styrene-divinylbenzene comprising sulfonic acid moieties, e.g., Dowex® Marathon® C resin) was then added to the reaction mixture to form a mixed suspension. The reaction temperature was gradually increased to about 130° C. at atmospheric pressure over a three-hour period with continuous mixing maintained at 30 RPM. The reaction was maintained at temperature of 130° C. for seven hours. Hot de-ionized water was then gradually added to the reaction mixture at a rate of 6 mL/min until the temperature of the reactor contents decreased to 120° C., then at 150 mL/min until the temperature of the reactor contents decreased to 110° C., and then at 480 mL/min until a total of 6 kg of water was added and the temperature of the reactor contents decreased below 100° C. The reactor contents were further cooled to below 85° C., and then the reactor was emptied through a 100 mesh screen to remove the solid acid catalyst from the oligosaccharide composition. Approximately 12 kg of product material was recovered.

The oligosaccharide composition was further diluted to a concentration of about 35 wt % in de-ionized water and then purified by flowing through a cationic exchange resin (Dowex® Monosphere 88H) column, an anionic exchange resin (Dowex® Monosphere 77WBA) column, a decolorizing polymer resin (Dowex® OptiPore SD-2), and an anionic exchange resin (Dowex® Monosphere 77WBA) column. The resulting purified material was then concentrated to a final concentration of about 75 wt % solids by vacuum rotary evaporation to yield the purified oligosaccharide composition.

Example 7: Determination of Glycosidic Bond Distribution Using Permethylation Analysis A determination of the glycosidic bond distribution of samples of the selected oligosaccharide composition, as described in Examples 1-4, was performed using permethylation analysis, according to the protocol described below. Samples of the selected oligosaccharide composition made using the production methods of Examples 5, 6, and 14 were analyzed using this procedure.

The reagents used in this procedure included methanol, acetic acid, sodium borodeuteride, sodium carbonate, dichloromethane, isopropanol, trifluoroacetic acid (TFA), and acetic anhydride. The equipment used in this procedure included a heating block, drying apparatus, gas chromatograph equipped for capillary columns and with a RID/MSD detector, and a 30 meter RTX®-2330 (RESTEK). All derivation procedures were done in a fume hood.

Preparation of Alditol Acetates

A. Standard Preparation 1 mg/mL solutions of the following standard analytes were prepared: arabinose, rhamnose, fucose, xylose, mannose, galactose, glucose, and inositol. Each standard was prepared by mixing 50 μL of arabinose, xylose, fucose, glucose, mannose, or galactose with 20 μL of inositol in a vial. The standards were subsequently lyophilized.

B. Sample Preparation

Each oligosaccharide sample was prepared by mixing 100-500 μg of the selected oligosaccharide composition (as weighed on an analytical balance) with 20 μg (20 μL) of inositol in a vial.

C. Hydrolysis

200 μL of 2 M tifluoroacetic acid (TFA) was added to each oligosaccharide sample. The vial containing the sample was capped tightly and incubated on a heating block for 2 hours at 121° C. After 2 hours, the sample was removed from the heating block and allowed to cool to room temperature. The sample was then dried down with $N_2$/air. 200 μL of isopropanol (IPA) was added and dried down again with $N_2$/air. This hydrolysis step (addition of TFA for two hours at 121° C.; washing with isopropanol) was repeated twice.

The standards were similarly subjected to hydrolysis using TFA, as described for the samples.

D. Reduction and Acetylation

A 10 mg/mL solution of sodium borodeuteride was prepared in 1 M ammonium hydroxide. 200 μL of this solution was added to each oligosaccharide sample. The sample was then incubated at room temperature for at least one hour or overnight. After incubation with sodium borodeuteride solution, 5 drops of glacial acetic acid were added to the sample, followed by 5 drops of methanol. The sample was then dried down. 500 μL of 9:1 MeOH:HOAc was added to the sample and subsequently dried down (twice repeated). 500 μL MeOH was then added to the sample and subsequently dried down (once repeated). This produced a crusty white residue on the side of the sample vial.

250 μL acetic anhydride was then added to each sample vial and the sample was vortexed to dissolve. 230 μL concentrated TFA was added to each sample and the sample was incubated at 50° C. for 20 minutes. The sample was removed from the heat and allowed to cool to room temperature. Approximately 1 mL isopropanol was added and the sample was dried down. Then, approximately 200 μL isopropanol was added and the sample was dried down again. Approximately 1 mL of 0.2M sodium carbonate was then added to each sample and it was mixed gently. Approximately 2 mL dichloromethane was finally added to each sample, after which it was vortexed and centrifuged briefly. The aqueous top layer was discarded. 1 mL water was added and the sample was vortexed and centrifuged briefly. This step was repeated before the organic layer (bottom) was removed and transferred to another vial. Each sample was concentrated using $N_2$/air to a final volume of about 100 μL. 1 μL of final sample was then injected on GC-MS.

The GC temperature program SP2330 was utilized for GC-MS analysis. The initial temperature was 80° C. and the initial time was 2.0 minutes. The first ramp was at a rate of 30° C./min with a final temperature of 170° C. and a final time of 0.0 minutes. The second ramp was at a rate of 4° C./min with a final temperature of 240° C. and a final time of 20.0 minutes.

Glycosyl-Linkage Analysis of Poly- and Oligosaccharides by Hakomori Methylation

A. Preparation of NaOH Base

In a glass screw top tube, 100 µL of a 50/50 NaOH solution and 200 µL of dry MeCOH were combined. Plastic pipets were used for the NaOH and glass pipets were used for the MeOH. The solution was vortexed briefly, approximately 4 mL dry DMSO was added, and the solution was vortexed again. The tube was centrifuged to concentrate the solution and the DMSO and salts were pipetted off from the pellet. The previous two steps were repeated about four times in order to remove all the water from the pellet. All white reside was removed from the sides of the tube. Once all the residue was removed and the pellet was clear, about 1 mL dry DMSO was added and the solution was vortexed. The base was then ready to use. The base was prepared fresh each time it was needed.

B. Permethylation

Each sample was prepared by mixing 600-1000 µg of the selected oligosaccharide composition (as weighed on an analytical balance) with 200 µL DMSO. The sample was stirred overnight until the oligosaccharide composition dissolved.

An equal amount of NaOH base (400 µL) was added to the sample, after which the sample was placed back on the stirrer and mixed well for 10 minutes. 100 µL of iodomethane ($CH_3I$) was added to the sample. The sample was mixed on the stirrer for 20 minutes, and then the previous steps (addition of NaOH base and iodomethane) were repeated.

Approximately 2 mL of ultrapure water was added to the sample and the sample was mixed well, such that it turned cloudy. The tip of a pipette was placed into the sample solution at the bottom of the tube and $CH_3I$ was bubbled off with a very low flow of air. The sample became clear as the $CH_3I$ was bubbled off. The pipette was moved around the solution to make certain that all the $CH_3I$ was gone. Approximately 2 mL methylene chloride was then added and the solution was mixed well by vortex for 30 seconds. The sample was then centrifuged and the top aqueous layer was removed. Approximately 2 mL of water was added and the sample was mixed, then briefly centrifuged, then the top aqueous layer was removed. The additions of methylene chloride and water were repeated. The organic bottom layer was removed and transferred into another tube and dried down using $N_2$. The analysis was continued with Alditol Acetates.

C. Hydrolysis

200 µL of 2 M tifluoroacetic acid (TFA) was added to each oligosaccharide sample. The vial containing the sample was capped tightly and incubated on a heating block for 2 hours at 121° C. After 2 hours, the sample was removed from the heating block and allowed to cool to room temperature. The sample was then dried down with $N_2$/air. 200 µL of isopropanol (IPA) was added and dried down again with $N_2$/air. This hydrolysis step (addition of TFA for two hours at 121° C.; washing with isopropanol) was repeated twice.

D. Reduction and Acetylation

A 10 mg/mL solution of sodium borodeuteride was prepared in 1 M ammonium hydroxide. 200 µL of this solution was added to each oligosaccharide sample. The sample was then incubated at room temperature for at least one hour or overnight. After incubation with sodium borodeuteride solution, 5 drops of glacial acetic acid were added to the sample, followed by 5 drops of methanol. The sample was then dried down. 500 µL of 9:1 MeOH:HOAc was added to the sample and subsequently dried down (twice repeated). 500 µL MeOH was then added to the sample and subsequently dried down (once repeated). This produced a crusty white residue on the side of the sample vial.

250 µL of acetic anhydride was then added to each sample vial and the sample was vortexed to dissolve. 230 µL concentrated TFA was added to the sample and the sample was incubated at 50° C. for 20 minutes. The sample was removed from the heat and allowed to cool to room temperature. Approximately 1 mL isopropanol was added and the sample was dried down. Then, approximately 200 µL of isopropanol was added and the sample was dried down again. Approximately 1 mL of 0.2M sodium carbonate was then added to the sample and it was mixed gently. Approximately 2 mL of dichloromethane was finally added to the sample, after which it was vortexed and centrifuged briefly. The aqueous top layer was discarded. 1 mL of water was added and the sample was vortexed and centrifuged briefly. This step was repeated before the organic layer (bottom) was removed and transferred to another vial. Each sample was concentrated using $N_2$/air to a final volume of about 100 µL. 1 µL of final sample was then injected on GC-MS.

The GC temperature program SP2330 was utilized for GC-MS analysis. The initial temperature was 80° C. and the initial time was 2.0 minutes. The first ramp was at a rate of 30° C./min with a final temperature of 170° C. and a final time of 0.0 minutes. The second ramp was at a rate of 4° C./min with a final temperature of 240° C. and a final time of 20.0 minutes.

Example 8: Process for Establishing Glycosidic Bond Distribution Using Permethylation Analysis Permethylation data was collected using the method presented in Example 7 for ten batches of de-monomerized oligosaccharide composition (wherein the oligosaccharide compositions were produced by the process described in Example 5). These batches were demonomerized according to the method described in Example 9. The results of this analysis are presented in Table 4.

For each permethylation data set, the sum value of the AUC of all the peaks listed in Table 4 was determined.

For each Peak listed in Table 4, the AUC of the peak was divided by the sum value of the AUC of all the peaks, converted to a percentage format to three significant digits, and recorded.

The total of the recorded percentage values in a given data set was confirmed to be 100%.

A mean value for each Peak is listed in Table 4 as determined across all data sets using the standard formula A standard deviation for each Peak is listed in Table 4 as determined across all data sets using the standard formula.

The acceptable range for each Peak of the selected oligosaccharide composition is listed in Table 4 as determined to be less than (MEAN_P1+5*STDP1) and greater than (MEAN-P1 −5*STD_P1)

TABLE 4

Mean mol % of monomer radicals for the selected oligosaccharide composition

| Peak Number | Monomer radical | Mean mol % +5 STD | Mean mol % +3 STD | Mean mol % | Mean mol % −3 STD | Mean mol % −5 STD |
|---|---|---|---|---|---|---|
| 1 | t-glucopyranose | 46.98% | 42.95% | 36.92% | 30.89% | 26.87% |
| 2 | 3-glucopyranose | 9.25% | 8.79% | 8.10% | 7.40% | 6.94% |
| 3 | 2-glucopyranose | 9.54% | 8.86% | 7.85% | 6.83% | 6.15% |
| 4 | 6-glucopyranose | 24.61% | 23.48% | 21.78% | 20.08% | 18.94% |
| 5 | 4-glucopyranose | 8.64% | 8.24% | 7.64% | 7.03% | 6.63% |
| 6 | 3,4-glucopyranose | 1.42% | 1.22% | 0.91% | 0.61% | 0.41% |
| 7 | 2,3-glucopyranose | 2.59% | 2.33% | 1.93% | 1.54% | 1.28% |
| 8 | 2,4-glucopyranose | 1.42% | 1.27% | 1.03% | 0.79% | 0.64% |
| 9 | 3,6-glucopyranose | 6.01% | 5.28% | 4.18% | 3.08% | 2.35% |
| 10 | 2,6-glucopyranose/ 4,6-glucopyranose | 9.66% | 8.74% | 7.37% | 6.00% | 5.09% |
| 11 | 2,3,4-glucopyranose | 0.85% | 0.69% | 0.47% | 0.24% | 0.08% |
| 12 | 3,4,6-glucopyranose | 1.00% | 0.83% | 0.56% | 0.29% | 0.11% |
| 13 | 2,4,6-glucopyranose | 0.72% | 0.64% | 0.52% | 0.41% | 0.33% |
| 14 | 2,3,6-glucopyranose | 0.86% | 0.70% | 0.46% | 0.22% | 0.06% |
| 15 | 2,3,4,6-glucopyranose | 0.61% | 0.48% | 0.29% | 0.10% | 0.00% |

Permethylation data was also collected using the method presented in Example 7 for five batches of oligosaccharide composition produced by the process described in Example 14. The results of this analysis are presented in Table 6.

TABLE 6

Max and min mol % of monomer radicals for the selected oligosaccharide composition

| Peak Number | Monomer radical | Max mol % | Min mol % |
|---|---|---|---|
| 1 | t-glucopyranose | 34.4% | 39.2% |
| 2 | 3-glucopyranose | 9.44% | 10.39% |
| 3 | 2-glucopyranose | 7.25% | 7.95% |
| 4 | 6-glucopyranose | 23.47% | 26.27% |
| 5 | 4-glucopyranose | 7.74% | 8.74% |
| 6 | 3,4-glucopyranose | 0.46% | 0.51% |
| 7 | 2,3-glucopyranose | 1.01% | 1.84% |
| 8 | 2,4-glucopyranose | 0.81% | 1.05% |
| 9 | 3,6-glucopyranose | 3.43% | 3.87% |
| 10 | 2,6-glucopyranose/ 4,6-glucopyranose | 5.23% | 5.65% |
| 11 | 2,3,4-glucopyranose | 0.07% | 0.12% |
| 12 | 3,4,6-glucopyranose | 0.24% | 0.26% |
| 13 | 2,4,6-glucopyranose | 0.32% | 0.39% |
| 14 | 2,3,6-glucopyranose | 0.24% | 0.27% |
| 15 | 2,3,4,6-glucopyranose | 0.04% | 0.07% |

Example 9: De-Monomerization Procedure

Figure 4:
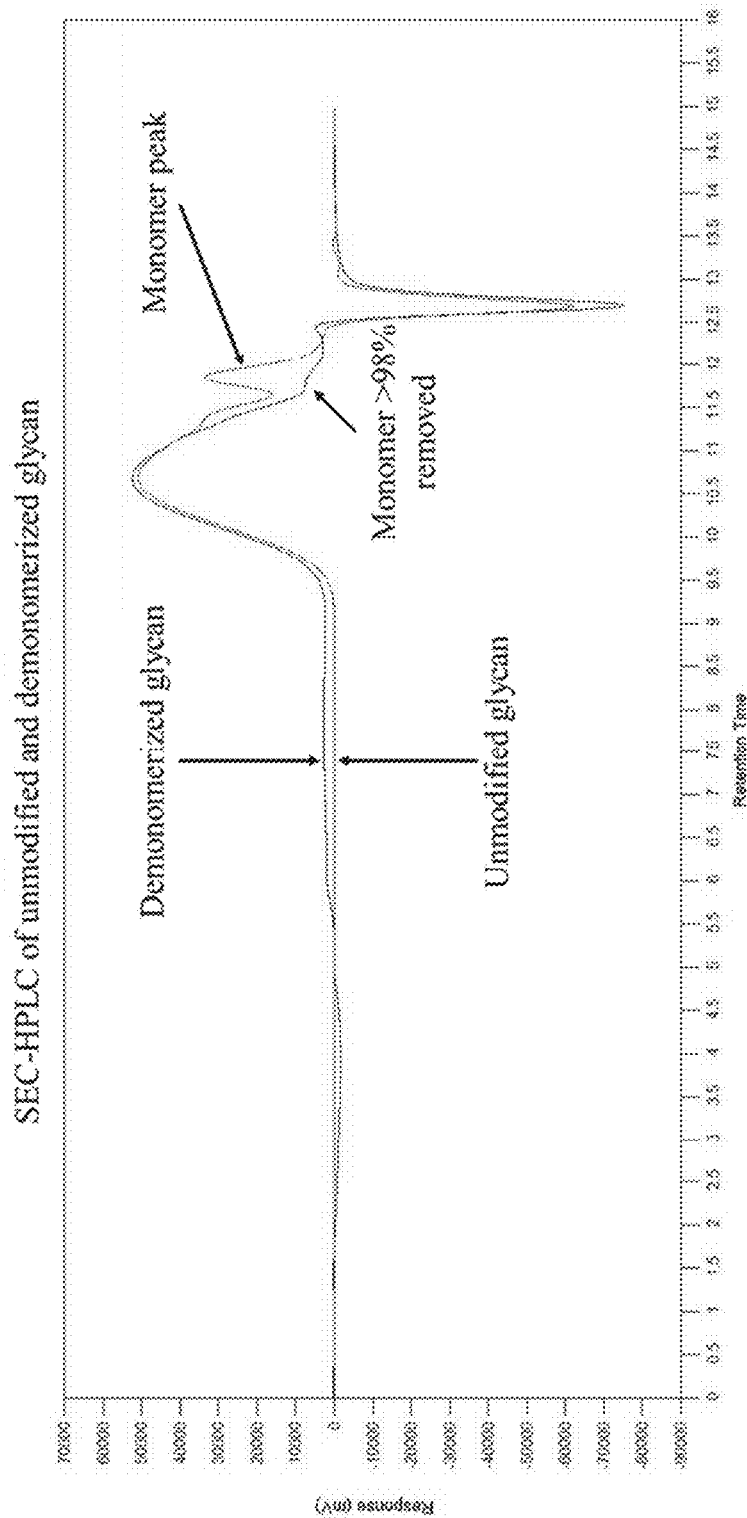
FIG. 4 depicts overlaid SEC-HPLC chromatograms of an unmodified oligosaccharide composition and an oligosaccharide composition that has been de-monomerized by amine column flash chromatography, as described in Example 9.

Individual batches of purified oligosaccharide composition, as produced using the process in Example 5, was concentrated on a rotatory evaporator to approximately 50 Bx as measured by a Brix refractometer. The resulting concentrated syrup (200 mg) was loaded onto a Teledyne ISCO RediSep Rf Gold Amine column (11 grams stationary phase) using a luer-tip syringe. Other similar columns such as the Biotage SNAP KP-NH Catridges may also be used. The concentrated syrup was then purified on a Biotage Isolera equipped with an ELSD detector using a 20/80 to 50/50 (v/v) deionized water/ACN mobile phase gradient over 55 column volumes. Other flash chromatography systems such as the Teledyne ISCO Rf may also be used. The flow rate was set in accordance with the manufacturer's specifications for the column and system. After the monomer fraction completely eluted at ~20 column volumes, the mobile phase was set to 100% water until the remainder of the oligosaccharide composition eluted and was collected. The non-monomer containing fractions were concentrated by rotary evaporation to afford the de-monomerized product. An SEC-HPLC of the unmodified and the de-monomerized composition is shown in FIG. 4.

Example 10: HSQC Analysis Procedure Using a Varian Unity Inova NMR Machine

A determination of HSQC NMR spectra of samples of the selected oligosaccharide composition, as described in Examples 1-4, was performed using a Varian Unity Inova NMR, according to the protocol described below. 158 preparations of the selected oligosaccharide composition were analyzed using the NMR methods described herein. 148 of these preparations were produced in a 22-liter reaction, as described in Example 6; five preparations were produced in a 189-liter (50-gallon) reaction, and five preparations were produced in a 2,840-liter (750-gallon) reaction, as described in Example 14. The oligosaccharide batches produced at the larger scales (189-liters and 2,840-liters) were not de-monomerized. A proportion of the oligosaccharide preparations produced at 22-liters were de-monomerized, as described in Example 9.

Method

Sample Preparation:

25 mg of a sample of the selected oligosaccharide composition was dissolved in 300 μL of D2O with 0.1% acetone as internal standard. The solution was then placed into a 3 mm NMR tube.

NMR Experiment:

Each sample was analyzed in a Varian Unity Inova operating at 499.83 MHz (125.69 MHz 13C) equipped with a XDB broadband probe with Z-axis gradient, tuned to 13C, and operating at 25° C. Each sample was subjected to a multiplicity-edited gradient-enhanced 1H-13C heteronuclear single quantum coherence (HSQC) experiment using the echo-antiecho scheme for coherence selection. The following pulse sequence diagram and acquisition and process ing parameters were used to obtain the NMR spectrum for each sample:
Pulse sequence diagram as depicted in FIG. 6 having
Acquisition Parameters
  1H Carrier Frequency=4 ppm
  13C Carrier Frequency=65 ppm
  Number of points in acquisition dimension=596
  Spectral range in acquisition dimension=6.00 ppm to 2.03 ppm
  Number of points in indirect dimension=300 complex points
  Spectral range in indirect dimension=120 ppm to 10 ppm
  Recycle delay=1 second
  One-bond 1H-13C coupling constant=$J_{CH}$=146 Hz
  Number of scans=8
  Temperature=298 K
  Solvent=D2O
Processing Parameters
  Window function in direct dimension=Gaussian broadening, 7.66 Hz
  Window function in indirect dimension=Gaussian broadening 26.48 Hz
  Processing=512 complex points in direct dimension, 1024 complex points in indirect dimension
Spectral Analysis:
The resulting spectra were analyzed using the MNova software package from Mestrelab Research (Santiago de Compostela, Spain). The spectra were referenced to the internal acetone signal (1H–2.22 ppm; 13C–30.8 ppm) and phased using the Regions2D method in both the F2 and F1 dimension. Apodization using 90 degree shifted sine was applied in both the F2 and F1 dimension. For each spectrum, individual signals (C-H correlations) were quantified by integration of their respective peaks using "predefined integral regions" with elliptical integration shapes. The resulting table of integral regions and values for each spectrum were normalized to a sum of 100 in order for the value to represent a percentage of the total. Peak integral regions were selected to avoid peaks associated with monomers.

Results

The 158 preparations of the selected oligosaccharide composition (148 preparations produced at the 22-L scale using the process in Example 6; five batches of the selected oligosaccharide composition produced at a 189-L (50-gallon) scale; and five batches of the selected oligosaccharide composition produced at a 2,840-L (750-gallon) scale using the process in Example 14) were analyzed using the NMR methods described above. Collectively, these batches comprised the following NMR peak signals:

|        | $^1$H Position (ppm) | | | $^{13}$C Position (ppm) | | |
|--------|--------------------|--|--|-----------------------|--|--|
|        | Center   | $^1$H Integral Region | | Center   | $^{13}$C Integral Region | |
| Signal | Position | from   | to     | Position | from     | to       |
| 1      | 5.39     | 5.4229 | 5.3620 | 100.31   | 99.9518  | 100.6747 |
| 2      | 5.36     | 5.3877 | 5.3310 | 98.48    | 98.2048  | 98.7590  |
| 3      | 5.35     | 5.3971 | 5.2958 | 99.77    | 99.3614  | 100.1807 |
| 4      | 5.22     | 5.2357 | 5.1994 | 102.55   | 102.1205 | 102.9759 |
| 5      | 5.19     | 5.2047 | 5.1684 | 93.95    | 93.6506  | 94.2530  |
| 6      | 5.17     | 5.1933 | 5.1540 | 96.06    | 95.7590  | 96.3614  |
| 7      | 5.1      | 5.1207 | 5.0772 | 96.77    | 96.5181  | 97.0120  |
| 8      | 5.03     | 5.0545 | 5.0009 | 109.19   | 108.7831 | 109.6024 |
| 9      | 4.97     | 5.0194 | 4.9173 | 98.49    | 97.8795  | 99.0964  |
| 10     | 4.8      | 4.8197 | 4.7827 | 96.77    | 96.5904  | 96.9518  |
| 11     | 4.71     | 4.7641 | 4.6658 | 103.64   | 103.2169 | 104.0723 |
| 12     | 4.64     | 4.6670 | 4.6193 | 103.54   | 103.1807 | 103.9036 |
| 13     | 4.63     | 4.6514 | 4.6008 | 104.53   | 104.2289 | 104.8313 |
| 14     | 4.52     | 4.5841 | 4.4476 | 103.34   | 102.8193 | 103.8675 |

The area under the curve (AUC) of each individual signal of signals 1-14 were determined relative to the total AUC of all signals 1-14. The AUC for each of signals 1-14 were determined for the 148 preparations of the selected oligosaccharide composition produced at the 22-L scale. Statistics that summarize the aggregated results of HSQC NMR analyses of the 148 preparations are presented in Table 7.

TABLE 7

Summary statistics for AUC of HSQC NMR signals 1-14 from 148 preparations of the selected oligosaccharide produced at the 22-L scale

|        | Center Position (ppm) | | Mean | Median | Standard deviation | Maximum | Minimum | Glycosidic Bond Type |
|--------|--------|--------|------|--------|-----------|---------|---------|---------|
| Signal | $^1$H  | $^{13}$C | AUC  | AUC    | AUC       | AUC     | AUC     |         |
| 1      | 5.39   | 100.31 | 4.29 | 4.27   | 0.28      | 5.11    | 3.61    | alpha-1,4 |
| 2      | 5.36   | 98.48  | 1.31 | 1.30   | 0.21      | 1.84    | 0.30    | alpha-1,2-beta |
| 3      | 5.35   | 99.77  | 7.73 | 7.71   | 0.39      | 9.31    | 6.16    | alpha-1,3 |
| 4      | 5.22   | 102.55 | 0.54 | 0.53   | 0.14      | 0.92    | 0.09    | — |
| 5      | 5.19   | 93.95  | 2.31 | 2.35   | 0.39      | 3.00    | 0.22    | alpha-1-alpha-1' |
| 6      | 5.17   | 96.06  | 1.00 | 0.99   | 0.15      | 1.38    | 0.57    | — |
| 7      | 5.1    | 96.77  | 1.42 | 1.43   | 0.18      | 1.80    | 0.88    | alpha-1,2-alpha |
| 8      | 5.03   | 93.95  | 0.74 | 0.73   | 0.22      | 1.38    | 0.06    | — |
| 9      | 4.97   | 98.49  | 33.99| 34.08  | 1.31      | 36.91   | 28.93   | alpha-1,6 |
| 10     | 4.8    | 96.77  | 0.84 | 0.83   | 0.16      | 1.46    | 0.33    | beta-1,2-beta, reducing |
| 11     | 4.71   | 103.64 | 7.61 | 7.67   | 0.45      | 8.49    | 5.80    | beta-1,3 |
| 12     | 4.64   | 103.54 | 2.45 | 2.41   | 0.24      | 3.28    | 1.85    | beta-1-alpha-1' |

TABLE 7-continued

Summary statistics for AUC of HSQC NMR signals 1-14 from 148 preparations of the selected oligosaccharide produced at the 22-L scale

| Signal | Center Position (ppm) $^1$H | Center Position (ppm) $^{13}$C | Mean AUC | Median AUC | Standard deviation AUC | Maximum AUC | Minimum AUC | Glycosidic Bond Type |
|---|---|---|---|---|---|---|---|---|
| 13 | 4.63 | 104.53 | 2.52 | 2.52 | 0.20 | 3.12 | 1.92 | beta-1,2-alpha |
| 14 | 4.52 | 103.34 | 31.82 | 31.51 | 1.31 | 36.31 | 29.59 | beta-1,4/beta-1,6 co-peak |

The relative size of each of the peaks (AUC) of the integral regions was determined for the 10 preparations of the selected oligosaccharide composition produced at the 50-gallon and 750-gallon scales (as described in Example 14). Statistics that summarize the aggregated results of HSQC NMR analyses of the 10 total preparations are presented in Table 8.

TABLE 8

Statistics for AUC of HSQC NMR signals 1-14 from 10 preparations of the selected oligosaccharide produced at the 50-gallon and 750-gallon scales

| Signal | Center Position (ppm) $^1$H | Center Position (ppm) $^{13}$C | Mean AUC | Median AUC | Standard deviation AUC | Maximum AUC | Minimum AUC | Glycosidic Bond Type |
|---|---|---|---|---|---|---|---|---|
| 1 | 5.39 | 100.31 | 4.08 | 4.08 | 0.16 | 4.31 | 3.84 | alpha-1,4 |
| 2 | 5.36 | 98.48 | 1.21 | 1.20 | 0.12 | 1.43 | 1.05 | alpha-1,2-beta |
| 3 | 5.35 | 99.77 | 7.60 | 7.55 | 0.23 | 8.02 | 7.33 | alpha-1,3 |
| 4 | 5.22 | 102.55 | 0.40 | 0.39 | 0.11 | 0.62 | 0.23 | — |
| 5 | 5.19 | 93.95 | 2.98 | 3.03 | 0.30 | 3.54 | 2.47 | alpha-1-alpha-1' |
| 6 | 5.17 | 96.06 | 0.96 | 0.98 | 0.14 | 1.13 | 0.69 | — |
| 7 | 5.1 | 96.77 | 1.48 | 1.49 | 0.19 | 1.75 | 1.21 | alpha-1,2-alpha |
| 8 | 5.03 | 93.95 | 0.28 | 0.24 | 0.11 | 0.55 | 0.20 | — |
| 9 | 4.97 | 98.49 | 36.30 | 36.36 | 0.84 | 37.63 | 35.19 | alpha-1,6 |
| 10 | 4.8 | 96.77 | 0.84 | 0.87 | 0.12 | 1.00 | 0.61 | beta-1,2-beta, reducing |
| 11 | 4.71 | 103.64 | 7.50 | 7.56 | 0.16 | 7.70 | 7.25 | beta-1,3 |
| 12 | 4.64 | 103.54 | 2.24 | 2.29 | 0.23 | 2.51 | 1.92 | beta-1-alpha-1' |
| 13 | 4.63 | 104.53 | 2.50 | 2.51 | 0.14 | 2.68 | 2.22 | beta-1,2-alpha |
| 14 | 4.52 | 103.34 | 30.28 | 30.33 | 0.37 | 30.95 | 29.58 | beta-1,4/beta-1,6 co-peak |

Example 11. Size Exclusion Chromatography

The weight-average molecular weight (MWw), number-average molecular weight (MWn), and polydispersity index (PDI) of batches and samples of the selected oligosaccharide composition, as described in Examples 1-4, were determined by SEC HPLC.
Method
These methods involved an Agilent 1100 with refractive index (RI) detector equipped with two Agilent PL Aquagel-OH 20 (7.5×300 mm, 5 μm) columns in series.
The mobile phase (0.2 M NaNO$_3$) was prepared by weighing 34 g of NaNO$_3$ (ACS grade reagent) and dissolving in 2000 mL of deionized (DI) water (from MiliQ water filter). The solution was filtered through a 0.2 μm filter.
Polymer standard solutions (10.0 mg/mL) of each of D-(+) Glucose (analytical standard, Sigma-Aldrich, Cat number 47829), PPS-pu1342 (Mp: 342), PPS-pull.3k (Mp: 1080), PPS-pul6k (Mp: 6100), PPS-pul10k (Mp: 9600), and PPS-pul22k (Mp: 22000) were prepared by weighing 20 mg of a standard into a separate 20 mL scintillation vial and adding 2.0 mL of DI water to each vial.

Sample A was prepared in duplicate. Approximately 300 mg of oligosaccharide sample was weighed into a 20 mL scintillation vail and 10 mL of DI water was added. The solution was mixed and filtered through a Acrodisc 25 mm syringe filter with a 0.2 μm polyethersulfone membrane.

Sample B was prepared in duplicate. Approximately 210 mg of oligosaccharide sample was weighed into a 20 mL scintillation vail and 10 mL of DI-water was added. The solution was mixed and filtered through a Acrodisc 25 mm syringe filter with a 0.2 μm polyethersulfone membrane.

The flow rate was set to 0.9 mL/min at least 2 hours before running samples with the column temperature and RI detector each set to 40° C. with the RI detector purge turned on.

The detector purge was turned off and the pump was run at 0.9 mL/min until an acceptable baseline was obtained prior to running the samples. The injection volume for each sample was 10 µL and run time was 28 minutes.

A blank sample consisting of DI water was run. Samples of each standard were run. Sample A was run. Sample B was run.

The peaks between 15 and 22 minutes were integrated. The monomer and the broad peak (the product) were integrated as shown in the sample chromatogram. The calibration curve fit type in Empower 3 software was set to 3$^{rd}$ order. The molecular weight distributions and polydispersity were calculated using Empower 3 software for the broad peak. The Mw, Mn and polydispersity of the product peak (DP2+) were reported.

Results

Eight batches of the selected oligosaccharide composition produced using the process described in Example 6 (at a 22 L scale); five batches of the selected oligosaccharide composition produced at a 50-gallon scale; and four batches of the selected oligosaccharide composition produced using the process described in Example 14 (at a 750-gallon scale) were analyzed using the SEC methods described above. The selected oligosaccharide batches produced using the process of Example 6 were de-monomerized using the procedure of Example 9. The SEC data collected for these batches are presented in Tables 8, 9, and 10.

TABLE 9

SEC data for selected production batches of oligosaccharide

22-Liter Oligosaccharide Batches

| Batch Number | 1 | 2 | 3 | 4 | 5 | 6 | 7 | 8 |
|---|---|---|---|---|---|---|---|---|
| Polydisperity | 1.5 | 1.5 | 1.5 | 1.5 | 1.5 | 1.5 | 1.5 | 1.6 |
| MWw | 1161 | 1120 | 1190 | 1151 | 1159 | 1098 | 1305 | 1411 |
| MWn | 782 | 756 | 768 | 764 | 758 | 747 | 845 | 863 |

TABLE 10

SEC data for selected production batches of oligosaccharide

189-Liter Oligosaccharide Batches

| Batch Number | 1 | 2 | 3 | 4 | 5 |
|---|---|---|---|---|---|
| Polydisperity | 1.6 | 1.6 | 1.6 | 1.6 | 1.5 |
| MWw | 1337 | 1342 | 1371 | 1221 | 1025 |
| MWn | 828 | 828 | 837 | 780 | 699 |

TABLE 11

SEC data for selected production batches of oligosaccharide

2840-Liter Oligosaccharide Batches

| Batch Number | 1 | 2 | 3 | 4 | 5 |
|---|---|---|---|---|---|
| Polydisperity | 1.4 | 1.4 | 1.4 | 1.5 | 1.5 |
| MWw | 963 | 869 | 918 | 1026 | 1038 |
| MWn | 668 | 626 | 648 | 698 | 697 |

Collectively, the average MWw of the selected oligosaccharide batches in Tables 8, 9, and 10 (the 22-liter, 189-liter, and 2,840-liter batches) was 1150, the average MWn of these batches was 755, and the average polydisperity was 1.5. The MWw ranged from 869-1411 (from 671 to 1630 at +/−3 standard deviations), the MWn ranged from 626-863 (from 544 to 966 at +/−3 standard deviations), and the polydisperity ranged from 1.4 to 1.6.

The average MWw of the selected oligosaccharide batches produced according to the method of Example 14 (the 2,840-liter batches of Table Z) was 963, the average MWn of these batches was 667, and the average polydisperity was 1.4. The MWw ranged from 869 to 1038 (from 483 to 1442 at +/−3 standard deviations), the MWn ranged from 626 to 697 (from 456 to 878 at +/−3 standard deviations), and the polydisperity ranged from 1.4 to 1.5.

Example 12. SEC HPLC Methodology for Determination of Impurities

SEC HPLC was used to determine the presence of residual organic acid impurities and related substances in batches and samples of the selected oligosaccharide composition described in Examples 1-4.

Method

These methods involved an Agilent 1100 with refractive index (RI) detector equipped with a guard column (Bio-Rad MicroGuard Cation H+ Cartridge, PIN 125-0129, or equivalent) and a Bio-Rad Aminex HPX-87H, 300×7.8 mm, 9 m, PIN 125-0140 column, or equivalent.

The mobile phase (25 mM $H_2SO_4$ in water) was prepared by filling a bottle with 2000 mL DI-water and slowly adding 2.7 mL of $H_2SO_4$. The solution was filtered through a 0.2 µm filter.

A standard solution was prepared by measuring 50±2 mg of reference standard into a 100-mL volumetric flask, adding the mobile phase to the 100-mL mark and mixing well.

A sample of a selected oligosaccharide composition (Sample A) was prepared in duplicate. Approximately 1000 mg of oligosaccharide sample was weighed into a 10 mL volumetric flask and the mobile phase was added up to the mark. The solution was mixed and filtered through a PES syringe filter with a 0.2 µm polyethersulfone membrane.

A sample of a selected oligosaccharide composition (Sample B) was prepared in duplicate. Approximately 700 mg of oligosaccharide sample was weighed into a 10 mL volumetric flask and the mobile phase was added up to the mark. The solution was mixed and filtered through a PES syringe filter with a 0.2 µm polyethersulfone membrane.

The flow rate was set to 0.65 mL/min at least 2 hours before running samples with the column temperature set to 50° C. and the RI detector temperature set to 50° C. with the RI detector purge turned on.

The detector purge was turned off and the pump was run at 0.65 mL/min until an acceptable baseline was obtained prior to running the samples. The injection volume for each sample was 50 µL and run time was 40 minutes.

A blank sample consisting of DI water was run. The standard, sample A, and sample B were each independently run.

The peaks at 7.5 min (Glucuronic acid), 11.3 min (Levoglucosan), 11.9 min (Lactic Acid), 13.1 min (Formic Acid), 14.2 min (Acetic Acid), 31.8 min (HMF), and 8.3 min (Glucose) were integrated. The calibration curve fit type in Empower 3 software was set to 3$^{rd}$ order.

Data

Four batches of the selected oligosaccharide described in Examples 1-4 and produced by the process described in Example 14, were tested using the HPLC method described above. The batches of the selected oligosaccharide composition (batches 1 to 5) had monomer percentages of 14%, 18%, 17%, 15%, and 13%, respectively, as described in Example 14.

TABLE 12

Impurities data for selected production batches of oligosaccharide

| Impurities | 2,840 L oligosaccharide batches | | | | |
|---|---|---|---|---|---|
| (% w/w) | 1 | 2 | 3 | 4 | 5 |
| Lactic acid | <LOQ | <LOQ | <LOQ | <LOQ | <0.03% |
| Formic acid | 0.23% | 0.24% | 0.09% | 0.07% | 0.23% |
| Acetic acid | <LOQ | <LOQ | <0.03% | <0.03 | <0.03% |
| Levulinic acid | 0.53% | 0.71% | 0.52% | 0.48% | 0.62% |
| Hydroxymethylfurfural (HMF) | <LOQ | <LOQ | <LOQ | <LOQ | <LOQ |
| Total impurities, excluding monomer | 2.2% | 2.4% | 2.1% | 2.0% | 2.3% |

Batch 1 of the selected oligosaccharide composition (Table 12) was spray-dried and assayed for impurities as described herein. The spray-dried preparation was found to have the following impurities profile: <LOQ lactic acid; 0.20% formic acid; LOQ acetic acid; 0.53% levulinic acid' 0.43% levoglucosan; 0.22% levoglucosan isomer; and <LOQ HMF. This oligosaccharide preparation had 1.5% total impurities (excluding monomer).

Example 13. SEC HPLC for Determination of DP1 to DP7

The relative amounts of oligosaccharides with a degree of polymerization (DP) of 1, 2, and 3+ in batches and samples of the selected oligosaccharide composition described in Examples 1-4 were determined by SEC HPLC.

Methods

These methods involved an Agilent 1100 with refractive index (RI) detector equipped with a guard column (Shodex SUGAR SP-G 6B Guard Column 6×50 mm, 10 μm, P/N F6700081, or equivalent) and a chromatography column (Shodex Sugar SP0810, 8.0×300 mm, 8 μm, P/N F6378105, or equivalent).

The mobile phase (0.1 M NaNO$_3$) was prepared by weighing 42.5 g of NaNO$_3$ (ACS grade reagent) and dissolving it in 5000 mL of deionized (DI) water (from MiliQ water filter). The solution was filtered through a 0.2 μm filter.

Polymer standard solutions (10.0 mg/mL) of each of D-(+) Glucose Mp 180, Carbosynth Ltd Standard, or equivalent (CAS #50-99-7) (DP1); Maltose Mp 342, Carbosynth Ltd Standard, or equivalent (CAS #69-79-4) (DP2); Maltotriose Mp 504, Carbosynth Ltd Standard, or equivalent (CAS #1109-28-0) (DP3); Maltotetraose Mp 667, Carbosynth Ltd Standard, or equivalent (CAS #34612-38-9) (DP4); Maltopentaose Mp 828, Carbosynth Ltd Standard, or equivalent (CAS #34620-76-3) (DP5); Maltohexaose Mp 990, Carbosynth Ltd Standard, or equivalent (CAS #34620-77-4) (DP6); Maltoheptaose Mp 1153, Carbosynth Ltd Standard, or equivalent (CAS #34620-78-5) (DP7); and Maltooctaose Mp 1315, Carbosynth Ltd Standard, or equivalent (CAS #6156-84-9) (DP8), were prepared by weighing 10 mg of each standard into an individual 1.5 mL centrifuge tube and adding DI water to make 10 mg/mL solution.

Samples of the selected oligosaccharide composition were prepared as 10 mg/mL concentrated samples or dilute aqueous samples to 2.5-3.5 Brix.

The flow rate was set to 1.0 mL/min at least 2 hours before running samples with the column temperature set to 70° C. and the RI detector temperature set to 40° C. with the RI detector purge turned on.

The detector purge was turned off and the pump was run at 1.0 mL/min until an acceptable baseline was obtained prior to running the samples. The injection volume of each of the samples was 5 μL and the run time was 15 minutes.

A blank sample consisting of DI water, the individual standards, and the sample were independently run.

Figure 5:
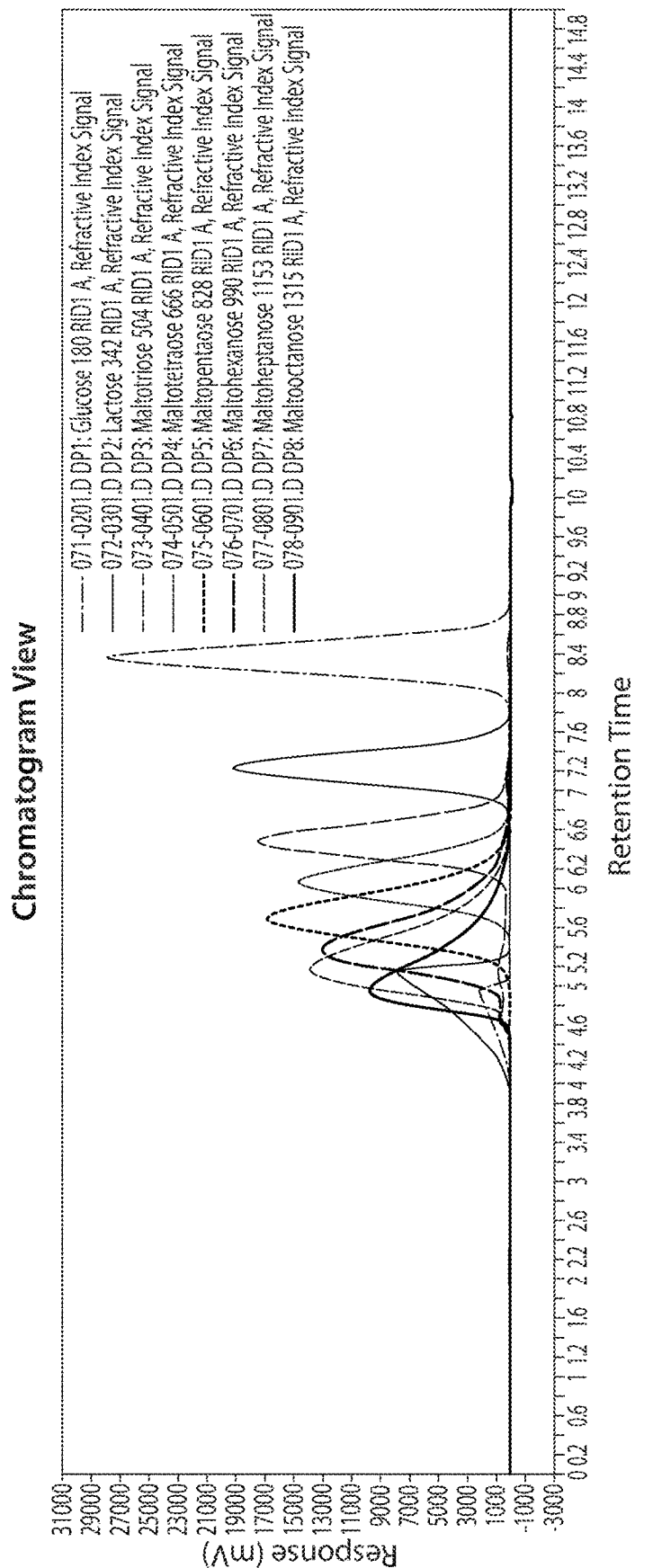
FIG. 5 depicts an overlay of SEC-HPLC chromatograms of standard glycans for use in Example 13.

Each peak between 4 and 9.2 minutes in the sample run, corresponding to the individual standards, was integrated. An overlay of the standards is shown in FIG. 5. The calibration curve fit type in Empower 3 software was set to $3^{rd}$ order. The DP1, DP2, and DP3+ values of the samples of the selected oligosaccharide composition were determined using these methods.

Results

Samples of the selected oligosaccharide composition produced at the 22-L scale (7 batches, Example 6), 50-gallon scale (3 batches), and 750-gallon scale (3 batches, Example 14) were assayed as described above. Table 13 provides the results of these analyses.

TABLE 13

DP1, DP2, and DP3+ fractions of selected oligosaccharide production batches

| | 22-Liter Production Batches | | | | | | | 50-Gallon Production Batches | | | 750-Gallon Production Batches | | |
|---|---|---|---|---|---|---|---|---|---|---|---|---|---|
| | 6 | 9 | 10 | 11 | 12 | 13 | 14 | 1 | 2 | 3 | 2 | 3 | 4 |
| DP1 (%) | 15.29 | 12.23 | 12.89 | 12.29 | 12.72 | 12.19 | 10.44 | 11.52 | 19.15 | 11.41 | 18.09 | 17.33 | 15.18 |
| DP2 (%) | 8.95 | 7.59 | 7.84 | 7.35 | 7.76 | 7.69 | 6.76 | 6.80 | 10.31 | 6.67 | 10.09 | 9.64 | 8.51 |
| DP3+ (%) | 75.76 | 80.17 | 79.27 | 80.36 | 79.52 | 80.12 | 82.80 | 11.52 | 70.54 | 81.92 | 71.82 | 17.33 | 76.31 |
| Total (%) | 99.99 | 100 | 100 | 100 | 100 | 100 | 100 | 100 | 100 | 100 | 100 | 100 | 100 |

Overall, the samples of the selected oligosaccharide composition exhibited a mean monomer (DP1) percentage of 14.41% (±2.93%) and a mean disaccharide (DP2) percentage of 8.38% (±1.31%). The selected oligosaccharide batches produced according to the production process of Example 14 exhibited a mean monomer (DP1) percentage of 16.87% (±1.51%) and a mean disaccharide (DP2) percentage of 9.41% ((±0.81%).

Example 14. Production of the Oligosaccharide Composition at 780 kg Scale from Dextrose Monohydrate The selected oligosaccharide composition described in Examples 1-4 was synthesized at 780 kg scale in a 2,840 L (750-gallon) reactor with overhead agitation.

To initiate production, about 780 kg of food grade dextrose monohydrate powder and approximately 100 kg of solid acid catalyst (e.g., styrene-divinylbenzene comprising sulfonic acid moieties, e.g., Dowex FPC16 UPS H Ion Exchange Resin) were added to a reactor at room temperature and heated with continuous stirring to reach an internal temperature of 130° C. This internal temperature was held for 2 hours. The distillate was condensed into a condensate collection tank. The molar ratio of water condensate to feed sugar (dextrose) was between 0.4 and 0.9, generally. The oligosaccharide mixture in the reactor was then diluted with hot purified water to approximately 50% solids concentration, filtered through a 100-μm filter, and transferred to drums.

The crude material was charged back into the reactor with purified water and agitated for 10 minutes at 25° C. The resulting solution was sequentially processed with the following ion-exchange resins to reduce trace metal ions, color, and organic acids: Dowex 88 (H) Resin (processed for 60 minutes), Dowex Optipore SD-2 Adsorbent Resin (processed for 240 minutes), and Dowex Monosphere 77 Resin (processed for 60 minutes). Following agitation with each resin, the material was processed through a filter bag or centrifuged to remove the resin and then added back to the reactor.

The final solution was then concentrated to 70-74° Bx (i.e., approximately 70% solids concentration, where 1° Bx is 1 gram of sucrose in 100 grams of aqueous solution) under vacuum at 65° C. The vacuum was released, and a sample was pulled to verify concentration prior to discharge. The purified oligosaccharide composition was cooled to 55° C., and the resulting solution was filtered through a 20-μm filter and collected into containers. The containers were stored at ambient temperature. Table 14 summarizes certain characteristics of four of the batches of the selected oligosaccharide produced at the 2,840-liter scale.

TABLE 14

Characteristics of batches of the selected oligosaccharide produced at 2,840 liters

| | Oligosaccharide batch (2,840 L) | | | | |
|---|---|---|---|---|---|
| | 1 | 2 | 3 | 4 | 5 |
| Total Glycan (DP2+) in syrup (% dry basis) | 88% | 82% | 84% | 86% | 89% |
| Water content | 28% | 28% | 28% | 30% | 30% |
| Monomer (% dry basis) | 14% | 18% | 17% | 15% | 13% |
| pH | 3.2 | 3.2 | 3.2 | 3.2 | 3.2 |
| Molar ratio water condensate:sugar | 0.6 | 0.6 | 0.6 | 0.6 | 0.7 |

The purified oligosaccharide composition was then converted to solid powder by mixing the purified composition and United States Pharmacopeia (USP) grade water in a vessel until fully dissolved at 50% solids concentration. The solution was then spray dried, and the resultant powder was transferred into a low-density polyethylene (LDPE) bag. This material may be packaged, e.g., in twist-tied double LDPE bags with approximately 280 g desiccant placed between two LDPE bags, and stored, e.g., in a 30-gallon high density polyethylene (HDPE) container at controlled room temperature.

Example 15. Determination of Soluble, Insoluble, and Total Dietary Fiber

The amount of dietary fiber of batches of the selected oligosaccharide composition described in Examples 1-4 was measured according to the methods of AOAC 2011.25 (AOAC International, AOAC Official Method 2011.25, Insoluble, Soluble, and Total Dietary Fiber in Foods). The percent Dextrose Equivalent (DE) (dry basis) of these oligosaccharide batches was also measured according to the Food Chemicals Codex (FCC). Five oligosaccharide batches were analyzed, each with a different DP1 monomer level. Monomer was not removed from one of the batches. Monomer was removed from four of the oligosaccharide batches, so that they had 10% monomer, 5% monomer, 3% monomer, or <1% monomer. The results of this analysis are presented in Table 15.

TABLE 15

Characteristics of batches of the selected oligosaccharide produced at 2,840 liters

| | 1 | 2 | 3 | 4 | 5 |
|---|---|---|---|---|---|
| DP1 Levels | DP1 not removed | 10% | 5% | 3% | <1% |
| Moisture (Karl Fischer) | 5% | 9% | 4% | 4% | 3% |
| Dextrose Equivalent (dry basis) | 27% | 24% | 19% | 18% | 14% |
| Soluble Dietary Fiber Precipitate (SDFP) (dry basis) | <LOQ | <LOQ | <LOQ | <LOQ | <LOQ |
| Low Molecular Weight Soluble Dietary Fiber (LMWSDF) (dry basis) | 75% | 85% | 93% | 94% | 93% |
| Total Soluble Dietary Fiber (SDFP + LMWSDF) (dry basis) | 75% | 85% | 93% | 94% | 93% |
| Insoluble Fiber (IDF) (dry basis) | <LOQ | <LOQ | <LOQ | <LOQ | <LOQ |
| High Molecular Weight Dietary Fiber (HMWDF) (dry basis) | <LOQ | <LOQ | <LOQ | <LOQ | <LOQ |
| Total Dietary Fiber (HMWDF + LMWSDF) (dry basis) | 75% | 85% | 93% | 94% | 93% |

Example 16. Study of the Selected Oligosaccharide Composition in Human Subjects with UCD The safety and GI tolerability of the selected oligosaccharide composition, as described in Examples 1-4, was evaluated in four human adult subjects with well-controlled urea cycle disorders (UCD) in an open-label single-center clinical study. The study also aimed to evaluate the effect of the oligosaccharide composition on nitrogen metabolism in UCD patients. The subjects were at least 14 years old, had no history of N-acetylglutamate synthesase (NAGS) deficiency, liver transplant, or other medical condition that could cause hyperammonemia (HA). Subjects first went through a run-in period (days −7 to −1) and were then given lactose-[15N]-ureide, a stable isotope tracer, on days 0 to 3 (5.7 mg/kg) to quantify gut bacteria-derived ammonia. This isotope tracer was also given again at days 21 to 24 (5.7 mg/kg). Lactose-[15N]-ureide is used as a marker for nitrogen metabolism. This stable isotope tracer is indigestible by human enzymes but is a substrate for enzymes produced by colonic bacteria, which separate the urea and lactose portions, and then hydrolyze urea to ammonia. Production of 15N-ammonia after tracer consumption is indicative of colonic bacterial (urease) enzyme activity. Increasing doses (for one subject up to 42 grams per day maximum dose, and for three subjects up to 72 grams per day maximum dose) of the oligosaccharide composition were administered to the subjects during four periods (period 1 (days 4-8), period 2 (days 9-13), period 3 (days 14-18), and period 4 (days 19-24)) to maximize tolerability. The last dose was followed by a washout and safety follow-up period from days 25 to 32. Blood, urine, and stool were collected from the subjects at various timepoints during the study for safety assessment and to assess biomarkers for gut nitrogen metabolism. Safety assessments were gathered from the subjects on day 25 through adverse event (AE) reporting and a gastrointestinal tolerability questionnaire (GITQ).

The results showed that the selected oligosaccharide composition was safe and generally well tolerated as assessed using the gastrointestinal tolerability questionnaire (GITQ). The subjects reported mild flatulence and GI sounds but did not report any clinically significant safety signals. There were no treatment-emergent adverse events and no treatment discontinuations due to adverse events.

The data suggest that the oligosaccharide composition can reduce ammonia in UCD human subjects. A reduction in ammonia is suggested if there is an increase of the tracer excreted in the stool and/or a decreased amount of the tracer excreted in the urine. There was a general increase of the 15N tracer in the stool of the subjects (relative to a baseline %) and a decrease of the 15N tracer in the urine of subjects (relative to a baseline %). The urine excretion of the labeled nitrogen decreased in two of three evaluable patients (i.e., patients who submitted the required samples). The mean decrease in urinary labeled 15N excretion was 15.27% (SD 23.66) across subjects. The amount of labelled nitrogen increased in the stool of three of four subjects. The mean change in labeled 15N excretion in the stool of the subjects was 39.39% (SD 26.79). Plasma NH3 levels were controlled in the subjects and remained at normal (baseline) levels throughout the study.

These data suggest that the selected oligosaccharide composition can be used to treat subjects with UCD and other subjects with symptoms associated with hyperammonemia.

Equivalents and Terminology

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments, optional features, modification and variation of the concepts herein disclosed may be resorted to by those skilled in the art, and that such modifications and variations are considered to be within the scope of this disclosure.

In addition, where features or aspects of the disclosure are described in terms of Markush groups or other grouping of alternatives, those skilled in the art will recognize that the disclosure is also thereby described in terms of any individual member or subgroup of members of the Markush group or other group.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein. Variations of those embodiments may become apparent to those of ordinary skill in the art upon reading the foregoing description.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Those skilled in the art will recognize, or be able to ascertain using no more than routine experimentation, many equivalents to the specific embodiments of the invention described herein. Such equivalents are intended to be encompassed by the following claims.

What is claimed is:

1. An oligosaccharide composition comprising a plurality of oligosaccharides, the plurality of oligosaccharides being characterized by a multiplicity-edited gradient-enhanced ¹H-¹³C heteronuclear single quantum coherence (HSQC) NMR spectrum comprising signals 1, 3, and 4, each signal having properties as follows:

| Signal | Center Position (ppm) ¹H | Center Position (ppm) ¹³C | Area under the curve (AUC) (% of total areas of signals observed and assigned to the oligosaccharide composition) | Glycosidic Bond Type |
|---|---|---|---|---|
| 1 | 5.39 | 100.31 | 3.37-4.78 | alpha-1,4 |
| 3 | 5.35 | 99.77 | 6.64-8.71 | alpha-1,3 |
| 4 | 5.22 | 102.55 | 0.00-0.95 | — |

2. The composition of claim 1, wherein the spectrum further comprises 1-2 signals selected from signals 8 and 9, each signal having properties as follows:

| Signal | Center Position (ppm) ¹H | Center Position (ppm) ¹³C | Area under the curve (AUC) (% of total areas of signals observed and assigned to the oligosaccharide composition) | Glycosidic Bond Type |
|---|---|---|---|---|
| 8 | 5.03 | 93.95 | 0.00-0.89 | — |
| 9 | 4.97 | 98.49 | 32.69-40.14 | alpha-1,6. |

3. The composition of claim 1, wherein the spectrum further comprises 1-6 signals selected from signals 6, 7, 11, 12, 13, and 14, each signal having properties as follows:

| Signal | Center Position (ppm) ¹H | Center Position (ppm) ¹³C | Area under the curve (AUC) (% of total areas of signals observed and assigned to the oligosaccharide composition) | Glycosidic Bond Type |
|---|---|---|---|---|
| 6 | 5.17 | 96.06 | 0.26-1.55 | — |
| 7 | 5.1 | 96.77 | 0.65-2.30 | alpha-1,2-alpha |
| 11 | 4.71 | 103.64 | 6.78-8.16 | beta-1,3 |
| 12 | 4.64 | 103.54 | 1.23-3.20 | beta-1-alpha-1' |
| 13 | 4.63 | 104.53 | 1.80-3.09 | beta-1,2-alpha |
| 14 | 4.52 | 103.34 | 28.46-32.06 | beta-1,4/beta-1,6 co-peak. |

4. The composition of claim 1, wherein the spectrum further comprises 1-3 signals selected from signals 2, 5, and 10, each signal having properties as follows:

| Signal | Center Position (ppm) ¹H | Center Position (ppm) ¹³C | Area under the curve (AUC) (% of total areas of signals observed and assigned to the oligosaccharide composition) | Glycosidic Bond Type |
|---|---|---|---|---|
| 2 | 5.36 | 98.48 | 0.69-1.78 | alpha-1,2-beta |
| 5 | 5.19 | 93.95 | 1.56-4.45 | alpha-1-alpha-1' |
| 10 | 4.8 | 96.77 | 0.26-1.35 | beta-1,2-beta, reducing. |

5. The composition of claim 1, wherein the composition comprises signals 1-14, wherein each is characterized by an ¹H integral region and a ¹³C integral region, defined as follows:

| | ¹H Position (ppm) | | | ¹³C Position (ppm) | | |
|---|---|---|---|---|---|---|
| | Center | ¹H Integral Region | | Center | ¹³C Integral Region | |
| Signal | Position | from | to | Position | from | to |
| 1 | 5.39 | 5.4229 | 5.3620 | 100.31 | 99.9518 | 100.6747 |
| 2 | 5.36 | 5.3877 | 5.3310 | 98.48 | 98.2048 | 98.7590 |
| 3 | 5.35 | 5.3971 | 5.2958 | 99.77 | 99.3614 | 100.1807 |
| 4 | 5.22 | 5.2357 | 5.1994 | 102.55 | 102.1205 | 102.9759 |
| 5 | 5.19 | 5.2047 | 5.1684 | 93.95 | 93.6506 | 94.2530 |
| 6 | 5.17 | 5.1933 | 5.1540 | 96.06 | 95.7590 | 96.3614 |
| 7 | 5.1 | 5.1207 | 5.0772 | 96.77 | 96.5181 | 97.0120 |
| 8 | 5.03 | 5.0545 | 5.0009 | 109.19 | 108.7831 | 109.6024 |
| 9 | 4.97 | 5.0194 | 4.9173 | 98.49 | 97.8795 | 99.0964 |
| 10 | 4.8 | 4.8197 | 4.7827 | 96.77 | 96.5904 | 96.9518 |
| 11 | 4.71 | 4.7641 | 4.6658 | 103.64 | 103.2169 | 104.0723 |
| 12 | 4.64 | 4.6670 | 4.6193 | 103.54 | 103.1807 | 103.9036 |
| 13 | 4.63 | 4.6514 | 4.6008 | 104.53 | 104.2289 | 104.8313 |
| 14 | 4.52 | 4.5841 | 4.4476 | 103.34 | 102.8193 | 103.8675. |

6. The composition of claim 1, wherein the NMR spectrum is obtained by subjecting a sample of the composition to a multiplicity-edited gradient-enhanced ¹H-¹³C heteronuclear single quantum coherence (HSQC) experiment using an echo-antiecho scheme for coherence selection using the pulse sequence diagram as set forth in FIG. 6, acquisition parameters and processing parameters:
Acquisition parameters
¹H Carrier Frequency=4 ppm
¹³C Carrier Frequency=65 ppm
Number of points in acquisition dimension=596
Spectral range in acquisition dimension=6.00 ppm to 2.03 ppm
Number of points in indirect dimension=300 complex points
Spectral range in indirect dimension=120 ppm to 10 ppm
Recycle delay=1 second
One-bond ¹H-¹³C coupling constant=$J_{CH}$=146 Hz
Number of scans=8
Temperature=298 K
Solvent=D2O
Processing parameters
Window function in direct dimension=Gaussian broadening, 7.66 Hz
Window function in indirect dimension=Gaussian broadening 26.48 Hz
Processing=512 complex points in direct dimension, 1024 complex points in indirect dimension.

7. The composition of claim 1, wherein the mean degree of polymerization (DP) of the oligosaccharide composition is from about DP5 to about DP11.

8. A method of reducing ammonia levels in a human subject, comprising administering to the human subject an effective amount of an oligosaccharide composition according to claim 1.

9. A method of reducing the rate of hyperammonemic crises in a human subject having or having been diagnosed with a disease or condition associated with hyperammonemia, comprising administering to the human subject an effective amount of an oligosaccharide composition according to claim 1.

10. The method of claim 9, wherein the subject has or has been diagnosed as having a urea cycle disorder or hepatic encephalopathy (HE).

11. A method for treating encephalopathy in a human subject, comprising administering to the human subject an effective amount of an oligosaccharide composition according to claim 1.

12. The composition of claim 1, wherein the composition comprises 16% to 24% dextrose equivalent (dry basis).

13. An oligosaccharide composition comprising a plurality of oligosaccharides, each oligosaccharide comprising a plurality of monomer radicals;

the plurality of oligosaccharides comprising two or more types of monomer radicals selected from radicals (1)-(7), wherein the selected radicals are present in the plurality of oligosaccharides in a defined molar percentage (mol %) range:
  (1) 2-glucopyranose diradicals, representing 6.15-9.54 mol % of monomer radicals in the plurality of oligosaccharides;
  (2) 6-glucopyranose diradicals, representing at least 18.94 mol % of monomer radicals in the plurality of oligosaccharides;
  (3) 4-glucopyranose diradicals, representing 6.63-8.74 mol % of monomer radicals in the plurality of oligosaccharides;
  (4) 3,4-glucopyranose triradicals, representing less than 1.42 mol % of monomer radicals in the plurality of oligosaccharides;
  (5) 2,3-glucopyranose triradicals, representing 1.01-2.59 mol % of monomer radicals in the plurality of oligosaccharides;
  (6) 3,4,6-glucopyranose tetraradicals, representing less than 1.00 mol % of monomer radicals in the plurality of oligosaccharides; and
  (7) 2,4,6-glucopyranose tetraradicals, representing less than 0.72 mol % of monomer radicals in the plurality of oligosaccharides;

wherein at least one of the two or more types of monomer radicals is (4) or (7).

14. The composition of claim 13, further comprising one or more types of monomer radicals selected from radicals (8)-(12):
  (8) t-glucopyranose monoradicals, representing 26.87-46.98 mol % of monomer radicals in the plurality of oligosaccharides;
  (9) 3-glucopyranose diradicals, representing at least 6.94 mol % of monomer radicals in the plurality of oligosaccharides;
  (10) 2,4-glucopyranose triradicals, representing less than 1.43 mol % of monomer radicals in the plurality of oligosaccharides;
  (11) 2,6-glucopyranose/4,6-glucopyranose triradicals, representing less than 9.66 mol % of monomer radicals in the plurality of oligosaccharides; and
  (12) 2,3,4-glucopyranose radicals, representing 0.07-0.85 mol % of monomer radicals in the plurality of oligosaccharides.

15. The composition of claim 13, further comprising one or more types of monomer radicals selected from radicals (13)-(15):
  (13) 3,6-glucopyranose triradicals, representing 2.35-6.01 mol % of monomer radicals in the plurality of oligosaccharides;
  (14) 2,3,6-glucopyranose tetraradicals, representing 0.06-0.86 mol % of monomer radicals in the plurality of oligosaccharides; and
  (15) 2,3,4,6-glucopyranose pentaradicals, representing less than 0.61 mol % of monomer radicals in the plurality of oligosaccharides.

* * * * *